US012595466B2

(12) United States Patent
Smith et al.

(10) Patent No.: US 12,595,466 B2
(45) Date of Patent: Apr. 7, 2026

(54) NKR VARIANTS FOR INCREASED PRODUCTION OF ISOBUTANOL

(71) Applicant: Gevo, Inc., Englewood, CO (US)

(72) Inventors: Christopher Smith, Englewood, CO (US); Timothy Hanly, Englewood, CO (US); Jeanne Benoit, Englewood, CO (US)

(73) Assignee: GEVO, INC., Englewood, CO (US)

( * ) Notice: Subject to any disclaimer, the term of this patent is extended or adjusted under 35 U.S.C. 154(b) by 691 days.

(21) Appl. No.: 17/909,353

(22) PCT Filed: Mar. 5, 2021

(86) PCT No.: PCT/US2021/021096
§ 371 (c)(1),
(2) Date: Sep. 2, 2022

(87) PCT Pub. No.: WO2021/178805
PCT Pub. Date: Sep. 10, 2021

(65) Prior Publication Data
US 2023/0087872 A1      Mar. 23, 2023

Related U.S. Application Data

(60) Provisional application No. 62/986,378, filed on Mar. 6, 2020.

(51) Int. Cl.
*C12N 15/81* (2006.01)
*C12N 9/04* (2006.01)
*C12P 7/16* (2006.01)

(52) U.S. Cl.
CPC ........... *C12N 9/0006* (2013.01); *C12N 15/81* (2013.01); *C12P 7/16* (2013.01); *C12Y 101/01086* (2013.01)

(58) Field of Classification Search
CPC ......... C12P 7/16; C12N 9/0006; C12N 15/52; C12Y 101/01086
See application file for complete search history.

(56) References Cited

U.S. PATENT DOCUMENTS

| | | | |
|---|---|---|---|
| 4,859,596 | A | 8/1989 | Hollenberg et al. |
| 4,943,529 | A | 7/1990 | Van et al. |
| 6,015,891 | A | 1/2000 | Adang et al. |
| 7,943,366 | B2 | 5/2011 | Rajgarhia et al. |
| 8,017,375 | B2 | 9/2011 | Feldman et al. |
| 8,133,715 | B2 | 3/2012 | Buelter et al. |
| 8,153,415 | B2 | 4/2012 | Buelter et al. |
| 8,158,404 | B2 | 4/2012 | Lies et al. |
| 8,232,089 | B2 | 7/2012 | Urano et al. |
| 2009/0215137 | A1 | 8/2009 | Hawkins et al. |
| 2009/0226991 | A1 | 9/2009 | Feldman et al. |
| 2010/0143997 | A1 | 6/2010 | Buelter et al. |
| 2011/0020889 | A1 | 1/2011 | Feldman et al. |
| 2011/0076733 | A1 | 3/2011 | Urano et al. |
| 2011/0183392 | A1 | 7/2011 | Feldman et al. |
| 2011/0201072 | A1 | 8/2011 | Bastian et al. |
| 2014/0295512 | A1* | 10/2014 | Buelter .................... C12P 7/16 |
| | | | 435/254.2 |
| 2014/0295513 | A1 | 10/2014 | Meinhold et al. |

FOREIGN PATENT DOCUMENTS

| | | | |
|---|---|---|---|
| WO | WO-0121772 | A2 | 3/2001 |
| WO | WO-2007050671 | A2 | 5/2007 |
| WO | WO-2008098227 | A2 | 8/2008 |
| WO | WO-2009076480 | A2 | 6/2009 |
| WO | WO-2009103533 | A1 | 8/2009 |
| WO | WO-2010017230 | A2 | 2/2010 |
| WO | WO-2010031772 | A2 | 3/2010 |
| WO | WO-2010045629 | A2 | 4/2010 |
| WO | WO-2010075504 | A2 | 7/2010 |
| WO | WO-2012129555 | A2 | 9/2012 |
| WO | WO-2012133961 | A1 | 10/2012 |
| WO | WO-2013048599 | A2 | 4/2013 |
| WO | WO-2021178805 | A1 | 9/2021 |

OTHER PUBLICATIONS

Partial Supplementary European Search Report for European Application No. EP21765419.3 dated Mar. 6, 2024, 11 pages.
Database Geneseq [Online] May 23, 2013 (May 23, 2013), "Cryptobacterium curtum ketol-acid reductoisomerase, Seq 4.", XP93184156, retrieved from EBI accession No. GSP:BAM93506 Database accession No. BAM93506, 4 pages.
Database Geneseq [Online] May 23, 2013 (May 23, 2013), "Eggerthella sp. ketol-acid reductoisomerase, Seq 6.", XP93184198, retrieved from EBI accession No. GSP:BAM93508 Database accession No. BAM93508, 2 pages.
Database Refseq [Online] EBI; Jan. 26, 2020 (Jan. 26, 2020), "ketol-acid reductoisomerase [Enterorhabdus sp. P55]", XP93184521, Database accession No. WP_160710514, 1 page.
Database Refseq [Online] EBI; Oct. 7, 2019 (Oct. 7, 2019), XP93184207, retrieved from NCBI Database accession No. WP_117204710, 1 page.
Database Refseq [Online] EBI; Oct. 7, 2019 (Oct. 7, 2019), XP93184179, retrieved from NCBI Database accession No. WP_144744080, 1 page.
Database UniProt [Online] Aug. 10, 2010 (Aug. 10, 2010), "RecName: Full=Ketol-acid reductoisomerase (NADP(+)) {ECO:00002561 HAMAP-Rule:MF 00435}; Short=KARI {ECO:00002561HAMAPRule: MF 00435}; EC=1.1.1.86 {ECO:00002561HAMAP-Rule:MF_00435}; AltName: Full= Acetohydroxy-acid isomeroreductase {ECO:00002561 HAMAP-Rule:MF 00435}; Short=AHIR f ECO:00002561HAMAP-Rule:M", XP93184517, retrieved from EBI accession No. Uniprot:D6Y6A2 Database accession No. D6Y6A2, 3 pages.

(Continued)

*Primary Examiner* — Tekchand Saidha
(74) *Attorney, Agent, or Firm* — Husch Blackwell LLP

(57) ABSTRACT

The present invention relates to recombinant microorganisms comprising at least one nucleic acid molecule encoding a ketol-acid reductoisomerase (KARI) or modified NADH-dependent variant thereof, wherein said KARI is at least about 60% identical to SEQ ID NO: 2. In various aspects of the invention, the recombinant microorganisms may comprise an isobutanol producing metabolic pathway and can be used in methods of making isobutanol.

10 Claims, 15 Drawing Sheets

Specification includes a Sequence Listing.

(56)                References Cited

OTHER PUBLICATIONS

Database UniProt [Online] Dec. 11, 2019 (Dec. 11, 2019), "RecName: Full=Ketol-acid reductoisomerase (NADP(+)) {ECO:00002561 HAMAP-Rule:MF 00435}; Short=KARI {ECO:00002561HAMAPRule: MF 00435}; EC=1.1.1.86 {ECO:0000256IHAMAP-Rule:MF_00435}; AltName: Full= Acetohydroxy-acid isomeroreductase {ECO:00002561 HAMAP-Rule:MF 00435}; Short=AHIR {ECO:0000256IHAMAP-Rule:M", XP93184176, retrieved from EBI accession No. Uniprot:A0A5K1IQU6 Database accession No. A0A5K1IQU6, 3 pages.

Database UniProt [Online] Feb. 13, 2019 (Feb. 13, 2019), "RecName: Full=Ketol-acid reductoisomerase (NADP(+)) {ECO:00002561 HAMAP-Rule:MF 00435}; Short=KARI {ECO:00002561HAMAPRule: MF 00435}; EC=1.1.1.86 {ECO:00002561HAMAP-Rule:MF_00435}; AltName: Full= Acetohydroxy-acid isomeroreductase {ECO:00002561 HAMAP-Rule:MF 00435}; Short=AHIR fECO:00002561HAMAP-Rule:M", XP93184520, retrieved from EBI accession No. UNIPROT:A0A3N0AQ93 Database accession No. A0A3N0AQ93, 3 pages.

Database UniProt [Online] Feb. 13, 2019 (Feb. 13, 2019), "RecName: Full=Ketol-acid reductoisomerase (NADP(+)) {ECO:00002561 HAMAP-Rule:MF 00435}; Short=KARI fECO:00002561HAMAP-Rule:MF 00435}; EC=1.1.1.86 {ECO:00002561HAMAP-Rule:MF_ 00435}; AltName: Full=Acetohydroxy-acid isomeroreductase {ECO:00002561 HAMAP-Rule: MF 00435}; Short=AHIR {ECO:00002561HAMAP-Rule:M", XP93184519, retrieved from EBI accession No. Uniprot: A0A3N0AZJ3 Database accession No. A0A3N0AZJ3, 4 pages.

Database UniProt [Online] Jul. 24, 2013 (Jul. 24, 2013), "RecName: Full=Ketol-acid reductoisomerase (NADP(+)) {ECO:00002561 HAMAP-Rule:MF 00435}; Short=KARI {ECO:00002561HAMAPRule:MF 00435}; EC=1.1.1.86 {ECO:00002561HAMAP-Rule:MF_00435}; AltName: Full= Acetohydroxy-acid isomeroreductase {ECO:00002561 HAMAP-Rule:MF 00435}; Short=AHIR fECO:00002561HAMAP-Rule:M", XP93184203, retrieved from EBI accession No. UNIPROT:R6H831 Database accession No. R6H831, 3 pages.

Database UniProt [Online] Jul. 24, 2013 (Jul. 24, 2013), "RecName: Full=Ketol-acid reductoisomerase (NADP(+)) {ECO:00002561 HAMAP-Rule:MF 00435}; Short=KARI {ECO:00002561HAMAPRule: MF 00435}; EC=1.1.1.86 {ECO:0000256IHAMAP-Rule:MF_00435}; AltName: Full= Acetohydroxy-acid isomeroreductase {ECO:00002561 HAMAP-Rule:MF 00435}; Short=AHIR {ECO:0000256IHAMAP-Rule:M", XP93184171, retrieved from EBI accession No. UNIPROT:R7BNC8 Database accession No. R7BNC8, 3 pages.

Database UniProt [Online] Aug. 30, 2017 (Aug. 30, 2017), "RecName: Full=Ketol-acid reductoisomerase (NADP(+)) {ECO:00002561 HAMAP-Rule:MF_00435}; Short=KARI {ECO:0000256IHAMAPRule:MF_00435}; EC=1.1.1.86 {ECO:0000256IHAMAP-Rule:MF_00435}; AltName: Full= Acetohydroxy-acid isomeroreductase {ECO:0000256I HAMAP-Rule:MF 00435}; Short=AHIR {ECO:0000256IHAMAP-Rule:M", XP93184156, retrieved from EBI accession No. UNIPROT:A0A1Y4HP66 Database accession No. A0A1Y4HP66, 4 pages.

Database UniProt [Online] Mar. 4, 2015 (Mar. 4, 2015), "RecName: Full=Ketol-acid reductoisomerase (NADP(+)) {ECO:00002561 HAMAP-Rule:MF 00435}; Short=KARI {ECO:00002561HAMAPRule: MF 00435}; EC=1.1.1.86 {ECO:0000256IHAMAP-Rule:MF_00435}; AltName: Full= Acetohydroxy-acid isomeroreductase {ECO:00002561 HAMAP-Rule:MF 00435}; Short=AHIR {ECO:0000256IHAMAP-Rule:M", XP93184178, retrieved from EBI accession No. UNIPROT:A0A0B2AF51 Database accession No. A0A0B2AF51, 3 pages.

Database UniProt [Online] Nov. 7, 2018 (Nov. 7, 2018), "RecName: Full=Ketol-acid reductoisomerase (NADP(+)) {ECO:00002561 HAMAP-Rule:MF 00435}; Short=KARI {ECO:00002561HAMAPRule:MF 00435}; EC=1.1.1.86 {ECO:0000256IHAMAP-Rule:MF_00435}; AltName: Full= Acetohydroxy-acid isomeroreductase {ECO:00002561 HAMAP-Rule:MF 00435}; Short=AHIR {ECO:0000256IHAMAP-Rule:M", XP93184164, retrieved from EBI accession No. UNIPROT:A0A369LNQ2 Database accession No. A0A369LNQ2, 3 pages.

Extended European Search Report for European Application No. 21765419.3 mailed Jul. 24, 2024, 34 pages.

Alper, Hal, et al., "Engineering for biofuels: exploiting innate microbial capacity or importing biosynthetic potential?", Nature Reviews Microbiology (2009); 7(10): 715-723.

Atsumi, Shota, et al., "Non-fermentative pathways for synthesis of branched-chain higher alcohols as biofuels", Nature (2008); 451(7174): 86-89.

Barnett, James Arthur, et al., "Yeasts: characteristics and identification", Cambridge University Press (2000); 3: 28-29.

Becker, D. M., et al., "High-efficiency transformation of yeast by electroporation", Methods in Enzymology (1991); 194: 182-187.

Boeke, J. D., et al., "A positive selection for mutants lacking orotidine-5'-phosphate decarboxylase activity in yeast: 5-fluoro-orotic acid resistance", Molecular & General Genetics (1984); 197(2): 345-346.

Chipman, David, et al., "Biosynthesis of 2-aceto-2-hydroxy acids: acetolactate synthases and acetohydroxyacid synthases", Biochimica et Biophysica Acta (BBA)—Protein Structure and Molecular Enzymology (1998); 1385(2): 401-419.

Connor, Michael R., et al., "Engineering of an *Escherichia coli* strain for the production of 3-methyl-1-butanol", Applied and Environmental Microbiology (2008); 74(18): 5769-5775.

Dalphin, Mark E., et al., "TransTerm: a database of translational signals", Nucleic Acids Research (Jan. 1, 1996); 24(1): 216-218.

Dickinson, J. Richard, et al., "An investigation of the metabolism of valine to isobutyl alcohol in *Saccharomyces cerevisiae*", Journal of Biological Chemistry (1998); 273(40): 25751-25756.

Dujon, Bernard, et al., "Genome evolution in yeasts", Nature (2004); 430(6995): 35-44.

Gellissen, Gerd, et al., "Application of yeasts in gene expression studies: a comparison of *Saccharomyces cerevisiae*, Hansenula polymorpha and Kluyveromyces lactis—a review", Gene (1997); 190(1): 87-97.

GenBank Accession No. A0R480.1 "RecName: Full=Alpha-keto-acid decarboxylase; Short=KDC" created: May 20, 2008, sequence updated: Jan. 9, 2007, annotation updated: Apr. 7, 2021, 2 pages.

GenBank Accession No. AAB81248.1 "acetolactate synthase [Pyricularia grisea]", PLN Oct. 18, 1997, 2 pages.

GenBank Accession No. AAS49166.1 "branched-chain alpha-ketoacid decarboxylase [Lactococcus lactis]" BCT Dec. 27, 2004, 2 pages.

GenBank Accession No. ABX01060.1 "acetolactate synthase, large subunit, biosynthetic type [Methanococcus maripaludis C6]" BCT Feb. 10, 2014, 2 pages.

GenBank Accession No. CAA98646.1 "THI3 [*Saccharomyces cerevisiae*]" PLN Apr. 18, 2005, 2 pages.

GenBank Accession No. CAB91241.1 probable Alcohol Dehydrogenase I-ADH1 [Neurospora crassa] PLN Oct. 23, 2008, 2 pages.

GenBank Accession No. CBA03965.1 "alcohol dehydrogenase, zinc-containing [Neisseria meningitidis alpha275]" BCT May 28, 2012, 2 pages.

GenBank Accession No. EHA31115.1 "alcohol dehydrogenase [Bacillus subtilis subsp. subtilis str. SC-8]" BCT Oct. 13, 2011, 2 pages.

GenBank Accession No. NP_010668.1 Aro10p [*Saccharomyces cerevisiae* S288c] PLN Apr. 26, 2011, 2 pages.

GenBank Accession No. NP_012550.1 "dihydroxy-acid dehydratase ILV3 [*Saccharomyces cerevisiae* S288C]" PLN Aug. 3, 2021, 2 pages.

GenBank Accession No. NP_013826.1 "acetolactate synthase catalytic subunit [*Saccharomyces cerevisiae* S288C]" PLN Aug. 3, 2021, 2 pages.

(56)  References Cited

OTHER PUBLICATIONS

GenBank Accession No. NP_014051.1 "NADP-dependent alcohol dehydrogenase [*Saccharomyces cerevisiae* S288C]" PLN Aug. 3, 2021. 2 pages.
GenBank Accession No. NP_267340.1 "acetolactate synthase [*Lactococcus lactis* subsp. *lactis* Il1403]" CON Aug. 3, 2016, 2 pages.
GenBank Accession No. NP_267379.1 "dihydroxy-acid dehydratase [*Lactococcus lactis* subsp. *lactis* Il1403]" CON Aug. 3, 2016, 2 pages.
GenBank Accession No. NP_721805.1 "acetolactate synthase [*Streptococcus mutans* UA159]" CON May 21, 2017, 2 pages.
GenBank Accession No. NP_722414.1 "dihydroxy-acid dehydratase [*Streptococcus mutans* UA159]" CON May 21, 2017, 2 pages.
GenBank Accession No. NP_765765.1 "indole-3-pyruvate decarboxylase [*Staphylococcus epidermidis* ATCC 12228]" CON Aug. 3, 2016, 2 pages.
GenBank Accession No. O53865.1 "RecName: Full=Alpha-keto-acid decarboxylase; Short=KDC" created: May 20, 2008, sequence updated: Jun. 1, 1998, annotation updated: Feb. 19, 2014, 3 pages.
GenBank Accession No. P23234.1 "RecName: Full=Indole-3-pyruvate decarboxylase; Short=Indolepyruvate decarboxylase" created: Nov. 1, 1991, sequence updated: Nov. 1, 1991, annotation updated: Jun. 2, 2021, 4 pages.
GenBank Accession No. P42463.1 "RecName: Full=Acetolactate synthase large subunit; Short=AHAS; AltName: Full=Acetohydroxy-acid synthase large subunit; Short=ALS", created: Nov. 1, 1995, sequence updated: Nov. 1, 1995, annotation updated: Jun. 2, 2021, 3 pages.
GenBank Accession No. P51852.1 "RecName: Full=Indole-3-pyruvate decarboxylase; Short=Indolepyruvate decarboxylase" created: Oct. 1, 1996, sequence updated: Oct. 1, 1996, annotation updated: Jun. 2, 2021, 5 pages.
GenBank Accession No. Q04789.3 "RecName: Full=Acetolactate synthase; AltName: Full=ALS; AltName: Full=Acetohydroxy-acid synthase", created: Feb. 1, 1994, sequence updated: Jun. 16, 2009, annotation updated: Jun. 2, 2021, 3 pages.
GenBank Accession No. Q742Q2.1 "RecName: Full=Alpha-keto-acid decarboxylase; Short=KDC" created: May 20, 2008, sequence updated: Jul. 5, 2004, annotation updated: Jun. 2, 2021, 2 pages.
GenBank Accession No. XP_002485976.1 "acetolactate synthase, putative [Talaromyces stipitatus ATCC 10500]" PLN Jul. 2, 2009, 2 pages.
GenBank Accession No. XP_502180.2 "YALI0C23408p [Yarrowia lipolytica CLIB122]" PLN Jun. 6, 2017, 2 pages.
GenBank Accession No. XP_963045.1 "dihydroxy-acid dehydratase [Neurospora crassa OR74A]" PLN Oct. 11, 2017, 2 pages.
GenBank Accession No. YP_001035842.1 "alcohol dehydrogenase [*Streptococcus sanguinis* SK36]" CON Aug. 28, 2016, 2 pages.
GenBank Accession No. YP_001374103.1 "alcohol dehydrogenase [Bacillus cytotoxicus NVH 391-98]" CON Dec. 16, 2014, 2 pages.
GenBank Accession No. YP_002560734.1 "indole-3-pyruvate decarboxylase [Macrococcus caseolyticus JCSC5402]" CON Dec. 17, 2014, 2 pages.
GenBank Accession No. YP_003353820.1 "alpha-ketoisovalerate decarboxylase [*Lactococcus lactis* subsp. *lactis* KF147]" CON Dec. 17, 2014, 2 pages.
GenBank Accession No. YP_003354381 "alcohol dehydrogenase [*Lactococcus lactis* subsp. *lactis* KF147]" CON Dec. 17, 2014, 2 pages.
GenBank Accession No. YP_003561644.1 "indole-3-pyruvate decarboxylase [Bacillus megaterium QM B1551]" CON Dec. 17, 2014. 2 pages.
GenBank Accession No. YP_003613611.1 "acetolactate synthase [*Enterobacter cloacae* subsp. *cloacae* ATCC 13047]" CON Aug. 28, 2016, 2 pages.
GenBank Accession No. YP_004053736.1 "dihydroxy-acid dehydratase [Marivirga tractuosa DSM 4126]" CON Dec. 17, 2014, 2 pages.

GenBank Accession No. YP_026248.1 "dihydroxy-acid dehydratase [*Escherichia coli* str. K-12 substr. MG1655]" CON Apr. 29, 2021, 3 pages.
GenBank Accession No. YP_448586.1 "dihydroxy-acid dehydratase [Methanosphaera stadtmanae DSM 3091]" CON Dec. 17, 2014. 2 pages.
GenBank Accession No. YP_794451.1 "alcohol dehydrogenase [Lactobacillus brevis ATCC 367]" CON Feb. 23, 2015, 2 pages.
GenBank Accession No. YP_862145.1 "dihydroxy-acid dehydratase [Gramella forsetii KT0803]" CON Dec. 16, 2014, 2 pages.
GenBank Accession No. ZP_01890126.1 "dihydroxy-acid dehydratase [unidentified eubacterium SCB49]" ENV Apr. 8, 2013, 2 pages.
GenBank Accession No. ZP_04101989.1 Alcohol dehydrogenase 1 [Bacillus thuringiensis serovar berliner ATCC 10792] BCT Nov. 27, 2012, 2 pages.
GenBank Accession No. ZP_06014957.1 "acetolactate synthase [*Klebsiella pneumoniae* subsp. *rhinoscleromatis* ATCC 13884]" BCT Nov. 27, 2012, 2 pages.
GenBank Accession No. ZP_06197454.1 "alcohol dehydrogenase [Pediococcus acidilactici 7_4]" BCT Jun. 9, 2010. 2 pages.
Gietz, Daniel, et al., "Improved method for high efficiency transformation of intact yeast cells", Nucleic Acids Research (Mar. 25, 1992); 20(6): 1425.
Hugenholtz, Jeroen, et al., "Diacetyl production by different strains of *Lactococcus lactis* subsp. *lactis* var. *diacetylactis* and *Leuconostoc* spp.", Applied Microbiology and Biotechnology (1992); 38(1): 17-22.
International Application No. PCT/US2021/021096, International Search Report and Written Opinion, mailed Jul. 28, 2021, 11 pages.
International Application No. PCT/US2021/021096, Invitation to Pay Additional Fees, mailed May 10, 2021, 2 pages.
International Preliminary Report on Patentability for International Application No. PCT/US2021/021096, mailed on Sep. 15, 2022, 7 pages.
Ito, Hisao, et al., "Transformation of intact yeast cells treated with alkali cations", Journal of Bacteriology (Jan. 1983); 153(1): 163-168.
Kellis, M., et al., "Proof and evolutionary analysis of ancient genome duplication in the yeast *Saccharomyces cerevisiae*", Nature (2004); 428: 617-624.
Kooistra, Rolf, et al., "Efficient gene targeting in Kluyveromyces lactis", Yeast (2004); 21(9): 781-792.
Kurtzman, Cletus P., et al., "Phylogenetic relationships among species of *Saccharomyces, Schizosaccharomyces, Debaryomyces* and *Schwanniomyces* determined from partial ribosomal RNA sequences", Yeast (1991); 7(1): 61-72.
Langkjaer, Rikke B., et al., "Yeast genome duplication was followed by asynchronous differentiation of duplicated genes", Nature (2003); 421(6925): 848-852.
Masneuf, Isabelle, et al., "New hybrids between *Saccharomyces sensu stricto* yeast species found among wine and cider production strains", Applied and Environmental Microbiology (1998); 64(10): 3887-3892.
Mccourt, J. A., et al., "Acetohydroxyacid synthase and its role in the biosynthetic pathway for branched-chain amino acids." Amino Acids (2006); 31(2): 173-210.
Murray, Elizabeth E., et al., "Codon usage in plant genes", Nucleic Acids Research (Jan. 25, 1989); 17(2): 477-498.
Orr-Weaver, Terry L., et al., "Yeast transformation: a model system for the study of recombination", Proceedings of the National Academy of Sciences (1981); 78(10): 6354-6358.
Rainieri, Sandra, et al., "*Saccharomyces sensu stricto*: systematics, genetic diversity and evolution", Journal of Bioscience and Bioengineering (2003); 96(1): 1-9.
Wolfe, Kenneth H., et al., "Molecular evidence for an ancient duplication of the entire yeast genome", Nature (1997); 387(6634): 708-713.
Zhang, Kechun, et al., "Expanding metabolism for biosynthesis of nonnatural alcohols", Proceedings of the National Academy of Sciences (2008); 105(52): 20653-20658.

* cited by examiner

FIGURE 1 pyruvate

ALS $CO_2$ 2-acetolactate

NADH

NKR $NAD^+$ 2,3-dihydroxyisovalerate

DHAD 2-ketoisovalerate

KIVD $CO_2$ isobutyraldehyde

NADH

ADH $NAD^+$ isobutanol

FIGURE 2

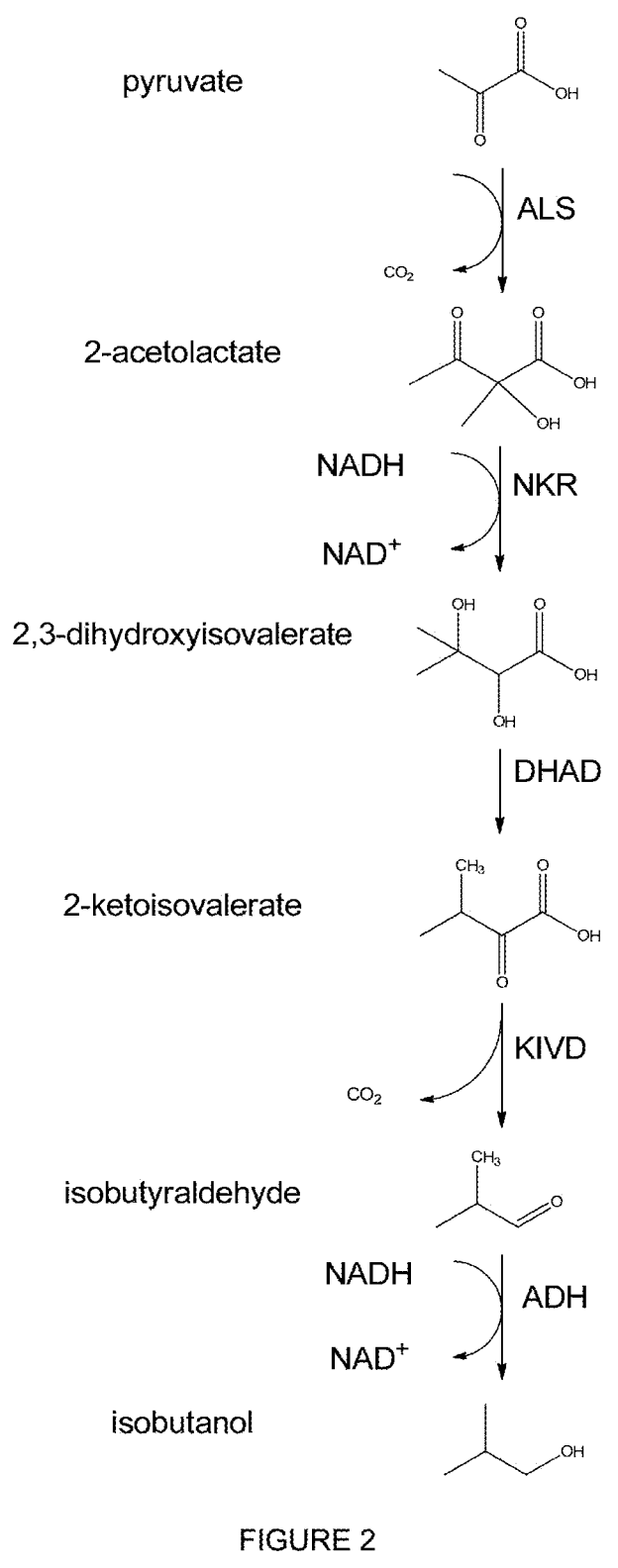

Gly31: 14 candidates picked for re-screening; 2 variants sequenced; 2 AA exchanges found; results of best performing variants displayed below:

Sequencing results:

Best variants: S148; Gly31Ala, S149; Gly31Cys

Met77: 27 candidates picked for re-screening; 6 variants sequenced; 3 AA exchanges found; results of best performing variants displayed below:

Sequencing results:

Exchanges found: Isoleucine (3), Valine (2), Leucine (1)

Best variant: S43: Met77Leu, S44: Met77Ile

Val91: 5 candidates picked for re-screening; 1 variant sequenced; 1 AA exchange found; results shown below:

Sequencing results:
Best variant: S50: Val9Ile

Lys290: 18 candidates picked for re-screening; 4 variants sequenced; 2 AA exchanges found; best performing variants displayed:

Sequencing results:
Exchanges found:
Arginine (2), Leucine (1), Alanine (1)

Best variant:
SB1: Lys290Ala
SB3: Lys290Leu

NKR VARIANTS FOR INCREASED PRODUCTION OF ISOBUTANOL

CROSS-REFERENCE TO RELATED APPLICATIONS

This application is a U.S. National Stage Application under 35 U.S.C. § 371 of International Application No. PCT/US2021/021096, filed Mar. 5, 2021, which claims priority to Provisional U.S. Application No. 62/986,378, filed Mar. 6, 2020, the contents of which are incorporated by reference in their entirety.

TECHNICAL FIELD

Recombinant microorganisms and methods of producing such microorganisms are provided. Also provided are methods of producing beneficial metabolites including fuels and chemicals by contacting a suitable substrate with the recombinant microorganisms of the invention and enzymatic preparations therefrom.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_114_01US_SeqList_ST25.txt, date recorded: Aug. 30, 2022, file size: 62.4 kilobytes).

BACKGROUND

The ability of microorganisms to convert sugars to beneficial metabolites including fuels, chemicals, and amino acids has been widely described in the literature in recent years. See, e.g., Alper et al., 2009, *Nature Microbiol. Rev.* 7: 715-723 and McCourt et al., 2006, *Amino Acids* 31: 173-210. Recombinant engineering techniques have enabled the creation of microorganisms that express biosynthetic pathways capable of producing a number of useful products, including the commodity chemical, isobutanol.

Isobutanol, also a promising biofuel candidate, has been produced in recombinant microorganisms expressing a heterologous, five-step metabolic pathway (See, e.g., WO/2007/050671 to Donaldson et al., WO/2008/098227 to Liao et al., and WO/2009/103533 to Festel et al.). However, the microorganisms produced to date have fallen short of commercial relevance due to their low performance characteristics, including, for example low productivities, low titers, and low yields.

The second step of the isobutanol producing metabolic pathway is catalyzed by ketol-acid reductoisomerase (KARI), which converts acetolactate to 2,3-dihydroxyisovalerate. The present inventors have observed that KARI enzymes currently being used in isobutanol-producing recombinant microorganisms suffer from product inhibition (i.e., inhibition by 2,3-dihydroxyisovalerate), resulting in low isobutanol productivity. To overcome this problem and thereby improve isobutanol production, the present inventors have identified a group of KARI enzymes exhibiting reduced inhibition by 2,3-dihydroxyisovalerate. Accordingly, this application describes methods of increasing isobutanol production through the use of recombinant microorganisms comprising KARI enzymes with improved properties for the production of isobutanol.

One KARI enzyme of particular interest identified herein that exhibits reduced product inhibition is the *S. exigua* KARI enzyme (SEQ ID NO: 2). The present inventors have found that the use of the *S. exigua* KARI enzyme in an isobutanol pathway may lead to improved isobutanol yields, titers, and productivity.

Another important feature of a KARI enzyme is the ability to use NADH as a cofactor for the conversion of acetolactate to 2,3-dihydroxyisovalerate. The present inventors have found that when an NADH-dependent KARI is used in conjunction with an NADH-dependent alcohol dehydrogenase (ADH), isobutanol can be produced at theoretical yield and/or under anaerobic conditions. See, e.g., US Publication No. US 2010/0143997 the contents of which are incorporated by reference it their entirety for all purposes. Because NADH-dependence is an important feature of a KARI enzyme, the present inventors have identified several beneficial mutations which can be made to the *S. exigua* KARI enzyme to switch the cofactor specificity of the enzyme from NADPH to NADH.

SUMMARY OF THE INVENTION

The second step of the isobutanol producing metabolic pathway is catalyzed by ketol-acid reductoisomerase (KARI), which converts acetolactate to 2,3-dihydroxyisovalerate. However, KARI enzymes currently being used in isobutanol-producing recombinant microorganisms suffer from product inhibition (i.e., inhibition by 2,3-dihydroxyisovalerate), resulting in low isobutanol productivity. To overcome this problem and thereby improve isobutanol production, the present inventors have identified a group of KARI enzymes exhibiting reduced inhibition by 2,3-dihydroxyisovalerate. Accordingly, this application describes methods of increasing isobutanol production through the use of recombinant microorganisms comprising KARI enzymes with improved properties for the production of isobutanol.

One KARI enzyme of particular interest identified herein that exhibits reduced product inhibition is the *S. exigua* KARI enzyme (SEQ ID NO: 2). The present inventors have found that the use of the *S. exigua* KARI enzyme in an isobutanol pathway may lead to improved isobutanol yields, titers, and productivity.

Another important feature of a KARI enzyme is the ability to use NADH as a cofactor for the conversion of acetolactate to 2,3-dihydroxyisovalerate. The present inventors have found that when an NADH-dependent KARI is used in conjunction with an NADH-dependent alcohol dehydrogenase (ADH), isobutanol can be produced at theoretical yield and/or under anaerobic conditions. See, e.g., US Publication No. US 2010/0143997 the contents of which are incorporated by reference it their entirety for all purposes. Because NADH-dependence is an important feature of a KARI enzyme, the present inventors have identified several beneficial mutations which can be made to the *S. exigua* KARI enzyme to switch the cofactor specificity of the enzyme from NADPH to NADH.

The present disclosure provides a group of KARI enzymes with reduced inhibition by 2,3-dihydroxyisovalerate. The use of one or more of these KARI enzymes, or NADH-dependent variants thereof, can improve production of the isobutanol.

In a first aspect, the application relates to a recombinant microorganism comprising at least one nucleic acid molecule encoding a ketol-acid reductoisomerase (KARI), wherein said KARI is at least about 60% identical to SEQ ID NO: 2 and/or SEQ ID NO: 12 In some embodiments, the KARI is derived from the genus *Slackia*. In some embodiments, the KARI is derived from *Slackia exigua*. In another specific embodiment, the KARI is encoded by SEQ ID NO: 1. In some embodiments, the KARI is derived from the genus *Cryptobacterium*. In a specific embodiment, the KARI is derived from *Cryptobacterium curtum*. In another specific embodiment, the KARI is encoded by SEQ ID NO: 3. In yet some embodiments, the KARI is derived from the genus *Eggerthella*. In a specific embodiment, the KARI is derived from *Eggerthella lenta*. In another specific embodiment, the KARI is encoded by SEQ ID NO: 5, SEQ ID NO: 7, SEQ ID NO: 9, SEQ ID NO: 91, SEQ ID NO: 93, or SEQ ID NO: 95.

In some embodiments, the KARI utilizes NADH rather than NADPH. In some embodiments, the present disclosure provides a NADH-dependent ketol-acid reductoisomerases (NKRs) derived from a KARI that is at least about 60% identical to SEQ ID NO: 2 and/or SEQ ID NO: 12. Thus, in some embodiments, the present application relates to a recombinant microorganism comprising a NKR derived from a KARI that is at least about 60% identical to SEQ ID NO: 2 and/or SEQ ID NO: 12.

In some embodiments, the novel NKR of the present disclosure shows greater specific activity compared to the NKR of SEQ ID NO: 2 and/or SEQ ID NO: 12. In some embodiments, the novel NKR of the present disclosure shows improved product inhibition compared to the NKR of SEQ ID NO: 2 and/or SEQ ID NO: 12. In some embodiments, the novel NKR of the present disclosure shows greater specific activity and improved product inhibition compared to the NKR of SEQ ID NO: 2 and/or SEQ ID NO: 12.

Examples of NKRs provided by the instant disclosure include enzymes having one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

In some embodiments, the KARI enzyme contains two or more modifications or mutations at the amino acids corresponding to the positions described above. In some embodiments, the KARI enzyme contains three or more modifications or mutations at the amino acids corresponding to the positions described above. In yet some embodiments, the KARI enzyme contains four or more modifications or mutations at the amino acids corresponding to the positions described above. In yet some embodiments, the KARI enzyme contains five or more modifications or mutations at the amino acids corresponding to the positions described above. In yet some embodiments, the KARI enzyme contains six or more modifications or mutations at the amino acids corresponding to the positions described above. In yet some embodiments, the KARI enzyme contains seven or more modifications or mutations at the amino acids corresponding to the positions described above. In yet some embodiments, the KARI enzyme contains eight modifications or mutations at the amino acids corresponding to the positions described above. In yet some embodiments, the KARI enzyme contains nine modifications or mutations at the amino acids corresponding to the positions described above.

Further included within the scope of the application are novel modified or mutated NKR enzymes, other than the *S. exigua* KARI (Se1_NKR) (SEQ ID NO: 2), which contain modifications or mutations corresponding to those set out above.

In various embodiments described herein, the modified or mutated NKR enzymes may exhibit an increased catalytic efficiency with NADH as compared to the wild-type KARI. In some embodiments, the modified or mutated NKR enzymes of the present disclosure exhibit an increased catalytic efficiency with NADH of about 1% to about 10000% as compared to the wild-type KARI. In some embodiments, the KARI has at least about a 5% increased catalytic efficiency with NADH as compared to the wild-type KARI. In some embodiments, the KARI has at least about a 25%, at least about a 50%, at least about a 75%, at least about a 100%, at least about a 500%, at least about 1000%, or at least about a 10000% increased catalytic efficiency with NADH as compared to the wild-type KARI.

In various embodiments described herein, the modified or mutated KARI (NKR) may exhibit a decreased Michaelis Menten constant ($K_M$) for NADH as compared to the wild-type KARI. In some embodiments, the modified or mutated NKR enzymes of the present disclosure exhibit a decreased Michaelis Menten constant ($K_M$) for NADH of about 1% to about 100% as compared to the wild-type KARI. In some embodiments, the KARI has at least about a 5% decreased $K_M$ for NADH as compared to the wild-type KARI. In some embodiments, the KARI has at least about a 25%, at least about a 50%, at least about a 75%, at least about a 90%, at least about a 95%, or at least about a 97.5% decreased $K_M$ for NADH as compared to the wild-type KARI.

In various embodiments described herein, the modified or mutated KARI (NKR) may exhibit an increased catalytic constant ($k_{cat}$) with NADH as compared to the wild-type KARI. In some embodiments, the modified or mutated KARI (NKR) exhibits an increased catalytic constant ($k_{cat}$) with NADH of about 1% to about 1000% as compared to the wild-type KARI. In some embodiments, the KARI has at least about a 5% increased $k_{cat}$ with NADH as compared to the wild-type KARI. In some embodiments, the KARI has at least about a 25%, at least about a 50%, at least about a 75%, at least about 100%, at least about 200%, or at least about a 500% increased $k_{cat}$ with NADH as compared to the wild-type KARI.

In various embodiments described herein, the modified or mutated KARI may exhibit an increased Michaelis Menten constant ($K_M$) for NADPH as compared to the wild-type KARI. In some embodiments, the modified or mutated KARI (NKR) exhibits an increased Michaelis Menten constant ($K_M$) for NADPH of about 1% to about 10,000% as compared to the wild-type KARI. In some embodiments, the KARI has at least about a 5% increased $K_M$ for NADPH as compared to the wild-type KARI. In other embodiments, the KARI has at least about a 25%, at least about a 50%, at least about a 100%, at least about a 500%, at least about a 1000%, or at least about a 5000% increased $K_M$ for NADPH as compared to the wild-type KARI.

In various embodiments described herein, the modified or mutated KARI may exhibit a decreased catalytic constant ($k_{cat}$) with NADPH as compared to the wild-type KARI. In some embodiments, the modified or mutated KARI (NKR) exhibits an increased Michaelis Menten constant ($K_M$) for NADP decreased catalytic constant ($k_{cat}$) with NADPH of about 1% to about 100% as compared to the wild-type KARI. In some embodiments, the KARI has at least about a 5% decreased $k_{cat}$ with NADPH as compared to the wild-type KARI. In other embodiments, the KARI has at least about a 25%, at least about a 50%, or at least about a 75%, at least about 90% decreased $k_{cat}$ with NADPH as compared to the wild-type KARI.

In some embodiments described herein, the catalytic efficiency of the modified or mutated KARI with NADH is increased with respect to the catalytic efficiency with NADPH of the wild-type KARI. In some embodiments, the catalytic efficiency of the modified or mutated KARI with NADH is increased with respect to the catalytic efficiency with NADPH by about 1% to about 100% as compared to the wild-type KARI. In some embodiments, the catalytic efficiency of said KARI with NADH is at least about 10% of the catalytic efficiency with NADPH of the wild-type KARI. In some embodiments, the catalytic efficiency of said KARI with NADH is at least about 25%, at least about 50%, or at least about 75% of the catalytic efficiency with NADPH of the wild-type KARI. In some embodiments, the modified or mutated KARI preferentially utilizes NADH rather than NADPH.

In some embodiments, the application is directed to NADH-dependent KARI enzymes having a catalytic efficiency with NADH that is greater than the catalytic efficiency with NADPH. In some embodiments, the catalytic efficiency of the modified or mutated KARI with NADH is increased with respect to the catalytic efficiency with NADPH by about 1-fold to about 1000-fold as compared to the wild-type KARI. In some embodiments, the catalytic efficiency of the NADH-dependent KARI is at least about 2-fold greater with NADH than with NADPH. In other embodiments, the catalytic efficiency of the NADH-dependent KARI is at least about 4-fold, at least about 5-fold, at least about 6-fold, at least about 7-fold, at least about 8-fold, at least about 9-fold, at least about 10-fold, at least about 25-fold, at least about 50-fold, at least about 100-fold, or at least about 500-fold greater with NADH than with NADPH.

In some embodiments, the application is directed to modified or mutated KARI enzymes that demonstrate a switch in cofactor specificity from NADPH to NADH. In some embodiments, the modified or mutated KARI has about a 1:1 ratio to about a 100:1 ratio of catalytic efficiency ($k_{cat}/K_M$) with NADH over $k_{cat}$ with NADPH. In some embodiments, the modified or mutated KARI has at least about a 2:1 ratio of catalytic efficiency ($k_{cat}/K_M$) with NADH over $k_{cat}$ with NADPH. In other embodiments, the modified or mutated KARI has at least about a 10:1 ratio of catalytic efficiency ($k_{cat}/K_M$) with NADH over catalytic efficiency ($k_{cat}/K_M$) with NADPH.

In some embodiments, the modified or mutated KARI exhibits at least about a 1:10 ratio of $K_M$ for NADH over $K_M$ for NADPH.

In additional embodiments, the application is directed to modified or mutated KARI enzymes that have been codon optimized for expression in certain desirable host organisms, such as yeast and *E. coli*.

In another aspect, the application relates to a recombinant microorganism comprising at least one nucleic acid molecule encoding a mutated or modified KARI (NKR) enzyme, wherein said mutated or modified KARI (NKR) enzyme has one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO:

2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2). Further included within the scope of the application are recombinant microorganisms comprising a KARI enzyme, other than the *S. exigua* KARI (SEQ ID NO: 2), which contains modifications or mutations at positions corresponding to those set out above.

In various embodiments described in the application, the recombinant microorganism comprises an isobutanol producing metabolic pathway. In some embodiments, the isobutanol producing metabolic pathway comprises at least one exogenous gene encoding a polypeptide that catalyzes a step in the conversion of pyruvate to isobutanol. In some embodiments, the isobutanol producing metabolic pathway comprises at least two exogenous genes encoding polypeptides that catalyze steps in the conversion of pyruvate to isobutanol. In yet some embodiments, the isobutanol producing metabolic pathway comprises at least three exogenous genes encoding polypeptides that catalyze steps in the conversion of pyruvate to isobutanol. In yet some embodiments, the isobutanol producing metabolic pathway comprises at least four exogenous genes encoding polypeptides that catalyze steps in the conversion of pyruvate to isobutanol. In yet some embodiments, the isobutanol producing metabolic pathway comprises at least five exogenous genes encoding polypeptides that catalyze steps in the conversion of pyruvate to isobutanol. In yet some embodiments, all of the isobutanol producing metabolic pathway steps in the conversion of pyruvate to isobutanol are converted by exogenously encoded enzymes. In an exemplary embodiment, at least one of the exogenously encoded enzymes is a KARI that is at least about 60% identical to SEQ ID NO: 2 and/or SEQ ID NO: 12. In another exemplary embodiment, at least one of the exogenously encoded enzymes is a KARI enzyme has one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

In some embodiments, one or more of the isobutanol pathway genes encodes an enzyme that is localized to the cytosol. In some embodiments, the recombinant microorganisms comprise an isobutanol producing metabolic pathway with at least one isobutanol pathway enzyme localized in the cytosol. In some embodiments, the recombinant microorganisms comprise an isobutanol producing metabolic pathway with at least two isobutanol pathway enzymes localized in the cytosol. In yet some embodiments, the recombinant microorganisms comprise an isobutanol producing metabolic pathway with at least three isobutanol pathway enzymes localized in the cytosol. In yet some embodiments, the recombinant microorganisms comprise an isobutanol producing metabolic pathway with at least four isobutanol pathway enzymes localized in the cytosol. In an exemplary embodiment, the recombinant microorganisms comprise an isobutanol producing metabolic pathway with five isobutanol pathway enzymes localized in the cytosol. In yet another exemplary embodiment, the recombinant microorganisms comprise an isobutanol producing metabolic pathway with all isobutanol pathway enzymes localized in the cytosol.

In various embodiments described herein, the isobutanol pathway genes may encode enzyme(s) selected from the group consisting of acetolactate synthase (ALS), ketol-acid reductoisomerase (KARI), dihydroxyacid dehydratase (DHAD), 2-keto-acid decarboxylase, e.g., keto-isovalerate decarboxylase (KIVD), and alcohol dehydrogenase (ADH). In some embodiments, the KARI is an NADH-dependent KARI (NKR). In some embodiments, the ADH is an NADH-dependent ADH. In yet some embodiments, the KARI is an NADH-dependent KARI (NKR) and the ADH is an NADH-dependent ADH. In an exemplary embodiment, the KARI is at least about 60% identical to SEQ ID NO: 2 and/or SEQ ID NO: 12. In another exemplary embodiment, the KARI comprises one or more modifications or mutations at positions corresponding to amino acids selected from: (a) glycine 31 of the *S. exigua* KARI (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

In various embodiments described herein, the recombinant microorganisms of the invention that comprise an isobutanol producing metabolic pathway may be further engineered to reduce or eliminate the expression or activity of one or more enzymes selected from a pyruvate decarboxylase (PDC), a glycerol-3-phosphate dehydrogenase (GPD), a 3-keto acid reductase (3-KAR), or an aldehyde dehydrogenase (ALDH).

In various embodiments described herein, the recombinant microorganisms may be recombinant yeast microorganisms. In some embodiments, the recombinant yeast microorganisms may be members of the *Saccharomyces* clade, *Saccharomyces sensu stricto* microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces sensu stricto* microorganisms. In some embodiments, the *Saccharomyces sensu stricto* is selected from the group consisting of *S. cerevisiae, S. kudriavzevii, S. mikatae, S. bayanus, S. uvarum, S. carocanis* and hybrids thereof.

In some embodiments, the recombinant microorganisms may be Crabtree-negative recombinant yeast microorganisms. In some embodiments, the Crabtree-negative yeast microorganism is classified into a genera selected from the group consisting of *Saccharomyces, Kluyveromyces, Pichia,*

*Issatchenkia, Hansenula,* or *Candida.* In additional embodiments, the Crabtree-negative yeast microorganism is selected from *Saccharomyces kluyveri, Kluyveromyces lactis, Kluyveromyces marxianus, Pichia anomala, Pichia stipitis, Hansenula anomala, Candida utilis* and *Kluyveromyces waltii.*

In some embodiments, the recombinant microorganisms may be Crabtree-positive recombinant yeast microorganisms. In some embodiments, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces.* In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Kluyveromyces thermotolerans, Candida glabrata, Z. bailli, Z. rouxii, Debaryomyces hansenii, Pichia pastorius, Schizosaccharomyces pombe,* and *Saccharomyces uvarum.*

In some embodiments, the recombinant microorganisms may be post-WGD (whole genome duplication) yeast recombinant microorganisms. In some embodiments, the post-WGD yeast recombinant microorganism is classified into a genera selected from the group consisting of *Saccharomyces* or *Candida.* In additional embodiments, the post-WGD yeast is selected from the group consisting of *Saccharomyces cerevisiae, Saccharomyces uvarum, Saccharomyces bayanus, Saccharomyces paradoxus, Saccharomyces castelli,* and *Candida glabrata.*

In some embodiments, the recombinant microorganisms may be pre-WGD (whole genome duplication) yeast recombinant microorganisms. In some embodiments, the pre-WGD yeast recombinant microorganism is classified into a genera selected from the group consisting of *Saccharomyces, Kluyveromyces, Candida, Pichia, Issatchenkia, Debaryomyces, Hansenula, Pachysolen, Yarrowia* and *Schizosaccharomyces.* In additional embodiments, the pre-WGD yeast is selected from the group consisting of *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Issatchenkia orientalis, Issatchenkia occidentalis, Debaryomyces hansenii, Hansenula anomala, Pachysolen tannophilis, Yarrowia hpolytica,* and *Schizosaccharomyces pombe.*

In some embodiments, the recombinant microorganisms may be microorganisms that are non-fermenting yeast microorganisms, including, but not limited to those, classified into a genera selected from the group consisting of Tricosporon, *Rhodotorula, Myxozyma,* or *Candida.* In a specific embodiment, the non-fermenting yeast is *C. xestobii.*

In another aspect, the present invention provides methods of producing isobutanol using a recombinant microorganism as described herein. In some embodiments, the method includes cultivating the recombinant microorganism in a culture medium containing a feedstock providing the carbon source until a recoverable quantity of isobutanol is produced and optionally, recovering the isobutanol. In some embodiments, the microorganism produces isobutanol from a carbon source at a yield of at least about 5 percent theoretical. In some embodiments, the microorganism produces isobutanol at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, or at least about 97.5 percent theoretical.

In some embodiments, the recombinant microorganism converts the carbon source to isobutanol under aerobic conditions. In some embodiments, the recombinant microorganism converts the carbon source to isobutanol under microaerobic conditions. In yet some embodiments, the recombinant microorganism converts the carbon source to isobutanol under anaerobic conditions.

BRIEF DESCRIPTION OF DRAWINGS

Illustrative embodiments of the invention are illustrated in the drawings, in which:

Figure 1:
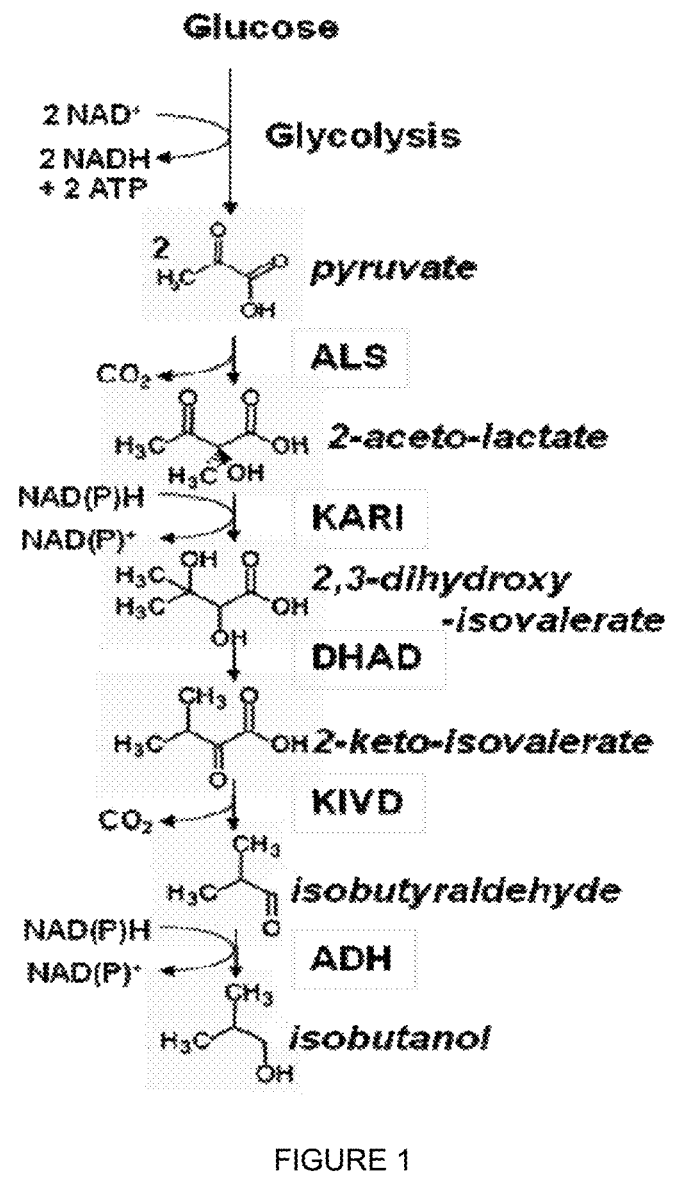

FIG. 1 illustrates an exemplary embodiment of an isobutanol pathway.

FIG. 2 illustrates an exemplary embodiment of an NADH-dependent isobutanol pathway.

DETAILED DESCRIPTION

Figure 3:
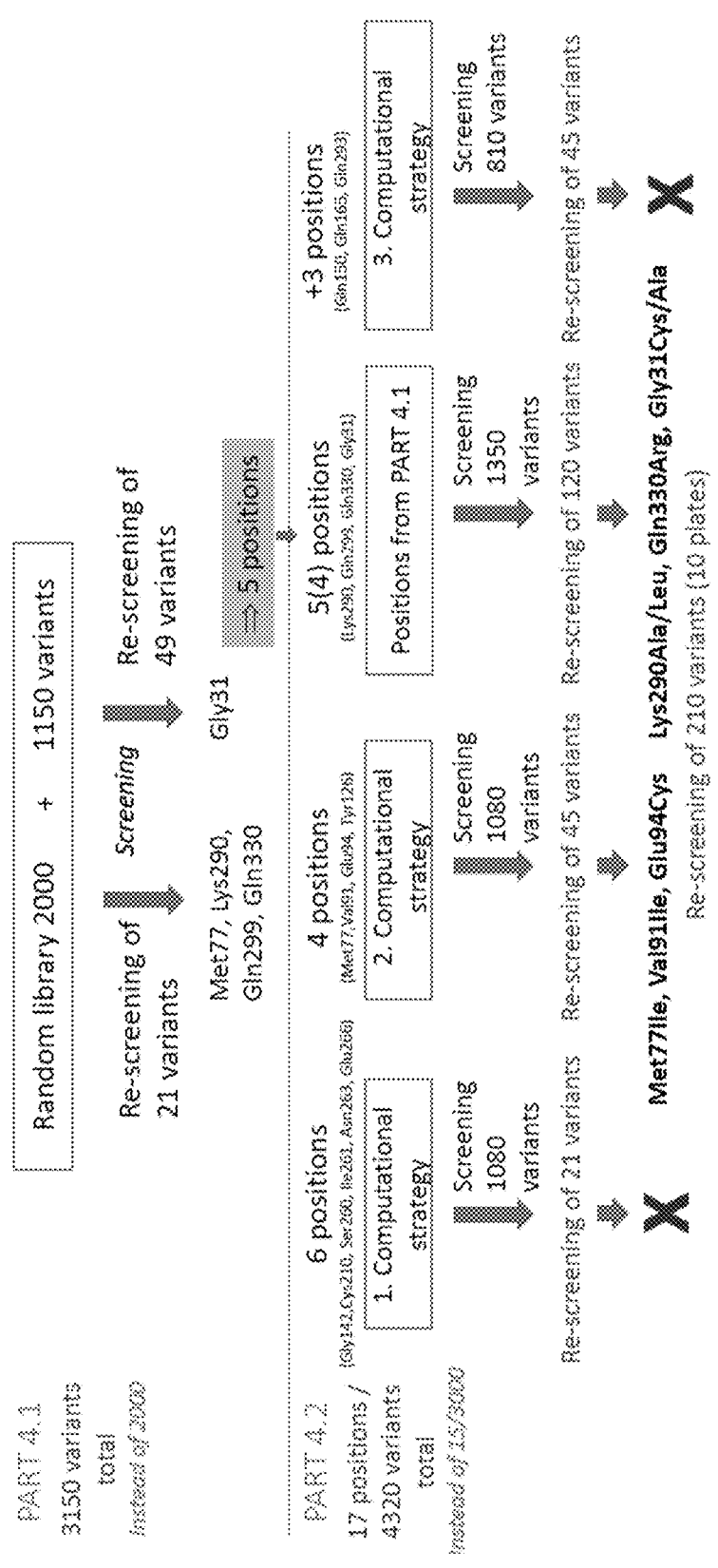
FIG. 3 illustrates a summary of the NKR mutation and screening strategy described herein.
Figure 4:
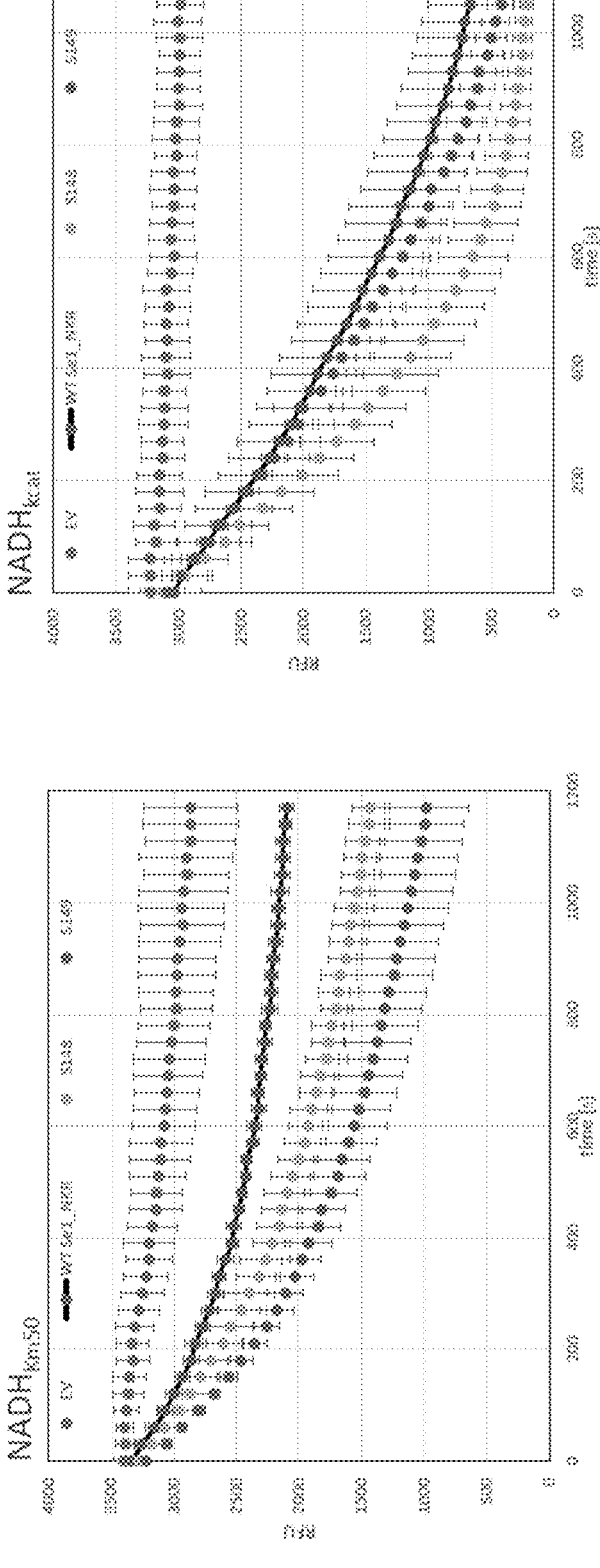
FIG. 4 illustrates the $NADH_{Km50}$ and $NADH_{Kcat}$ of Se1_NKR variants containing substitutions at glycine 31.
Figure 5:
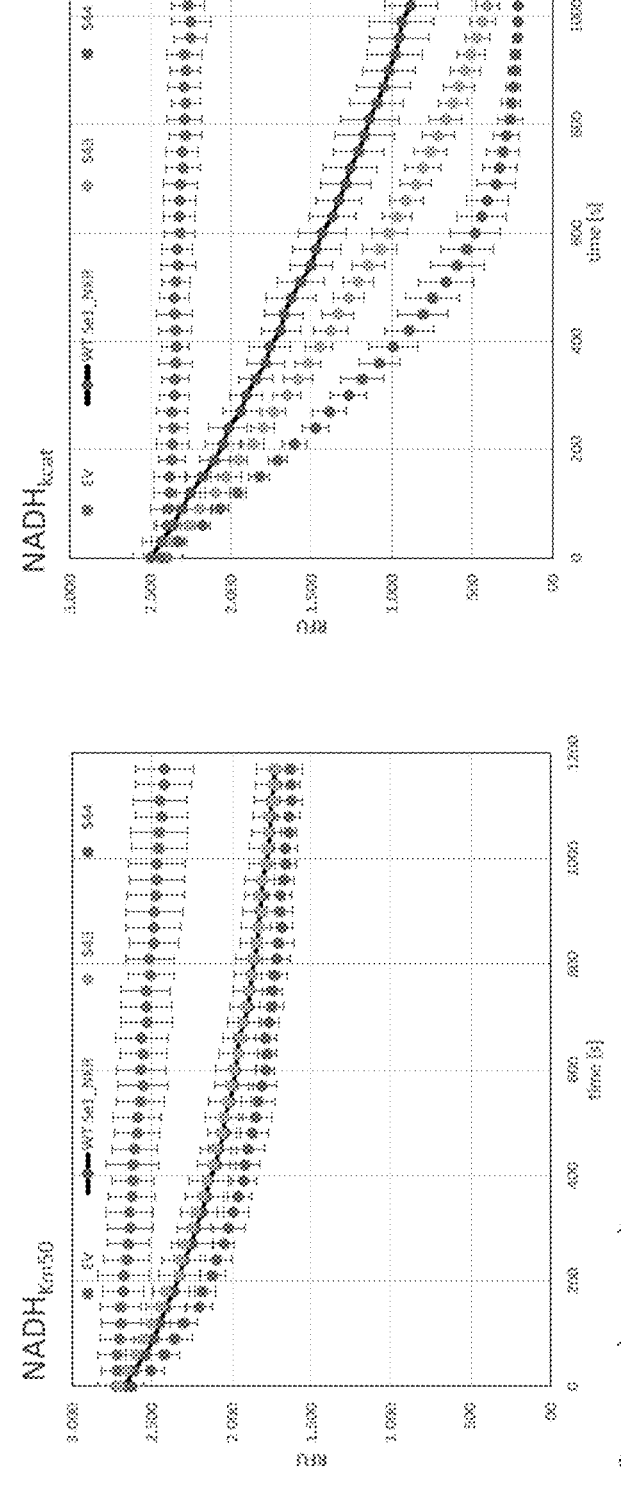
FIG. 5 illustrates the $NADH_{Km50}$ and $NADH_{Kcat}$ of Se1_NKR variants containing substitutions at methionine 77.
Figure 6:
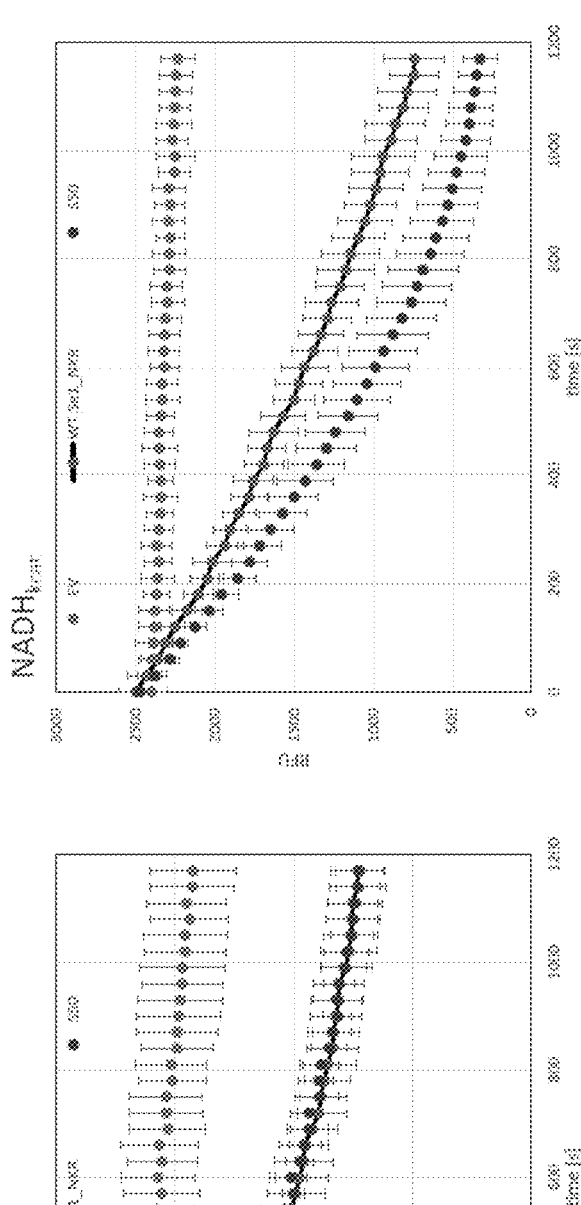
FIG. 6 illustrates the $NADH_{Km50}$ and $NADH_{Kcat}$ of the Se1_NKR variants containing substitutions at valine 91.
Figure 7:
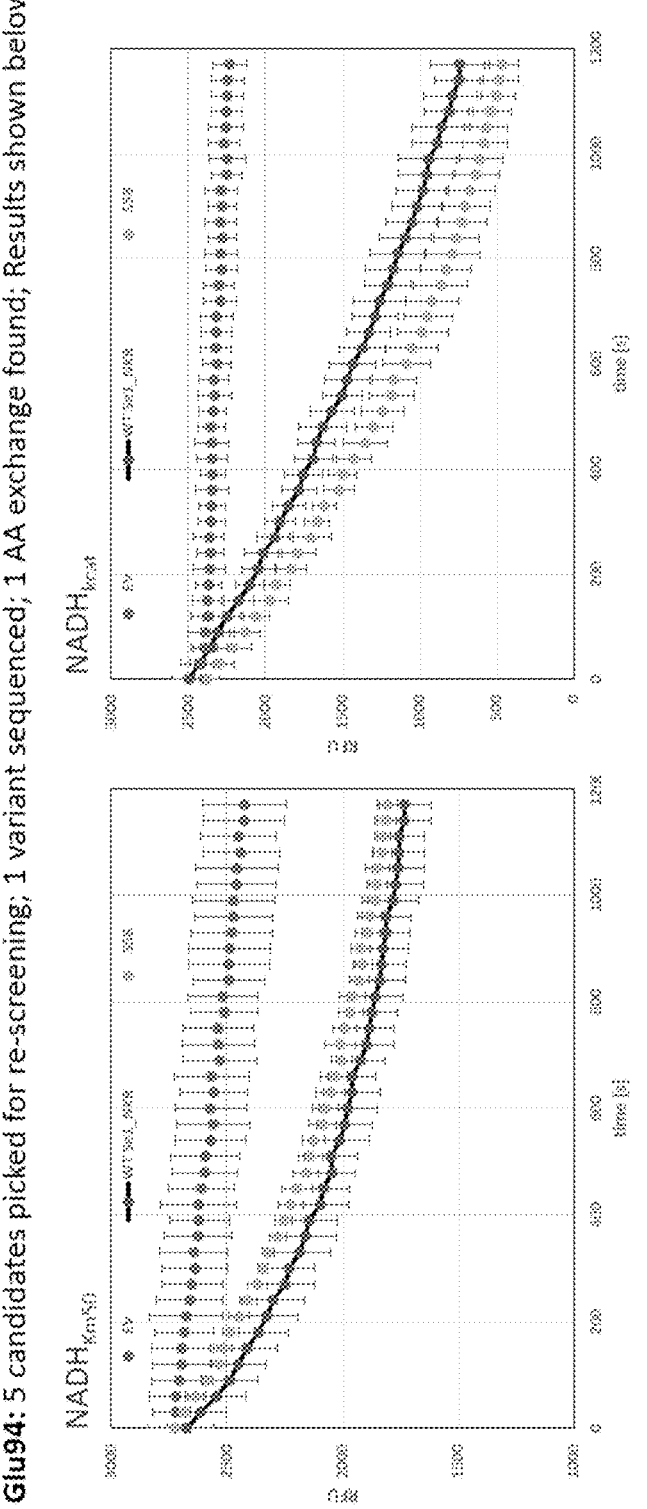
FIG. 7 illustrates the $NADH_{Km50}$ and $NADH_{Kcat}$ of the Se1_NKR variants containing substitutions at glutamic acid 94.
Figure 8:
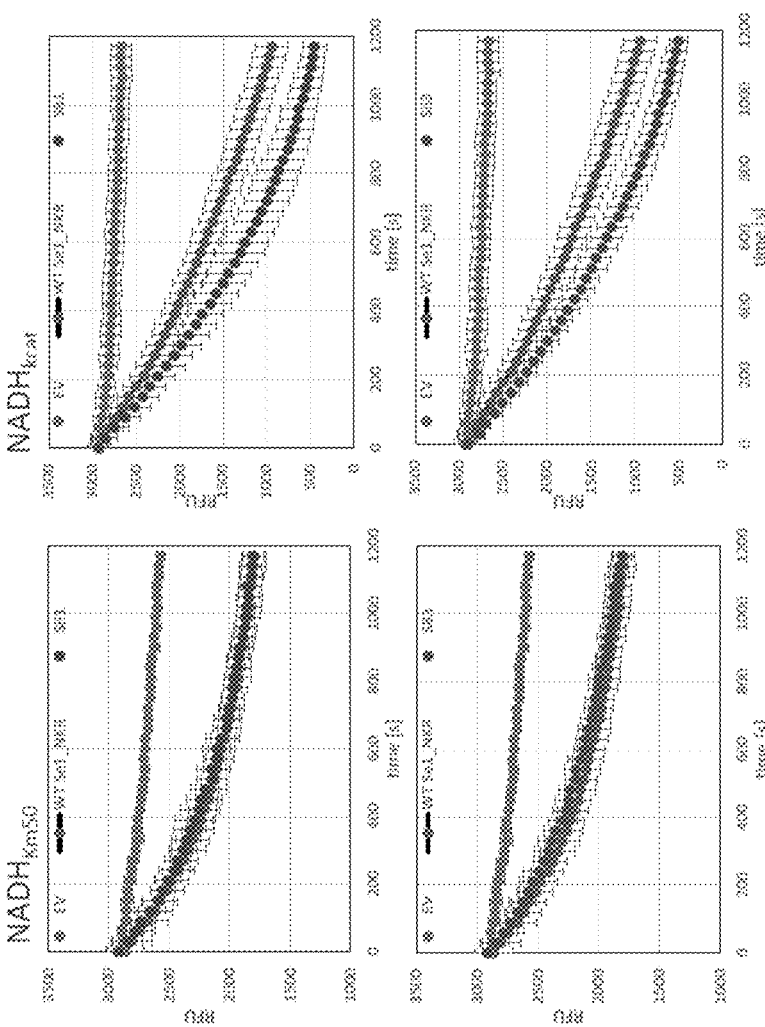
FIG. 8 illustrates the $NADH_{Km50}$ and $NADH_{Kcat}$ of the Se1_NKR variants containing substitutions at lysine 290.
Figure 9:
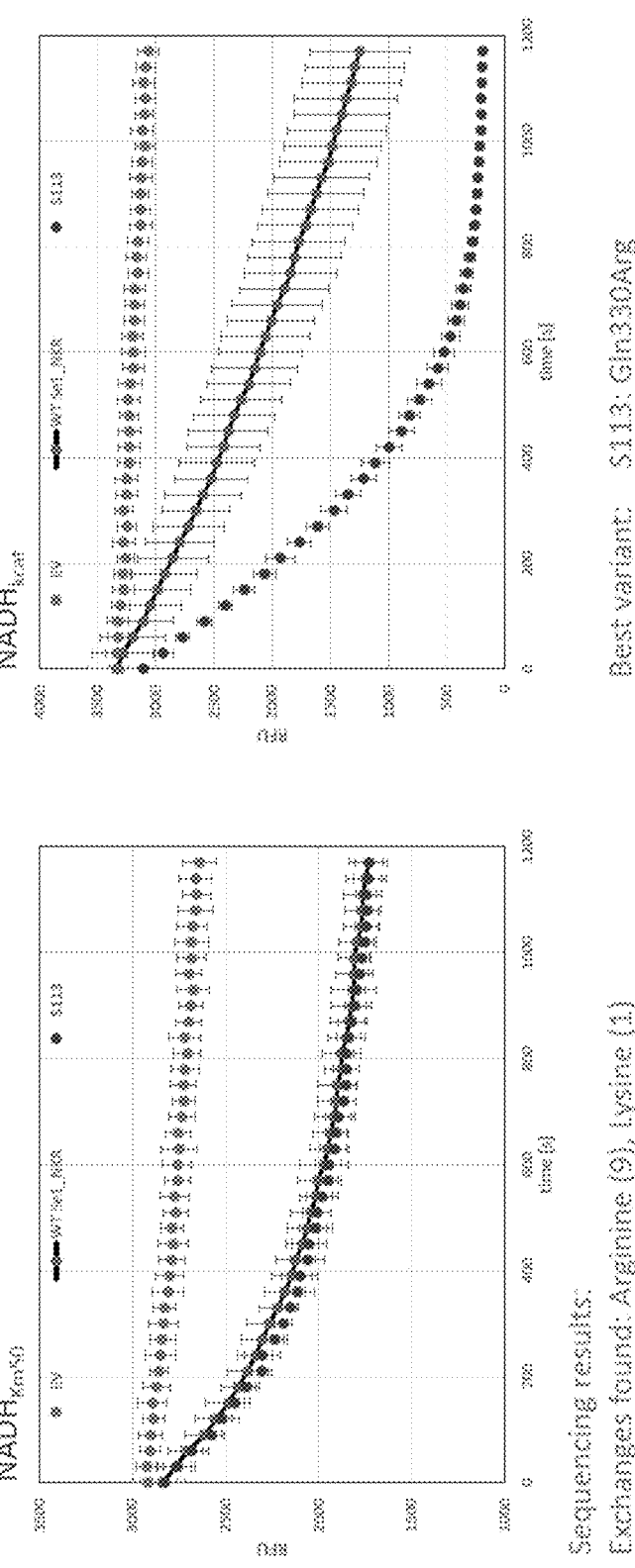
FIG. 9 illustrates the $NADH_{Km50}$ and $NADH_{Kcat}$ of the Se1_NKR variants containing substitutions at glutamic acid 330.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophiles (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consist mainly of hyperthermophilic sulfur-dependent prokaryotes and the Euryarchaeota contain the methanogens and extreme halophiles.

"Bacteria", or "eubacteria", refers to a domain of prokaryotic organisms. Bacteria include at least eleven distinct groups as follows: (1) Gram-positive (gram+) bacteria, of which there are two major subdivisions: (1) high G-FC group (Actinomycetes, Mycobacteria, *Micrococcus*, others) (2) low G-FC group (*Bacillus, Clostridia, Lactobacillus,* Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007) The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The terms "recombinant microorganism," "modified microorganism," and "recombinant host cell" are used interchangeably herein and refer to microorganisms that have been genetically modified to express or to overexpress endogenous polynucleotides, to express heterologous polynucleotides, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

As used herein and as would be understood by one of ordinary skill in the art, "reduced activity and/or expression" of a protein such as an enzyme can mean either a reduced specific catalytic activity of the protein (e.g. reduced activity) and/or decreased concentrations of the protein in the cell (e.g. reduced expression). As would be understood by one or ordinary skill in the art, the reduced activity of a protein in a cell may result from decreased concentrations of the protein in the cell.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism The term "engineer" refers to any manipulation of a microorganism that results in a detectable change in the microorganism, wherein the manipulation includes but is not limited to inserting a polynucleotide and/or polypeptide heterologous to the microorganism and mutating a polynucleotide and/or polypeptide native to the microorganism.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, a nonsense mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are identified and/or enriched through artificial selection pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

As used herein, the term "isobutanol producing metabolic pathway" refers to an enzyme pathway which produces isobutanol from pyruvate.

The term "NADH-dependent" as used herein with reference to an enzyme, e.g., KARI and/or ADH, refers to an enzyme that catalyzes the reduction of a substrate coupled to the oxidation of NADH with a catalytic efficiency that is greater than the reduction of the same substrate coupled to the oxidation of NADPH at equal substrate and cofactor concentrations.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a recombinant microorganism as described herein.

The term "fermentation" or "fermentation process" is defined as a process in which a microorganism is cultivated in a culture medium containing raw materials, such as feedstock and nutrients, wherein the microorganism converts raw materials, such as a feedstock, into products.

The term "volumetric productivity" or "production rate" is defined as the amount of product formed per volume of medium per unit of time. Volumetric productivity is reported in gram per liter per hour (g/L/h).

The term "specific productivity" or "specific production rate" is defined as the amount of product formed per volume of medium per unit of time per amount of cells. Specific productivity is reported in gram (or milligram) per gram cell dry weight per hour (g/g h).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

"Aerobic conditions" are defined as conditions under which the oxygen concentration in the fermentation medium is sufficiently high for an aerobic or facultative anaerobic microorganism to use as a terminal electron acceptor.

In contrast, "anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. Methods for the production of isobutanol under anaerobic conditions are described in commonly owned and co-pending publication, US 2010/0143997, the disclosures of which are herein incorporated by reference in its entirety for all purposes.

"Aerobic metabolism" refers to a biochemical process in which oxygen is used as a terminal electron acceptor to make energy, typically in the form of ATP, from carbohydrates. Aerobic metabolism occurs, e.g., via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to pyruvate, yielding ethanol. Fermentative pathways are usually active under anaerobic conditions but may also occur under aerobic conditions, under conditions where NADH is not fully oxidized via the respiratory chain.

For example, above certain glucose concentrations, Crabtree positive yeasts produce large amounts of ethanol under aerobic conditions.

The term "byproduct" or "by-product" means an undesired product related to the production of an amino acid, amino acid precursor, chemical, chemical precursor, biofuel, biofuel precursor, higher alcohol, or higher alcohol precursor.

The term "substantially free" when used in reference to the presence or absence of a protein activity (3-KAR enzymatic activity, ALDH enzymatic activity, PDC enzymatic activity, GPD enzymatic activity, etc.) means the level of the protein is substantially less than that of the same protein in the wild-type host, wherein less than about 50% of the wild-type level is preferred and less than about 30% is more preferred. The activity may be less than about 20%, less than about 10%, less than about 5%, or less than about 1% of wild-type activity. Microorganisms which are "substantially free" of a particular protein activity (3-KAR enzymatic activity, ALDH enzymatic activity, PDC enzymatic activity, GPD enzymatic activity, etc.) may be created through recombinant means or identified in nature.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. $3^{rd}$ edition. p. 28-29. Cambridge University Press, Cambridge, UK) or by monitoring the production of fermentation productions such as ethanol and $CO_2$ The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog," used with respect to an original polynucleotide or polypeptide of a first family or species, refers to distinct polynucleotides or polypeptides of a second family or species which are determined by functional, structural or genomic analyses to be a polynucleotide or polypeptide of the second family or species which corresponds to the original polynucleotide or polypeptide of the first family or species. Most often, homologs will have functional, structural or genomic similarities. Techniques are known by which homologs of a polynucleotide or polypeptide can readily be cloned using genetic probes and PCR. Identity of cloned sequences as homolog can be confirmed using functional assays and/or by genomic mapping of the genes.

A polypeptide has "homology" or is "homologous" to a second polypeptide if the amino acid sequence encoded by a gene has a similar amino acid sequence to that of the second gene. Alternatively, a polypeptide has homology to a second polypeptide if the two polypeptides have "similar" amino acid sequences. (Thus, the terms "homologous polypeptides" or "homologous proteins" are defined to mean that the two polypeptides have similar amino acid sequences).

The term "analog" or "analogous" refers to polynucleotide or polypeptide sequences that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" may include plural referents unless the context clearly dictates otherwise. Thus, for example, reference to "a cannabinoid compound" or "cannabinoid" may include a plurality of such compounds and reference to "the modified host cell" may include reference to one or more modified host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Isobutanol Producing Recombinant Microorganisms

A variety of microorganisms convert sugars to produce pyruvate, which is then utilized in a number of pathways of cellular metabolism. In recent years, microorganisms, including yeast, have been engineered to produce a number of desirable products via pyruvate-driven biosynthetic pathways, including isobutanol, an important commodity chemical and biofuel candidate (See, e.g., commonly owned and co-pending patent publications, US 2009/0226991, US 2010/0143997, US 2011/0020889, US 2011/0076733, and WO 2010/075504).

As described herein, the present invention relates to recombinant microorganisms for producing isobutanol, wherein said recombinant microorganisms comprise an isobutanol producing metabolic pathway. In some embodiments, the isobutanol producing metabolic pathway to convert pyruvate to isobutanol can be comprised of the following reactions:

1. 2 pyruvate→acetolactate+$CO_2$
2. acetolactate+NAD(P)H→2,3-dihydroxyisovalerate+NAD(P)$^+$
3. 2,3-dihydroxyisovalerate→alpha-ketoisovalerate
4. alpha-ketoisovalerate→isobutyraldehyde+$CO_2$
5. isobutyraldehyde+NAD(P)H→isobutanol+NADP In some embodiments, these reactions are carried out by the enzymes 1) Acetolactate synthase (ALS), 2) Ketol-acid reductoisomerase (KARI), 3) Dihydroxy-acid dehydratase (DHAD), 4) 2-keto-acid decarboxylase, e.g., Keto-isovalerate decarboxylase (KIVD), and 5) an Alcohol dehydrogenase (ADH) (FIG. 1). In some embodiments, the recombinant microorganism may be engineered to overexpress one or more of these enzymes. In an exemplary embodiment, the recombinant microorganism is engineered to overexpress all of these enzymes.

Alternative pathways for the production of isobutanol in yeast have been described in WO/2007/050671 and in Dickinson et al., 1998, *J Biol Chem* 273:25751-6. These and other isobutanol producing metabolic pathways are within the scope of the present application. In some embodiments, the isobutanol producing metabolic pathway comprises five substrate to product reactions. In some embodiments, the isobutanol producing metabolic pathway comprises six substrate to product reactions. In yet some embodiments, the isobutanol producing metabolic pathway comprises seven substrate to product reactions.

In various embodiments described herein, the recombinant microorganism comprises an isobutanol producing metabolic pathway. In some embodiments, the isobutanol producing metabolic pathway comprises at least one exogenous gene encoding a polypeptide that catalyzes a step in the conversion of pyruvate to isobutanol. In some embodiments, the isobutanol producing metabolic pathway comprises at least two exogenous genes encoding polypeptides that catalyze steps in the conversion of pyruvate to isobutanol. In yet some embodiments, the isobutanol producing metabolic pathway comprises at least three exogenous genes encoding polypeptides that catalyze steps in the conversion of pyruvate to isobutanol. In yet some embodiments, the isobutanol producing metabolic pathway comprises at least four exogenous genes encoding polypeptides that catalyze steps in the conversion of pyruvate to isobutanol. In yet some embodiments, the isobutanol producing metabolic pathway comprises at least five exogenous genes encoding polypeptides that catalyze steps in the conversion of pyruvate to isobutanol. In yet some embodiments, all of the isobutanol producing metabolic pathway steps in the conversion of pyruvate to isobutanol are converted by exogenously encoded enzymes.

In some embodiments, one or more of the isobutanol pathway genes encodes an enzyme that is localized to the cytosol. In some embodiments, the recombinant microorganisms comprise an isobutanol producing metabolic pathway with at least one isobutanol pathway enzyme localized in the cytosol. In some embodiments, the recombinant microorganisms comprise an isobutanol producing metabolic pathway with at least two isobutanol pathway enzymes localized in the cytosol. In yet some embodiments, the recombinant microorganisms comprise an isobutanol producing metabolic pathway with at least three isobutanol pathway enzymes localized in the cytosol. In yet some embodiments, the recombinant microorganisms comprise an isobutanol producing metabolic pathway with at least four isobutanol pathway enzymes localized in the cytosol. In an exemplary embodiment, the recombinant microorganisms comprise an isobutanol producing metabolic pathway with five isobutanol pathway enzymes localized in the cytosol. In yet another exemplary embodiment, the recombinant microorganisms comprise an isobutanol producing metabolic pathway with all isobutanol pathway enzymes localized in the cytosol. Isobutanol producing metabolic pathways in which one or more genes are localized to the cytosol are described in commonly owned and co-pending U.S. application Ser. No. 12/855,276, which is herein incorporated by reference in its entirety for all purposes.

As is understood in the art, a variety of organisms can serve as sources for the isobutanol pathway enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y. spp. stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia* spp., *Zymomonas* spp., *Staphylococcus* spp., *Bacillus* spp., *Clostridium* spp., *Corynebacterium* spp., *Pseudomonas* spp., *Lactococcus* spp., *Enterobacter* spp., *Streptococcus* spp., *Salmonella* spp., *Slackia* spp., *Cryptobacterium* spp., and *Eggerthella* spp.

In some embodiments, one or more of these enzymes can be encoded by native genes. Alternatively, one or more of these enzymes can be encoded by heterologous genes.

For example, acetolactate synthases capable of converting pyruvate to acetolactate may be derived from a variety of sources (e.g., bacterial, yeast, Archaea, etc.), including *B. subtilis* (GenBank Accession No. Q04789.3), *L. lactis* (GenBank Accession No. NP_267340.1), *S. mutans* (GenBank Accession No. NP_721805.1), *K. pneumoniae* (GenBank Accession No. ZP_06014957.1), *C. glutamicum* (GenBank Accession No. P42463.1), *E. cloacae* (GenBank Accession No. YP_003613611.1), *M. maripaludis* (GenBank Accession No. ABX01060.1), *M. grisea* (GenBank Accession No. AAB81248.1), *T. stipitatus* (GenBank Accession No. XP_002485976.1), or *S. cerevisiae* ILV2 (GenBank Accession No. NP_013826.1). Additional acetolactate synthases capable of converting pyruvate to acetolactate are described in commonly owned and co-pending US Publication No. 2011/0076733, which is herein incorporated by reference in its entirety. A review article characterizing the biosynthesis of acetolactate from pyruvate via the activity of acetolactate synthases is provided by Chipman et al., 1998, *Biochimica et Biophysica Acta* 1385: 401-19, which is herein incorporated by reference in its entirety. Chipman et al. provide an alignment and consensus for the sequences of a representative number of acetolactate synthases. Motifs shared in common between the majority of acetolactate synthases include:

```
                                      (SEQ ID NO: 13)
SGPG(A/C/V)(T/S)N, (SEQ ID NO: 14)
GX(P/A)GX(V/A/T), (SEQ ID NO: 15)
GX(Q/G)(T/A)(L/M)G(Y/F/W)(A/G)X(P/G)(W/A)AX(G/T)
(A/V),
and
                                      (SEQ ID NO: 16)
GD(G/A)(G/S/C)F
``` motifs at amino acid positions corresponding to the 163-169, 240-245, 521-535, and 549-553 residues, respectively, of the *S. cerevisiae* ILV2. Thus, a protein harboring one or more of these amino acid motifs can generally be expected to exhibit acetolactate synthase activity.

Dihydroxy acid dehydratases capable of converting 2,3-dihydroxyisovalerate to α-ketoisovalerate may be derived from a variety of sources (e.g., bacterial, yeast, Archaea, etc.), including *E. coli* (GenBank Accession No. YP_026248.1), *L. lactis* (GenBank Accession No. NP_267379.1), *S. mutans* (GenBank Accession No. NP_722414.1), *M. stadtmanae* (GenBank Accession No. YP_448586.1), *M. tractuosa* (GenBank Accession No. YP_004053736.1), *Eubacterium* SCB49 (GenBank Accession No. ZP_01890126.1), *G. forsetti* (GenBank Accession No. YP_862145.1), *Y. hpolytica* (GenBank Accession No. XP_502180.2), *N. crassa* (GenBank Accession No. XP_963045.1), or *S. cerevisiae* ILV3 (GenBank Accession No. NP_012550.1). Additional dihydroxy acid dehydratases capable of 2,3-dihydroxyisovalerate to α-ketoisovalerate are described in commonly owned and co-pending US Publication No. 2011/0076733. Motifs shared in common between the majority of dihydroxy acid dehydratases include:

```
                                      (SEQ ID NO: 17)
SLXSRXXIA, (SEQ ID NO: 18)
CDKXXPG, (SEQ ID NO: 19)
GXCXGXXTAN, (SEQ ID NO: 20)
GGSTN, (SEQ ID NO: 21)
GPXGXPGMRXE,
```

-continued

```
                                    (SEQ ID NO: 22)
ALXTDGRXSG,
and (SEQ ID NO: 23)
GHXXPEA
``` motifs at amino acid positions corresponding to the 93-101, 122-128, 193-202, 276-280, 482-491, 509-518, and 526-532 residues, respectively, of the *E. coli* dihydroxy acid dehydratase encoded by ilvD. Thus, a protein harboring one or more of these amino acid motifs can generally be expected to exhibit dihydroxy acid dehydratase activity.

2-keto-acid decarboxylases capable of converting α-ketoisovalerate to isobutyraldehyde may be derived from a variety of sources (e.g., bacterial, yeast, Archaea, etc.), including *L. lactis* kivD (GenBank Accession No. YP_003353820.1), *E. cloacae* (GenBank Accession No. P23234.1), *M. smegmatis* (GenBank Accession No. A0R480.1), *M. tuberculosis* (GenBank Accession No. 053865.1), *M. avium* (GenBank Accession No. Q742Q2.1, *A. brasilense* (GenBank Accession No. P51852.1), *L. lactis* kdcA (GenBank Accession No. AAS49166.1), *S. epidermidis* (GenBank Accession No. NP_765765.1), *M. caseolyticus* (GenBank Accession No. YP_002560734.1), *B. megaterium* (GenBank Accession No. YP_003561644.1), *S. cerevisiae* ARO10 (GenBank Accession No. NP_010668.1), or *S. cerevisiae* THIS (GenBank Accession No. CAA98646.1). Additional 2-keto-acid decarboxylases capable of converting α-ketoisovalerate to isobutyraldehyde are described in commonly owned and co-pending US Publication No. 2011/0076733. Motifs shared in common between the majority of 2-keto-acid decarboxylases include:

```
                                    (SEQ ID NO: 24)
FG(V/I)(P/S)G(D/E)(Y/F), (SEQ ID NO: 25)
(T/V)T(F/Y)G(V/A)G(E/A)(L/F)(S/N), (SEQ ID NO: 26)
N(G/A)(L/I/V)AG(S/A)(Y/F)AE, (SEQ ID NO: 27)
(V/I)(L/I/V)XI(V/T/S)G,
and (SEQ ID NO: 28)
GDG(S/A)(L/F/A)Q(L/M)T
``` motifs at amino acid positions corresponding to the 21-27, 70-78, 81-89, 93-98, and 428-435 residues, respectively, of the *L. lactis* 2-keto-acid decarboxylase encoded by kivD. Thus, a protein harboring one or more of these amino acid motifs can generally be expected to exhibit 2-keto-acid decarboxylase activity.

Alcohol dehydrogenases capable of converting isobutyraldehyde to isobutanol may be derived from a variety of sources (e.g., bacterial, yeast, Archaea, etc.), including *L. lactis* (GenBank Accession No. YP_003354381), *B. cereus* (GenBank Accession No. YP_001374103.1), *N. meningitidis* (GenBank Accession No. CBA03965.1), *S. sanguinis* (GenBank Accession No. YP_001035842.1), *L. brevis* (GenBank Accession No. YP_794451.1), *B. thuringiensis* (GenBank Accession No. ZP_04101989.1), *P. acidilactici* (GenBank Accession No. ZP_06197454.1), *B. subtilis* (GenBank Accession No. EHA31115.1), *N. crassa* (GenBank Accession No. CAB91241.1) or *S. cerevisiae* ADH6 (GenBank Accession No. NP_014051.1). Additional alcohol dehydrogenases capable of converting isobutyraldehyde to isobutanol are described in commonly owned and co-pending US Publication Nos. 2011/0076733 and 2011/0201072. Motifs shared in common between the majority of alcohol dehydrogenases include:

```
                                    (SEQ ID NO: 29)
C(H/G)(T/S)D(L/I)H, (SEQ ID NO: 30)
GHEXXGXV, (SEQ ID NO: 31)
(L/V)(Q/K/E)(V/I/K)G(D/Q)(R/H)(V/A), (SEQ ID NO: 32)
CXXCXXC, (SEQ ID NO: 33)
(C/A)(A/G/D)(G/A)XT(T/V),
and (SEQ ID NO: 34)
G(L/A/C)G(G/P)(L/I/V)G
``` motifs at amino acid positions corresponding to the 39-44, 59-66, 76-82, 91-97, 147-152, and 171-176 residues, respectively, of the *L. lactis* alcohol dehydrogenase encoded by adhA. Thus, a protein harboring one or more of these amino acid motifs can generally be expected to exhibit alcohol dehydrogenase activity.

In some embodiments, the yeast microorganism may be engineered to have increased ability to convert pyruvate to isobutanol. In some embodiments, the yeast microorganism may be engineered to have increased ability to convert pyruvate to isobutyraldehyde. In some embodiments, the yeast microorganism may be engineered to have increased ability to convert pyruvate to keto-isovalerate. In some embodiments, the yeast microorganism may be engineered to have increased ability to convert pyruvate to 2,3-dihydroxyisovalerate. In some embodiments, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast. Isobutanol-Producing Metabolic Pathways with Improved KARI Properties As described herein, the present inventors have discovered that KARI enzymes currently being used in isobutanol-producing recombinant microorganisms suffer from product inhibition (i.e., inhibition by 2,3-dihydroxyisovalerate), resulting in low isobutanol productivity. To overcome this problem and thereby improve isobutanol production, the present inventors have identified a group of KARI enzymes exhibiting reduced inhibition by 2,3-dihydroxyisovalerate. Accordingly, this application describes methods of increasing isobutanol production through the use of recombinant microorganisms comprising KARI enzymes with improved properties for the production of isobutanol.

One aspect of the application is directed to an isolated nucleic acid molecule encoding a ketol-acid reductoisomerase (KARI), wherein said KARI is at least about 60% identical to SEQ ID NO: 2. Further within the scope of present application are KARIs which are at least about 65%, 70%, 75%, 80%, 85%, 90%, 91%, 92%, 93%, 94%, 95%, 96%, 97%, 98%, or 99% identical to SEQ ID NO: 2 and/or SEQ ID NO: 12.

In some embodiments, the KARI is derived from the genus *Slackia*. In a specific embodiment, the KARI is derived from *Slackia exigua*. In another specific embodiment, the isolated nucleic acid molecule is comprised of SEQ ID NO: 1. In some embodiments, the KARI is derived from the genus *Cryptobacterium*. In a specific embodiment, the KARI is derived from *Cryptobacterium curtum*. In another specific embodiment, the isolated nucleic acid molecule is comprised of SEQ ID NO: 3. In yet some embodiments, the KARI is derived from the genus *Eggerthella*. In a specific embodiment, the KARI is derived from *Eggerthella lenta*. In another specific embodiment, the isolated nucleic acid molecule is comprised of SEQ ID NO: 5, SEQ ID NO: 7, SEQ ID NO: 9, SEQ ID NO: 89, SEQ ID NO: 91, or SEQ ID NO: 93. Also included within the scope of this application are isolated KARI enzymes that have been modified to be NADH-dependent. Accordingly, the present application further relates to NADH-dependent ketol-acid reductoisomerases (NKRs) derived from a KARI that is at least about 60% identical to SEQ ID NO: 2 and/or SEQ ID NO: 12.

The invention also includes fragments of the disclosed KARI enzymes which comprise at least 50, 100, 150, 200, 250, 300, 350, 400, 450, 500, 550, or 600 amino acid residues and retain one or more activities associated with KARI enzymes. Such fragments may be obtained by deletion mutation, by recombinant techniques that are routine and well-known in the art, or by enzymatic digestion of the KARI enzyme(s) of interest using any of a number of well-known proteolytic enzymes. The invention further includes nucleic acid molecules which encode the above described mutant KARI enzymes and KARI enzyme fragments.

Another aspect of the application relates to a recombinant microorganism comprising at least one nucleic acid molecule encoding a ketol-acid reductoisomerase (KARI), wherein said KARI is at least about 60% identical to SEQ ID NO: 2 and/or SEQ ID NO: 12. Further within the scope of present application are recombinant microorganism comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to SEQ ID NO: 2.

In some embodiments, the KARI is derived from the genus *Slackia*. In a specific embodiment, the KARI is derived from *Slackia exigua*. In another specific embodiment, the KARI is encoded by SEQ ID NO: 1. In some embodiments, the KARI is derived from the genus *Cryptobacterium*. In a specific embodiment, the KARI is derived from *Cryptobacterium curtum*. In another specific embodiment, the KARI is encoded by SEQ ID NO: 3. In yet some embodiments, the KARI is derived from the genus *Eggerthella*. In a specific embodiment, the KARI is derived from *Eggerthella lenta*. In another specific embodiment, the KARI is encoded by SEQ ID NO: 5, SEQ ID NO: 7, SEQ ID NO: 9, SEQ ID NO: 89, SEQ ID NO: 91, or SEQ ID NO: 93.

In an exemplary embodiment, pathway steps 2 and 5 of the isobutanol pathway may be carried out by KARI and ADH enzymes that utilize NADH (rather than NADPH) as a cofactor. It has been found previously that utilization of NADH-dependent KARI (NKR) and ADH enzymes to catalyze pathway steps 2 and 5, respectively, surprisingly enables production of isobutanol at theoretical yield and/or under anaerobic conditions. See, e.g., commonly owned and co-pending patent publication US 2010/0143997. An example of an NADH-dependent isobutanol pathway is illustrated in FIG. 2. Thus, in some embodiments, the recombinant microorganisms of the present invention may use an NKR to catalyze the conversion of acetolactate to produce 2,3-dihydroxyisovalerate. In some embodiments, the recombinant microorganisms of the present invention may use an NADH-dependent ADH to catalyze the conversion of isobutyraldehyde to produce isobutanol. In yet some embodiments, the recombinant microorganisms of the present invention may use both an NKR to catalyze the conversion of acetolactate to produce 2,3-dihydroxyisovalerate, and an NADH-dependent ADH to catalyze the conversion of isobutyraldehyde to produce isobutanol.

In some embodiments, the KARI (NKR) enzymes of the disclosure comprise one or more modifications or mutations that affect proper protein folding. In some embodiments, the KARI (NKR) enzymes of the disclosure comprise one or more modifications or mutations that affect co-factor binding. In some embodiments, the KARI (NKR) enzymes of the disclosure comprise one or more modifications in the cofactor binding domain. In some embodiments, the KARI (NKR) enzymes of the disclosure comprise one or more modifications or mutations in the cofactor-binding pocket.

In some embodiments, the KARI (NKR) enzymes of the disclosure comprise one or more modifications or mutations at positions 31, 77, 91, 94, 126, 150, 165, 290, 293, 299, and/or 330 of the *S. exigua* KARI (Se1_NKR) (SEQ ID NO: 2).

In some embodiments, the KARI (NKR) enzymes of the disclosure comprise one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2). In some embodiments, the KARI (NKR) enzymes of the disclosure comprise one or more modifications or mutations at positions corresponding to amino acids: (a) methionine 77 of the *S. exigua* KARI (SEQ ID NO: 2); (b) valine 91 of the *S. exigua* KARI (SEQ ID NO: 2); (c) lysine 290 of the *S. exigua* KARI (SEQ ID NO: 2); and (d) glutamine 330 of the *S. exigua* KARI (SEQ ID NO: 2). In some embodiments, the KARI (NKR) enzymes of the disclosure comprise one or more modifications or mutations at positions corresponding to amino acids: (a) glycine 31 of the *S. exigua* KARI (Se1_NKR) (SEQ ID NO: 2); (b) methionine 77 of the *S. exigua* KARI (SEQ ID NO: 2); and (c) glutamine 330 of the *S. exigua* KARI (SEQ ID NO: 2). In some embodiments, the KARI (NKR) enzymes of the disclosure comprise one or more modifications or mutations at positions corresponding to amino acids: (a) glycine 31 of the *S. exigua* KARI (Se1_NKR) (SEQ ID NO: 2); (b) valine 91 of the *S. exigua* KARI (SEQ ID NO: 2); and (c) glutamine 330 of the *S. exigua* KARI (SEQ ID NO: 2).

In some embodiments, the present disclosure provides KARI (NKR) enzymes wherein the glycine corresponding to position 31 of the *S. exigua* KARI (SEQ ID NO: 2) is replaced with an alanine or a cysteine. In some embodiments, the present disclosure provides KARI (NKR) enzymes wherein the methionine corresponding to position 77 of the *S. exigua* KARI (SEQ ID NO: 2) is replaced with an isoleucine, valine, or leucine. In some embodiments, the present disclosure provides KARI (NKR) enzymes wherein the valine corresponding to position 91 of the *S. exigua* KARI (SEQ ID NO: 2) is replaced with an isoleucine. In some embodiments, the present disclosure provides KARI (NKR) enzymes wherein the glutamic acid corresponding to position 94 of the *S. exigua* KARI (SEQ ID NO: 2) is replaced with a cysteine. In some embodiments, the present disclosure provides KARI (NKR) enzymes wherein the glutamine corresponding to position 150 of the *S. exigua* KARI (SEQ ID NO: 2) is replaced with tyrosine. In some embodiments, the present disclosure provides KARI (NKR) enzymes wherein the glutamine corresponding to position 165 of the *S. exigua* KARI (SEQ ID NO: 2) is replaced with a serine. In some embodiments, the present disclosure provides KARI (NKR) enzymes wherein the lysine corresponding to position 290 of the *S. exigua* KARI (SEQ ID NO: 2) is replaced with an arginine, alanine, or leucine. In some embodiments, the present disclosure provides KARI (NKR) enzymes wherein the glutamine corresponding to position 293 of the *S. exigua* KARI (SEQ ID NO: 2) is replaced with an arginine or a lysine. In some embodiments, the present disclosure provides KARI (NKR) enzymes wherein the glutamine corresponding to position 330 of the *S. exigua* KARI (SEQ ID NO: 2) is replaced with an arginine or a lysine. In some embodiments, the present disclosure provides KARI (NKR) enzymes wherein the methionine corresponding to position 77 of the *S. exigua* KARI (SEQ ID NO: 2) is replaced with an isoleucine, the valine corresponding to position 91 of the *S. exigua* KARI (SEQ ID NO: 2) is replaced with an isoleucine, the lysine corresponding to position 290 of the *S. exigua* KARI (SEQ ID NO: 2) is replaced with an alanine, and the glutamine corresponding to position 330 of the *S. exigua* KARI (SEQ ID NO: 2) is replaced with an arginine. In some embodiments, the present disclosure provides KARI (NKR) enzymes wherein the glycine corresponding to position 31 of the *S. exigua* KARI (SEQ ID NO: 2) is replaced with an alanine, the methionine corresponding to position 77 of the *S. exigua* KARI (SEQ ID NO: 2) is replaced with an isoleucine, and the glutamine corresponding to position 330 of the *S. exigua* KARI (SEQ ID NO: 2) is replaced with an arginine. In some embodiments, the present disclosure provides KARI (NKR) enzymes wherein the glycine corresponding to position 31 of the *S. exigua* KARI (SEQ ID NO: 2) is replaced with an alanine, the valine corresponding to position 91 of the *S. exigua* KARI (SEQ ID NO: 2) is replaced with an isoleucine, and the glutamine corresponding to position 330 of the *S. exigua* KARI (SEQ ID NO: 2) is replaced with an arginine.

The corresponding positions of the KARI enzyme identified herein (e.g., the *S. exigua* KARI) may be readily identified for other KARI enzymes by one of skill in the art. Thus, given the defined region and the assays described in the present application, one with skill in the art can make one or a number of modifications which would result in an increased ability to utilize NADH, particularly for the conversion of acetolactate to 2,3-dihydroxyisovalerate, in any KARI enzyme of interest. Residues to be modified in accordance with the present application may include those described the Examples herein.

The application also includes fragments of the modified KARI enzymes which comprise at least 50, 100, 150, 200, 250, 300, 350, 400, 450, 500, 550, or 600 amino acid residues and retain one or more activities associated with KARI enzymes. Such fragments may be obtained by deletion mutation, by recombinant techniques that are routine and well-known in the art, or by enzymatic digestion of the KARI enzyme(s) of interest using any of a number of well-known proteolytic enzymes. The invention further includes nucleic acid molecules which encode the above described mutant KARI enzymes and KARI enzyme fragments.

Another aspect of the application relates to a recombinant microorganism comprising at least one nucleic acid molecule encoding a ketol-acid reductoisomerase (KARI), wherein said KARI has one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (0 glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2). In some embodiments, the recombinant microorganism comprises at least one nucleic acid molecule encoding a ketol-acid reductoisomerase (KARI), wherein said KARI has one or more modifications or mutations at positions corresponding to amino acids: (a) methionine 77 of the *S. exigua* KARI (SEQ ID NO: 2); (b) valine 91 of the *S. exigua* KARI (SEQ ID NO: 2); (c) lysine 290 of the *S. exigua* KARI (SEQ ID NO: 2); and (d) glutamine 330 of the *S. exigua* KARI (SEQ ID NO: 2). In some embodiments, the recombinant microorganism comprises at least one nucleic acid molecule encoding a ketol-acid reductoisomerase (KARI), wherein said KARI has one or more modifications or mutations at positions corresponding to amino acids: (a) glycine 31 of the *S. exigua* KARI (Se1_NKR) (SEQ ID NO: 2); (b) methionine 77 of the *S. exigua* KARI (SEQ ID NO: 2); and (c) glutamine 330 of the *S. exigua* KARI (SEQ ID NO: 2). In some embodiments, the recombinant microorganism comprises at least one nucleic acid molecule encoding a ketol-acid reductoisomerase (KARI), wherein said KARI has one or more modifications or mutations at positions corresponding to amino acids: (a) glycine 31 of the *S. exigua* KARI (Se1_NKR) (SEQ ID NO: 2); (b) valine 91 of the *S. exigua* KARI (SEQ ID NO: 2); and (c) glutamine 330 of the *S. exigua* KARI (SEQ ID NO: 2).

In some embodiments, the recombinant microorganism comprises at least one nucleic acid molecule encoding a ketol-acid reductoisomerase (KARI), wherein the glycine corresponding to position 31 of the *S. exigua* KARI (SEQ ID NO: 2) is replaced with an alanine or a cysteine. In some embodiments, the recombinant microorganism comprises at least one nucleic acid molecule encoding a ketol-acid reductoisomerase (KARI), wherein the methionine corresponding to position 77 of the *S. exigua* KARI (SEQ ID NO: 2) is replaced with an isoleucine, valine, or leucine. In some embodiments, the recombinant microorganism comprises at least one nucleic acid molecule encoding a ketol-acid reductoisomerase (KARI), wherein the valine corresponding to position 91 of the *S. exigua* KARI (SEQ ID NO: 2) is replaced with an isoleucine. In some embodiments, the recombinant microorganism comprises at least one nucleic acid molecule encoding a ketol-acid reductoisomerase (KARI), wherein the glutamic acid corresponding to position 94 of the S. exigua KARI (SEQ ID NO: 2) is replaced with a cysteine. In some embodiments, the recombinant microorganism comprises at least one nucleic acid molecule encoding a ketol-acid reductoisomerase (KARI), wherein the glutamine corresponding to position 150 of the S. exigua KARI (SEQ ID NO: 2) is replaced with tyrosine. In some embodiments, the recombinant microorganism comprises at least one nucleic acid molecule encoding a ketol-acid reductoisomerase (KARI), wherein the glutamine corresponding to position 165 of the S. exigua KARI (SEQ ID NO: 2) is replaced with a serine. In some embodiments, the recombinant microorganism comprises at least one nucleic acid molecule encoding a ketol-acid reductoisomerase (KARI), wherein the lysine corresponding to position 290 of the S. exigua KARI (SEQ ID NO: 2) is replaced with an arginine, alanine, or leucine. In some embodiments, the present disclosure provides KARI (NKR) enzymes wherein the glutamine corresponding to position 293 of the S. exigua KARI (SEQ ID NO: 2) is replaced with an arginine or a lysine. In some embodiments, the recombinant microorganism comprises at least one nucleic acid molecule encoding a ketol-acid reductoisomerase (KARI), wherein the glutamine corresponding to position 330 of the S. exigua KARI (SEQ ID NO: 2) is replaced with an arginine or a lysine. In some embodiments, the recombinant microorganism comprises at least one nucleic acid molecule encoding a ketol-acid reductoisomerase (KARI), wherein the methionine corresponding to position 77 of the S. exigua KARI (SEQ ID NO: 2) is replaced with an isoleucine, the valine corresponding to position 91 of the S. exigua KARI (SEQ ID NO: 2) is replaced with an isoleucine, the lysine corresponding to position 290 of the S. exigua KARI (SEQ ID NO: 2) is replaced with an alanine, and the glutamine corresponding to position 330 of the S. exigua KARI (SEQ ID NO: 2) is replaced with an arginine. In some embodiments, the recombinant microorganism comprises at least one nucleic acid molecule encoding a ketol-acid reductoisomerase (KARI), wherein the glycine corresponding to position 31 of the S. exigua KARI (SEQ ID NO: 2) is replaced with an alanine, the methionine corresponding to position 77 of the S. exigua KARI (SEQ ID NO: 2) is replaced with an isoleucine, and the glutamine corresponding to position 330 of the S. exigua KARI (SEQ ID NO: 2) is replaced with an arginine. In some embodiments, the recombinant microorganism comprises at least one nucleic acid molecule encoding a ketol-acid reductoisomerase (KARI), wherein the glycine corresponding to position 31 of the S. exigua KARI (SEQ ID NO: 2) is replaced with an alanine, the valine corresponding to position 91 of the S. exigua KARI (SEQ ID NO: 2) is replaced with an isoleucine, and the glutamine corresponding to position 330 of the S. exigua KARI (SEQ ID NO: 2) is replaced with an arginine.

Further included within the scope of the application are recombinant microorganisms comprising a KARI enzyme, other than the S. exigua KARI (SEQ ID NO: 2), which contains modifications or mutations at positions corresponding to those set out herein.

Further within the scope of present application are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to SEQ ID NO: 2. Also within the scope of present application are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI having one or more modifications or mutations at positions corresponding to amino acids selected from: (a) glycine 31 of the S. exigua KARI (Se1_NKR) (SEQ ID NO: 2); (b) methionine 77 of the S. exigua KARI (SEQ ID NO: 2); (c) valine 91 of the S. exigua KARI (SEQ ID NO: 2); (d) glutamic acid 94 of the S. exigua KARI (SEQ ID NO: 2); (e) tyrosine 126 of the S. exigua KARI (SEQ ID NO: 2); (f) glutamine 150 of the S. exigua KARI (SEQ ID NO: 2); (g) glutamine 165 of the S. exigua KARI (SEQ ID NO: 2); (h) lysine 290 of the S. exigua KARI (SEQ ID NO: 2); (i) glutamine 293 of the S. exigua KARI (SEQ ID NO: 2); (j) glutamine 299 of the S. exigua KARI (SEQ ID NO: 2); and (k) glutamine 330 of the S. exigua KARI (SEQ ID NO: 2). In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI having one or more modifications or mutations at positions corresponding to amino acids: (a) methionine 77 of the S. exigua KARI (SEQ ID NO: 2); (b) valine 91 of the S. exigua KARI (SEQ ID NO: 2); (c) lysine 290 of the S. exigua KARI (SEQ ID NO: 2); and (d) glutamine 330 of the S. exigua KARI (SEQ ID NO: 2). In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI having one or more modifications or mutations at positions corresponding to amino acids: (a) glycine 31 of the S. exigua KARI (Se1_NKR) (SEQ ID NO: 2); (b) methionine 77 of the S. exigua KARI (SEQ ID NO: 2); and (c) glutamine 330 of the S. exigua KARI (SEQ ID NO: 2). In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI having one or more modifications or mutations at positions corresponding to amino acids: (a) glycine 31 of the S. exigua KARI (Se1_NKR) (SEQ ID NO: 2); (b) valine 91 of the S. exigua KARI (SEQ ID NO: 2); and (c) glutamine 330 of the S. exigua KARI (SEQ ID NO: 2).

In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI wherein the glycine corresponding to position 31 of the S. exigua KARI (SEQ ID NO: 2) is replaced with an alanine or a cysteine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the methionine corresponding to position 77 of the S. exigua KARI (SEQ ID NO: 2) is replaced with an isoleucine, valine, or leucine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the valine corresponding to position 91 of the S.

*exigua* KARI (SEQ ID NO: 2) is replaced with an isoleucine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glutamic acid corresponding to position 94 of the *S. exigua* KARI (SEQ ID NO: 2) is replaced with a cysteine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glutamine corresponding to position 150 of the *S. exigua* KARI (SEQ ID NO: 2) is replaced with tyrosine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glutamine corresponding to position 165 of the *S. exigua* KARI (SEQ ID NO: 2) is replaced with a serine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the lysine corresponding to position 290 of the *S. exigua* KARI (SEQ ID NO: 2) is replaced with an arginine, alanine, or leucine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glutamine corresponding to position 293 of the *S. exigua* KARI (SEQ ID NO: 2) is replaced with an arginine or a lysine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glutamine corresponding to position 330 of the *S. exigua* KARI (SEQ ID NO: 2) is replaced with an arginine or a lysine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the methionine corresponding to position 77 of the *S. exigua* KARI (SEQ ID NO: 2) is replaced with an isoleucine, the valine corresponding to position 91 of the *S. exigua* KARI (SEQ ID NO: 2) is replaced with an isoleucine, the lysine corresponding to position 290 of the *S. exigua* KARI (SEQ ID NO: 2) is replaced with an alanine, and the glutamine corresponding to position 330 of the *S. exigua* KARI (SEQ ID NO: 2) is replaced with an arginine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glycine corresponding to position 31 of the *S. exigua* KARI (SEQ ID NO: 2) is replaced with an alanine, the methionine corresponding to position 77 of the *S. exigua* KARI (SEQ ID NO: 2) is replaced with an isoleucine, and the glutamine corresponding to position 330 of the *S. exigua* KARI (SEQ ID NO: 2) is replaced with an arginine. In some embodiments, are recombinant microorganisms comprising at least one nucleic acid molecule encoding a ketol-acid reductoisomerase (KARI), wherein said KARI is at least about 65%, 70%, 75%, 80%, 85%, 90%, 91%, 92%, 93%, 94%, 95%, 96%, 97%, 98%, or 99% identical to a KARI, wherein the glycine corresponding to position 31 of the *S. exigua* KARI (SEQ ID NO: 2) is replaced with an alanine, the valine corresponding to position 91 of the *S. exigua* KARI (SEQ ID NO: 2) is replaced with an isoleucine, and the glutamine corresponding to position 330 of the *S. exigua* KARI (SEQ ID NO: 2) is replaced with an arginine.

In accordance with the invention, any number of mutations can be made to the KARI enzymes, and in a preferred aspect, multiple mutations can be made to result in an increased ability to utilize NADH for the conversion of acetolactate to 2,3-dihydroxyisovalerate. Such mutations include point mutations, frame shift mutations, deletions, and insertions, with one or more (e.g., one, two, three, four, five or more, etc.) point mutations preferred.

Mutations may be introduced into the KARI enzymes of the present application to create NKRs using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the NKRs which allows for all possible classes of base pair changes at any determined site along the encoding DNA molecule. In general, this technique involves annealing an oligonucleotide complementary (except for one or more mismatches) to a single stranded nucleotide sequence coding for the KARI enzyme of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

In one aspect, the NADH-dependent activity of the modified or mutated KARI enzyme is increased. In some embodiments, the modified or mutated KARI enzyme of the present disclosure exhibits greater conversion of acetolactate to 2,3-dihydroxyisovalerate than that observed with an unmodified or unmutated KARI enzyme. In some embodiments, the modified or mutated KARI enzyme of the present disclosure exhibits a lower $NADH_{K50}$ for acetolactate conversion than that observed with an unmodified or unmutated KARI enzyme. In some embodiments, the modified or mutated KARI enzyme of the present disclosure exhibits a greater $NADH_{Kcat}$ for acetolactate conversion than that observed with an unmodified or unmutated KARI enzyme. In some embodiments, the modified or mutated KARI enzyme of the present disclosure exhibits both a lower $NADH_{K50}$ and a greater $NADH_{Kcat}$ for acetolactate conversion than that observed with an unmodified or unmutated KARI enzyme.

In an exemplary embodiment, the catalytic efficiency of the modified or mutated KARI enzyme is improved for the cofactor NADH. Preferably, the catalytic efficiency of the modified or mutated KARI enzyme is improved by at least about 5% as compared to the wild-type or parental KARI for NADH. More preferably the catalytic efficiency of the modified or mutated KARI enzyme is improved by at least about 15% as compared to the wild-type or parental KARI for NADH. More preferably, the catalytic efficiency of the modified or mutated KARI enzyme is improved by at least about 25% as compared to the wild-type or parental KARI for NADH. More preferably, the catalytic efficiency of the modified or mutated KARI enzyme is improved by at least about 50% as compared to the wild-type or parental KARI for NADH. More preferably, the catalytic efficiency of the modified or mutated KARI enzyme is improved by at least about 75% as compared to the wild-type or parental KARI for NADH. More preferably, the catalytic efficiency of the modified or mutated KARI enzyme is improved by at least about 100% as compared to the wild-type or parental KARI for NADH. More preferably, the catalytic efficiency of the modified or mutated KARI enzyme is improved by at least about 300% as compared to the wild-type or parental KARI for NADH. More preferably, the catalytic efficiency of the modified or mutated KARI enzyme is improved by at least about 500% as compared to the wild-type or parental KARI for NADH. More preferably, the catalytic efficiency of the modified or mutated KARI enzyme is improved by at least about 1000% as compared to the wild-type or parental KARI for NADH. More preferably, the catalytic efficiency of the modified or mutated KARI enzyme is improved by at least about 5000% as compared to the wild-type or parental KARI for NADH.

In another exemplary embodiment, the catalytic efficiency of the modified or mutated KARI enzyme with NADH is increased with respect to the catalytic efficiency of the wild-type or parental enzyme with NADPH. Preferably, the catalytic efficiency of the modified or mutated KARI enzyme is at least about 10% of the catalytic efficiency of the wild-type or parental KARI enzyme for NADPH. More preferably, the catalytic efficiency of the modified or mutated KARI enzyme is at least about 25% of the catalytic efficiency of the wild-type or parental KARI enzyme for NADPH. More preferably, the catalytic efficiency of the modified or mutated KARI enzyme is at least about 50% of the catalytic efficiency of the wild-type or parental KARI enzyme for NADPH. More preferably, the catalytic efficiency of the modified or mutated KARI enzyme is at least about 75%, 85%, 95% of the catalytic efficiency of the wild-type or parental KARI enzyme for NADPH.

In another exemplary embodiment, the $K_M$ of the KARI enzyme for NADH is decreased relative to the wild-type or parental enzyme. A change in $K_M$ is evidenced by at least a 5% or greater increase or decrease in $K_M$ compared to the wild-type KARI enzyme. In certain embodiments, modified or mutated KARI enzymes of the present invention may show greater than 10 times decreased $K_M$ for NADH compared to the wild-type or parental KARI enzyme. In certain embodiments, modified or mutated KARI enzymes of the present invention may show greater than 30 times decreased $K_M$ for NADH compared to the wild-type or parental KARI enzyme.

In another exemplary embodiment, the $k_{cat}$ of the KARI enzyme with NADH is increased relative to the wild-type or parental enzyme. A change in $k_{cat}$ is evidenced by at least a 5% or greater increase or decrease in $K_M$ compared to the wild-type KARI enzyme. In certain embodiments, modified or mutated KARI enzymes of the present invention may show greater than 50% increased $k_{cat}$ for NADH compared to the wild-type or parental KARI enzyme. In certain embodiments, modified or mutated KARI enzymes of the present invention may show greater than 100% increased $k_{cat}$ for NADH compared to the wild-type or parental KARI enzyme. In certain embodiments, modified or mutated KARI enzymes of the present invention may show greater than 200% increased $k_{cat}$ for NADH compared to the wild-type or parental KARI enzyme.

In some embodiments, expression of the variant KARI enzyme of the present disclosure in a host cell increases isobutanol production in the host cell relative to the amount of isobutanol produced by expression of the wild type KARI enzyme or Se1_NKR disclosed herein (e.g. SEQ ID NO: 2 or SEQ ID NO: 12). In some embodiments, expression of the variant KARI enzyme of the present disclosure in a host cell increases isobutanol production by about 0.05% to about 500% relative to the amount of isobutanol produced by expression of the wild type KARI enzyme or Se1_NKR disclosed herein (e.g. SEQ ID NO: 2 or SEQ ID NO: 12). In some embodiments, expression of the variant KARI enzyme of the present disclosure in a host cell increases isobutanol production by about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, or about 10.0% relative to the amount of isobutanol produced by expression of the wild type KARI enzyme or Se1_NKR disclosed herein (e.g. SEQ ID NO: 2 or SEQ ID NO: 12). In some embodiments, the KARI variant is v1 (e.g. SEQ ID NO: 90), v48 (e.g. SEQ ID NO: 92), or v65 (e.g. SEQ ID NO: 94). In some embodiments, the KARI variant is v1 and isobutanol production is increased by about 5% relative to isobutanol expression of the wild type KARI enzyme or Se1_NKR disclosed herein (e.g. SEQ ID NO: 2 or SEQ ID NO: 12).

In some embodiments, expression of the variant KARI enzyme of the present disclosure in a host cell increases isobutanol production by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500% relative to the amount of isobutanol produced by expression of the wild type KARI enzyme or Se1_NKR disclosed herein (e.g. SEQ ID NO: 2 or SEQ ID NO: 12). In some embodiments, the KARI variant is v1 (e.g. SEQ ID NO: 90), v48 (e.g. SEQ ID NO: 92), or v65 (e.g. SEQ ID NO: 94). In some embodiments, the KARI variant is v1 and isobutanol production is increased by about 5% relative to isobutanol expression of the wild type KARI enzyme or Se1_NKR disclosed herein (e.g. SEQ ID NO: 2 or SEQ ID NO: 12).

Recombinant Microorganisms Comprising KARI with Improved Properties

In addition to isobutanol producing metabolic pathways, a number of biosynthetic pathways use KARI enzymes to catalyze a reaction step, including pathways for the production of isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol. A representative list of the engineered biosynthetic pathways utilizing KARI enzymes is provided in Table 1.

pathways. Thus, in an additional aspect, the present application relates to a recombinant microorganism comprising a KARI-requiring biosynthetic pathway, wherein said recombinant microorganism comprises at least one nucleic acid molecule encoding a KARI that is at least about 60% identical to SEQ ID NO: 2 and/or SEQ ID NO: 12. In some embodiments, the KARI is derived from the genus *Slackia*. In a specific embodiment, the KARI is derived from *Slackia exigua*. In another specific embodiment, the KARI is encoded by SEQ ID NO: 1. In some embodiments, the KARI is derived from the genus *Cryptobacterium*. In a specific embodiment, the KARI is derived from *Cryptobacterium curtum*. In another specific embodiment, the KARI is encoded by SEQ ID NO: 3. In yet some embodiments, the KARI is derived from the genus *Eggerthella*. In a specific embodiment, the KARI is derived from *Eggerthella lenta*. In another specific embodiment, the KARI is encoded by SEQ ID NO: 5, SEQ ID NO: 7, SEQ ID NO: 9, SEQ ID NO: 89, SEQ ID NO: 91, or SEQ ID NO: 93. In yet some embodiments, the KARI has one or more modifications or mutations at positions corresponding to amino acids selected from: (a) tyrosine 35 of the *S. exigua* KARI (SEQ ID NO: 2); (b) leucine 57 of the *S. exigua* KARI (SEQ ID NO: 2); (c) arginine 58 of the *S. exigua* KARI (SEQ ID NO: 2); (d) glycine 60 of the *S. exigua* KARI (SEQ ID NO: 2); (e) serine 61 of the *S. exigua* KARI (SEQ ID NO: 2); (f) serine 62 of the *S. exigua* KARI (SEQ ID NO: 2); (g) serine 63 of the *S. exigua* KARI (SEQ ID NO: 2); (h) isoleucine 95 of the *S. exigua* KARI (SEQ ID NO: 2); and (i) valine 99 of the *S. exigua* KARI (SEQ ID NO: 2). In yet some embodiments, the KARI has one or more modifications or mutations at positions corresponding to amino acids: (a) methionine 77 of the *S. exigua* KARI (SEQ ID NO: 2); (b) valine 91 of the *S. exigua* KARI (SEQ ID NO: 2); (c) lysine 290 of the *S. exigua* KARI (SEQ ID NO: 2); and (d) glutamine 330 of the

| Biosynthetic Pathway | Reference[a] |
|---|---|
| Isobutanol | US 2009/0226991 (Feldman et al.), US 2011/0020889 (Feldman et al.), and US 2010/0143997 (Buelter et al.) |
| Leucine | WO/2001/021772 (Yocum et al.) and McCourt et al., 2006, *Amino Acids* 31: 173-210 |
| Valine | WO/2001/021772 (Yocum et al.) and McCourt et al., 2006, *Amino Acids* 31: 173-210 |
| Pantothenic Acid | WO/2001/021772 (Yocum et al.) |
| Coenzyme A | WO/2001/021772 (Yocum etal.) |
| 1-Butanol | WO/2010/017230 (Lynch), WO/2010/031772 (Wu et al.), and KR2011002130 (Lee etal.) |
| 2-Methyl-1-Butanol | WO/2008/098227 (Liao et al.), WO/2009/076480 (Picataggio et al.), and Atsumi et al., 2008, *Nature* 451: 86-89 |
| 3-Methyl-1-Butanol | WO/2008/098227 (Liao et al.), Atsumi et al., 2008, *Nature* 451: 86-89, and Connor et al., 2008, *Appl. Environ. Microbiol.* 74: 5769-5775 |
| 3-Methyl-1-Pentanol | WO/2010/045629 (Liao et al.), Zhang et al., 2008, *Proc Natl Acad Sci USA* 105: 20653-20658 |
| 4-Methyl-1-Pentanol | WO/2010/045629 (Liao et al.), Zhang et al., 2008, *Proc Natl Acad Sci USA* 105: 20653-20658 |
| 4-Methyl-1-Hexanol | WO/2010/045629 (Liao et al.), Zhang et al., 2008, *Proc Natl Acad Sci USA* 105: 20653-20658 |
| 5-Methyl-1-Heptanol | WO/2010/045629 (Liao et al.), Zhang et al., 2008, *Proc Natl Acad Sci USA* 105: 20653-20658 |

[a]The contents of each of the references in this table are herein incorporated by reference in their entireties for all purposes.

60

As described above, each of these biosynthetic pathways uses a KARI enzyme to catalyze a reaction step. Therefore, the product yield from these biosynthetic pathways will in part depend upon the activity of KARI.

As will be understood by one skilled in the art equipped with the present disclosure, the KARI enzymes described herein would have utility in any of the above-described

*S. exigua* KARI (SEQ ID NO: 2). In yet some embodiments, the KARI has one or more modifications or mutations at positions corresponding to amino acids: (a) glycine 31 of the *S. exigua* KARI (Se1_NKR) (SEQ ID NO: 2); (b) methionine 77 of the *S. exigua* KARI (SEQ ID NO: 2); and (c) glutamine 330 of the *S. exigua* KARI (SEQ ID NO: 2). In yet some embodiments, the KARI has one or more modifications or mutations at positions corresponding to amino acids: (a) glycine 31 of the *S. exigua* KARI (Se1_NKR) (SEQ ID NO: 2); (b) valine 91 of the *S. exigua* KARI (SEQ ID NO: 2); and (c) glutamine 330 of the *S. exigua* KARI (SEQ ID NO: 2).

In yet some embodiments, the KARI has one or more modifications or mutations, wherein the glycine corresponding to position 31 of the *S. exigua* KARI (SEQ ID NO: 2) is replaced with an alanine or a cysteine. In yet some embodiments, the KARI has one or more modifications or mutations, wherein the methionine corresponding to position 77 of the *S. exigua* KARI (SEQ ID NO: 2) is replaced with an isoleucine, valine, or leucine. In yet some embodiments, the KARI has one or more modifications or mutations, wherein the valine corresponding to position 91 of the *S. exigua* KARI (SEQ ID NO: 2) is replaced with an isoleucine. In yet some embodiments, the KARI has one or more modifications or mutations, wherein the glutamic acid corresponding to position 94 of the *S. exigua* KARI (SEQ ID NO: 2) is replaced with a cysteine. In yet some embodiments, the KARI has one or more modifications or mutations, wherein the glutamine corresponding to position 150 of the *S. exigua* KARI (SEQ ID NO: 2) is replaced with tyrosine. In yet some embodiments, the KARI has one or more modifications or mutations, wherein the glutamine corresponding to position 165 of the *S. exigua* KARI (SEQ ID NO: 2) is replaced with a serine. In yet some embodiments, the KARI has one or more modifications or mutations, wherein the lysine corresponding to position 290 of the *S. exigua* KARI (SEQ ID NO: 2) is replaced with an arginine, alanine, or leucine. In yet some embodiments, the KARI has one or more modifications or mutations, wherein the glutamine corresponding to position 293 of the *S. exigua* KARI (SEQ ID NO: 2) is replaced with an arginine or a lysine. In yet some embodiments, the KARI has one or more modifications or mutations, wherein the glutamine corresponding to position 330 of the *S. exigua* KARI (SEQ ID NO: 2) is replaced with an arginine or a lysine. In yet some embodiments, the KARI has one or more modifications or mutations, wherein the methionine corresponding to position 77 of the *S. exigua* KARI (SEQ ID NO: 2) is replaced with an isoleucine, the valine corresponding to position 91 of the *S. exigua* KARI (SEQ ID NO: 2) is replaced with an isoleucine, the lysine corresponding to position 290 of the *S. exigua* KARI (SEQ ID NO: 2) is replaced with an alanine, and the glutamine corresponding to position 330 of the *S. exigua* KARI (SEQ ID NO: 2) is replaced with an arginine. In yet some embodiments, the KARI has one or more modifications or mutations, wherein the glycine corresponding to position 31 of the *S. exigua* KARI (SEQ ID NO: 2) is replaced with an alanine, the methionine corresponding to position 77 of the *S. exigua* KARI (SEQ ID NO: 2) is replaced with an isoleucine, and the glutamine corresponding to position 330 of the *S. exigua* KARI (SEQ ID NO: 2) is replaced with an arginine. In yet some embodiments, the KARI has one or more modifications or mutations, wherein the glycine corresponding to position 31 of the *S. exigua* KARI (SEQ ID NO: 2) is replaced with an alanine, the valine corresponding to position 91 of the *S. exigua* KARI (SEQ ID NO: 2) is replaced with an isoleucine, and the glutamine corresponding to position 330 of the *S. exigua* KARI (SEQ ID NO: 2) is replaced with an arginine.

As used herein, a "KARI-requiring biosynthetic pathway" refers to any metabolic pathway which utilizes KARI to convert acetolactate to 2,3-dihydroxyisovalerate or 2-aceto-2-hydroxy-butanoate to 2,3-dihydroxy-3-methylvalerate. Examples of KARI-requiring biosynthetic pathways include, but are not limited to, isobutanol, isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol metabolic pathways. The metabolic pathway may naturally occur in a microorganism (e.g., a natural pathway for the production of valine) or arise from the introduction of one or more heterologous polynucleotides through genetic engineering. In an exemplary embodiment, the recombinant microorganisms expressing the KARI-requiring biosynthetic pathway are yeast cells.

The Microorganism in General

As described herein, the recombinant microorganisms of the present invention can express a plurality of heterologous and/or native enzymes involved in pathways for the production of a beneficial metabolite such as isobutanol.

As described herein, "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g., the ability to produce a new, or greater quantities of, an intracellular and/or extracellular metabolite. As described herein, the introduction of genetic material into and/or the modification of the expression of native genes in a parental microorganism results in a new or modified ability to produce beneficial metabolites such as isobutanol from a suitable carbon source. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g., promoter sequences.

In addition to the introduction of a genetic material into a host or parental microorganism, an engineered or modified microorganism can also include the alteration, disruption, deletion or knocking-out of a gene or polynucleotide to alter the cellular physiology and biochemistry of the microorganism. Through the alteration, disruption, deletion or knocking-out of a gene or polynucleotide, the microorganism acquires new or improved properties (e.g., the ability to produce a new metabolite or greater quantities of an intracellular metabolite, to improve the flux of a metabolite down a desired pathway, and/or to reduce the production of by-products).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See commonly owned and co-pending application US 2009/0226991. A typical algorithm used comparing a molecule sequence to a database containing a large number of sequences from different organisms is the computer program BLAST. When searching a database containing sequences from a large number of different organisms, it is typical to compare amino acid sequences. Database searching using amino acid sequences can be measured by algorithms described in commonly owned U.S. Pat. No. 8,017,375.

It is understood that a range of microorganisms can be modified to include an isobutanol producing metabolic pathway suitable for the production of isobutanol. In various embodiments, the microorganisms may be selected from yeast microorganisms. Yeast microorganisms for the production of isobutanol may be selected based on certain characteristics:

One characteristic may include the property that the microorganism is selected to convert various carbon sources into isobutanol. The term "carbon source" generally refers to a substance suitable to be used as a source of carbon for prokaryotic or eukaryotic cell growth. Examples of suitable carbon sources are described in commonly owned U.S. Pat. No. 8,017,375. Accordingly, in some embodiments, the recombinant microorganism herein disclosed can convert a variety of carbon sources to products, including but not limited to glucose, galactose, mannose, xylose, arabinose, lactose, sucrose, $CO_2$, and mixtures thereof.

The recombinant microorganism may thus further include a pathway for the production of isobutanol from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via a xylulokinase (XK) enzyme. This pathway operates inefficiently in yeast species because it introduces a redox imbalance in the cell. The xylose-to-xylitol step uses primarily NADPH as a cofactor (generating NADP+), whereas the xylitol-to-xylulose step uses NAD+ as a cofactor (generating NADH). Other processes must operate to restore the redox imbalance within the cell. This often means that the organism cannot grow anaerobically on xylose or other pentose sugars. Accordingly, a yeast species that can efficiently ferment xylose and other pentose sugars into a desired fermentation product is therefore very desirable.

Thus, in one aspect, the recombinant microorganism is engineered to express a functional exogenous xylose isomerase. Exogenous xylose isomerases (XI) functional in yeast are known in the art. See, e.g., Rajgarhia et al., U.S. Pat. No. 7,943,366, which is herein incorporated by reference in its entirety. In an embodiment according to this aspect, the exogenous XI gene is operatively linked to promoter and terminator sequences that are functional in the yeast cell. In a preferred embodiment, the recombinant microorganism further has a deletion or disruption of a native gene that encodes for an enzyme (e.g., XR and/or XDH) that catalyzes the conversion of xylose to xylitol. In a further preferred embodiment, the recombinant microorganism also contains a functional, exogenous xylulokinase (XK) gene operatively linked to promoter and terminator sequences that are functional in the yeast cell. In some embodiments, the xylulokinase (XK) gene is overexpressed.

In some embodiments, the yeast microorganism has reduced or no pyruvate decarboxylase (PDC) activity. PDC catalyzes the decarboxylation of pyruvate to acetaldehyde, which is then reduced to ethanol by ADH via an oxidation of NADH to NAD+. Ethanol production is the main pathway to oxidize the NADH from glycolysis. Deletion, disruption, or mutation of this pathway increases the pyruvate and the reducing equivalents (NADH) available for a biosynthetic pathway which uses pyruvate as the starting material and/or as an intermediate. Accordingly, deletion, disruption, or mutation of one or more genes encoding for pyruvate decarboxylase and/or a positive transcriptional regulator thereof can further increase the yield of the desired pyruvate-derived metabolite (e.g., isobutanol). In some embodiments, said pyruvate decarboxylase gene targeted for disruption, deletion, or mutation is selected from the group consisting of PDC1, PDC5, and PDC6, or homologs or variants thereof. In some embodiments, all three of PDC1, PDC5, and PDC6 are targeted for disruption, deletion, or mutation. In yet some embodiments, a positive transcriptional regulator of the PDC1, PDC5, and/or PDC6 is targeted for disruption, deletion or mutation. In some embodiments, said positive transcriptional regulator is PDC2, or homologs or variants thereof.

As is understood by those skilled in the art, there are several additional mechanisms available for reducing or disrupting the activity of a protein encoded by PDC1, PDC5, PDC6, and/or PDC2, including, but not limited to, the use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof. Yeast strains with reduced PDC activity are described in commonly owned U.S. Pat. No. 8,017,375, as well as commonly owned and co-pending US Patent Publication No. 2011/0183392.

In some embodiments, the microorganism has reduced glycerol-3-phosphate dehydrogenase (GPD) activity. GPD catalyzes the reduction of dihydroxyacetone phosphate (DHAP) to glycerol-3-phosphate (G3P) via the oxidation of NADH to NAD+. Glycerol is then produced from G3P by Glycerol-3-phosphatase (GPP). Glycerol production is a secondary pathway to oxidize excess NADH from glycolysis. Reduction or elimination of this pathway would increase the pyruvate and reducing equivalents (NADH) available for the production of a pyruvate-derived metabolite (e.g., isobutanol). Thus, disruption, deletion, or mutation of the genes encoding for glycerol-3-phosphate dehydrogenases can further increase the yield of the desired metabolite (e.g., isobutanol). Yeast strains with reduced GPD activity are described in commonly owned and co-pending US Patent Publication Nos. 2011/0020889 and 2011/0183392.

In yet some embodiments, the microorganism has reduced 3-keto acid reductase (3-KAR) activity. 3-KARs catalyze the conversion of 3-keto acids (e.g., acetolactate) to 3-hydroxyacids (e.g., DH2 MB). Yeast strains with reduced 3-KAR activity are described in commonly owned U.S. Pat. Nos. 8,133,715, 8,153,415, and 8,158,404, which are herein incorporated by reference in their entireties.

In yet some embodiments, the microorganism has reduced aldehyde dehydrogenase (ALDH) activity. Aldehyde dehydrogenases catalyze the conversion of aldehydes (e.g., isobutyraldehyde) to acid by-products (e.g., isobutyrate). Yeast strains with reduced ALDH activity are described in commonly owned U.S. Pat. Nos. 8,133,715, 8,153,415, and 8,158,404, which are herein incorporated by reference in their entireties.

In some embodiments, the yeast microorganisms may be selected from the "*Saccharomyces* Yeast Clade", as described in commonly owned U.S. Pat. No. 8,017,375.

The term "*Saccharomyces sensu stricto*" taxonomy group is a cluster of yeast species that are highly related to *S. cerevisiae* (Rainieri et al., 2003, *J. Biosci Bioengin* 96: 1-9). *Saccharomyces sensu stricto* yeast species include but are not limited to *S. cerevisiae, S. kudriavzevii, S. mikatae, S. bayanus, S. uvarum, S. carocanis* and hybrids derived from these species (Masneuf et al., 1998, *Yeast* 7: 61-72).

An ancient whole genome duplication (WGD) event occurred during the evolution of the hemiascomycete yeast and was discovered using comparative genomic tools (Kellis et al., 2004, *Nature* 428: 617-24; Dujon et al., 2004, *Nature* 430:35-44; Langkjaer et al., 2003, *Nature* 428: 848-52; Wolfe et al., 1997, *Nature* 387: 708-13). Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in some embodiments, the yeast microorganism may be selected from a post-WGD yeast genus, including but not limited to *Saccharomyces* and *Candida* The favored post-WGD yeast species include: *S. cerevisiae, S. uvarum, S. bayanus, S. paradoxus, S. castelli,* and *C. glabrata.*

In some embodiments, the yeast microorganism may be selected from a pre-whole genome duplication (pre-WGD) yeast genus including but not limited to *Saccharomyces, Kluyveromyces, Candida, Pichia, Issatchenkia, Debaryomyces, Hansenula, Yarrowia* and, *Schizosaccharomyces.* Representative pre-WGD yeast species include: *S. kluyveri, K thermotolerans, K marxianus, K waltii, K. lactis, C. tropicalis, P. pastoris, P. anomala, P. stipitis, I. orientalis, I. occidentalis, I. scutulata, D. hansenii, H anomala, Y. lipolytica,* and *S. pombe.*

A yeast microorganism may be either Crabtree-negative or Crabtree-positive as described in described in commonly owned U.S. Pat. No. 8,017,375. In some embodiments the yeast microorganism may be selected from yeast with a Crabtree-negative phenotype including but not limited to the following genera: *Saccharomyces, Kluyveromyces, Pichia, Issatchenkia, Hansenula,* and *Candida.* Crabtree-negative species include but are not limited to: *S. kluyveri, K lactis, K marxianus, P. anomala, P. stipitis, I. orientalis, I. occidentalis, I. scutulata, H. anomala,* and *C. utilis.* In some embodiments, the yeast microorganism may be selected from yeast with a Crabtree-positive phenotype, including but not limited to *Saccharomyces, Kluyveromyces, Zygosaccharomyces, Debaryomyces, Pichia* and *Schizosaccharomyces.* Crabtree-positive yeast species include but are not limited to: *S. cerevisiae, S. uvarum, S. bayanus, S. paradoxus, S. castelli, K. thermotolerans, C. glabrata, Z. bailli, Z. rouxii, D. hansenii, P. pastorius,* and *S. pombe.*

Another characteristic may include the property that the microorganism is that it is non-fermenting. In other words, it cannot metabolize a carbon source anaerobically while the yeast is able to metabolize a carbon source in the presence of oxygen. Nonfermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). In some embodiments, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the biosynthetic pathway. Fermentative pathways contribute to low yield and low productivity of pyruvate-derived metabolites such as isobutanol. Accordingly, deletion of one or more PDC genes may increase yield and productivity of a desired metabolite (e.g., isobutanol).

In some embodiments, the recombinant microorganisms may be microorganisms that are non-fermenting yeast microorganisms, including, but not limited to those, classified into a genera selected from the group consisting of Tricosporon, *Rhodotorula, Myxozyma,* or *Candida.* In a specific embodiment, the non-fermenting yeast is *C. xestobii.*

Methods in General

Identification of KARI Homologs

Any method can be used to identify genes that encode for enzymes that are homologous to the genes described herein (e.g., KARI homologs). Generally, genes that are homologous or similar to the KARIs described herein may be identified by functional, structural, and/or genetic analysis. In most cases, homologous or similar genes and/or homologous or similar enzymes will have functional, structural, or genetic similarities.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a gene by PCR using primers based on a published sequence of a gene/enzyme or by degenerate PCR using degenerate primers designed to amplify a conserved region among ketol-acid reductoisomerase genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K. *Branched-Chain Amino Acids* Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., 1992, *Nuc Acids Res.* 27: 69-74; Ito et al., 1983, *J. Bacteriol.* 153: 163-8; and Becker et al., 1991, *Methods in Enzymology* 194: 182-7.

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., 1981, *PNAS USA* 78: 6354-58).

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In some embodiments, integration of a gene into the chromosome of the yeast microorganism may occur via random integration (Kooistra et al., 2004, *Yeast* 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke et al., 1984, *Mol. Gen. Genet* 197: 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, mitochondrial genome, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced PDC, GPD, ALDH, or 3-KAR activity. The term "reduced" as used herein with respect to a particular polypeptide activity refers to a lower level of polypeptide activity than that measured in a comparable yeast cell of the same species. The term reduced also refers to the elimination of polypeptide activity as compared to a comparable yeast cell of the same species. Thus, yeast cells lacking activity for an endogenous PDC, GPD, ALDH, or 3-KAR are considered to have reduced activity for PDC, GPD, ALDH, or 3-KAR since most, if not all, comparable yeast strains have at least some activity for PDC, GPD, ALDH, or 3-KAR. Such reduced PDC, GPD, ALDH, or 3-KAR activities can be the result of lower PDC, GPD, ALDH, or 3-KAR concentration (e.g., via reduced expression), lower specific activity of the PDC, GPD, ALDH, or 3-KAR, or a combination thereof. Many different methods can be used to make yeast having reduced PDC, GPD, ALDH, or 3-KAR activity. For example, a yeast cell can be engineered to have a disrupted PDC-, GPD-, ALDH-, or 3-KAR-encoding locus using common mutagenesis or knock-out technology. See, e.g., Methods in Yeast Genetics (1997 edition), Adams, Gottschling, Kaiser, and Stems, Cold Spring Harbor Press (1998). In addition, a yeast cell can be engineered to partially or completely remove the coding sequence for a particular PDC, GPD, ALDH, or 3-KAR. Furthermore, the promoter sequence and/or associated regulatory elements can be mutated, disrupted, or deleted to reduce the expression of a PDC, GPD, ALDH, or 3-KAR. Moreover, certain point-mutation(s) can be introduced which results in a PDC, GPD, ALDH, or 3-KAR with reduced activity. Also included within the scope of this invention are yeast strains which when found in nature, are substantially free of one or more PDC, GPD, ALDH, or 3-KAR activities.

Alternatively, antisense technology can be used to reduce PDC, GPD, ALDH, or 3-KAR activity. For example, yeasts can be engineered to contain a cDNA that encodes an antisense molecule that prevents a PDC, GPD, ALDH, or 3-KAR from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In some embodiments, heterologous control elements can be used to activate or repress expression of endogenous genes. Additionally, when expression is to be repressed or eliminated, the gene for the relevant enzyme, protein or RNA can be eliminated by known deletion techniques.

In some embodiments, overexpression of a heterologous gene is accomplished by expressing a protein from multiple copies of the heterologous gene in the cell. In some embodiments, the cell possesses between about 2 to about 70 copies of the heterologous gene. In some embodiments, the cell possesses about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, or about 70 copies of the heterologous gene. In some embodiments, a cell that possesses multiple copies of a heterologous gene demonstrates increased isobutanol yield compared to a cell possessing one or fewer copies of the same heterologous gene. In some embodiments, the heterologous gene is an NKR or a variant thereof. In some embodiments, the heterologous gene is Se1_NKR or a variant thereof. In some embodiments, the heterologous gene is Se2_NKR or a variant thereof.

As described herein, any yeast within the scope of the disclosure can be identified by selection techniques specific to the particular polypeptide (e.g. an isobutanol pathway enzyme) being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, 1992, *Appl. Micro. Biot.* 38:17-22.

Increase of Enzymatic Activity

Yeast microorganisms of the invention may be further engineered to have increased activity of enzymes (e.g., increased activity of enzymes involved in an isobutanol producing metabolic pathway). The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the $K_M$ for the substrate, or by directed evolution. See, e.g., Methods in Molecular Biology (vol. 231), ed. Arnold and Georgiou, Humana Press (2003).

Methods of Using Recombinant Microorganisms for Metabolite Production

For a biocatalyst to produce a beneficial metabolite most economically, it is desirable to produce said metabolite at a high yield. Preferably, the only product produced is the desired metabolite, as extra products (i.e. by-products) lead to a reduction in the yield of the desired metabolite and an increase in capital and operating costs, particularly if the extra products have little or no value. These extra products also require additional capital and operating costs to separate these products from the desired metabolite.

In one aspect, the present application provides methods of producing a desired metabolite using a recombinant described herein. In some embodiments, the recombinant microorganism comprises a KARI-requiring biosynthetic pathway, wherein said recombinant microorganism comprises at least one nucleic acid molecule encoding a KARI that is at least about 60% identical to SEQ ID NO: 2 and/or SEQ ID NO: 12. In some embodiments, the KARI is derived from the genus *Slackia*. In a specific embodiment, the KARI is derived from *Slackia exigua*. In another specific embodiment, the KARI is encoded by SEQ ID NO: 1. In some embodiments, the KARI is derived from the genus *Cryptobacterium*. In a specific embodiment, the KARI is derived from *Cryptobacterium curtum*. In another specific embodiment, the KARI is encoded by SEQ ID NO: 3. In yet some embodiments, the KARI is derived from the genus *Eggerthella*. In a specific embodiment, the KARI is derived from *Eggerthella lenta*. In another specific embodiment, the KARI is encoded by SEQ ID NO: 5, SEQ ID NO: 7, SEQ ID NO: 9, SEQ ID NO: 89, SEQ ID NO: 91, or SEQ ID NO: 93. In yet some embodiments, the KARI has one or more modifications or mutations at positions corresponding to amino acids selected from: (a) tyrosine 35 of the *S. exigua* KARI (SEQ ID NO: 2); (b) leucine 57 of the *S. exigua* KARI (SEQ ID NO: 2); (c) arginine 58 of the *S. exigua* KARI (SEQ ID NO: 2); (d) glycine 60 of the *S. exigua* KARI (SEQ ID NO: 2); (e) serine 61 of the *S. exigua* KARI (SEQ ID NO: 2); (f) serine 62 of the *S. exigua* KARI (SEQ ID NO: 2); (g) serine 63 of the *S. exigua* KARI (SEQ ID NO: 2); (h) isoleucine 95 of the *S. exigua* KARI (SEQ ID NO: 2); and (i) valine 99 of the *S. exigua* KARI (SEQ ID NO: 2).

In an exemplary embodiment, the KARI-requiring biosynthetic pathway is a pathway for the production of a metabolite selected from isobutanol, isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol. In a further exemplary embodiment, the beneficial metabolite is isobutanol.

In a method to produce a beneficial metabolite (e.g., isobutanol) from a carbon source, the recombinant microorganism is cultured in an appropriate culture medium containing a carbon source. In certain embodiments, the method further includes isolating the beneficial metabolite (e.g., isobutanol) from the culture medium. For example, a beneficial metabolite (e.g., isobutanol) may be isolated from the culture medium by any method known to those skilled in the art, such as distillation, pervaporation, or liquid-liquid extraction. In certain exemplary embodiments, the beneficial metabolite is selected from isobutanol, isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol. In a further exemplary embodiment, the beneficial metabolite is isobutanol.

In some embodiments, the recombinant microorganism may produce the beneficial metabolite (e.g., isobutanol) from a carbon source at a yield of at least 5 percent theoretical. In some embodiments, the microorganism may produce the beneficial metabolite (e.g., isobutanol) from a carbon source at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, or at least about 97.5% theoretical. In a specific embodiment, the beneficial metabolite is isobutanol.

Distillers Dried Grains Comprising Spent Yeast Biocatalysts

In an economic fermentation process, as many of the products of the fermentation as possible, including the co-products that contain biocatalyst cell material, should have value. Insoluble material produced during fermentations using grain feedstocks, like corn, is frequently sold as protein and vitamin rich animal feed called distillers dried grains (DDG). See, e.g., commonly owned and co-pending U.S. Publication No. 2009/0215137, which is herein incorporated by reference in its entirety for all purposes. As used herein, the term "DDG" generally refers to the solids remaining after a fermentation, usually consisting of unconsumed feedstock solids, remaining nutrients, protein, fiber, and oil, as well as spent yeast biocatalysts or cell debris therefrom that are recovered by further processing from the fermentation, usually by a solids separation step such as centrifugation.

Distillers dried grains may also include soluble residual material from the fermentation, or syrup, and are then referred to as "distillers dried grains and solubles" (DDGS). Use of DDG or DDGS as animal feed is an economical use of the spent biocatalyst following an industrial scale fermentation process.

Accordingly, in one aspect, the present invention provides an animal feed product comprised of DDG derived from a fermentation process for the production of a beneficial metabolite (e.g., isobutanol), wherein said DDG comprise a spent yeast biocatalyst of the present invention. In an exemplary embodiment, said spent yeast biocatalyst has been engineered to comprise at least one nucleic acid molecule encoding a KARI that is at least about 60% identical to SEQ ID NO: 2 and/or SEQ ID NO: 12. In some embodiments, the KARI is derived from the genus *Slackia*. In a specific embodiment, the KARI is derived from *Slackia exigua*. In another specific embodiment, the KARI is encoded by SEQ ID NO: 1. In some embodiments, the KARI is derived from the genus *Cryptobacterium*. In a specific embodiment, the KARI is derived from *Cryptobacterium curtum*. In another specific embodiment, the KARI is encoded by SEQ ID NO: 3. In yet some embodiments, the KARI is derived from the genus *Eggerthella*. In a specific embodiment, the KARI is derived from *Eggerthella lenta*. In another specific embodiment, the KARI is encoded by SEQ ID NO: 5, SEQ ID NO: 7, SEQ ID NO: 9, SEQ ID NO: 89, SEQ ID NO: 91, or SEQ ID NO: 93. In yet some embodiments, the KARI has one or more modifications or mutations at positions corresponding to amino acids selected from: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i)

glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

In certain additional embodiments, the DDG comprising a spent yeast biocatalyst of the present invention comprise at least one additional product selected from the group consisting of unconsumed feedstock solids, nutrients, proteins, fibers, and oils.

In another aspect, the present invention provides a method for producing DDG derived from a fermentation process using a yeast biocatalyst (e.g., a recombinant yeast microorganism of the present invention), said method comprising: (a) cultivating said yeast biocatalyst in a fermentation medium comprising at least one carbon source; (b) harvesting insoluble material derived from the fermentation process, said insoluble material comprising said yeast biocatalyst; and (c) drying said insoluble material comprising said yeast biocatalyst to produce the DDG.

In certain additional embodiments, the method further comprises step (d) of adding soluble residual material from the fermentation process to said DDG to produce DDGS. In some embodiments, said DDGS comprise at least one additional product selected from the group consisting of unconsumed feedstock solids, nutrients, proteins, fibers, and oils.

This invention is further illustrated by the following examples that should not be construed as limiting. The contents of all references, patents, and published patent applications cited throughout this application, as well as the Figures and the Sequence Listing, are incorporated herein by reference for all purposes.

Example 1—Protein Engineering of a
NADH-Dependent Ketol Acid Reductoisomerase
from *Slackia exigua* (Se1_NKR)

As described in US Patent Publication No. 2010/0143997, which is incorporated herein in its entirety for all purposes, NADH-dependent ketol-acid reductoisomerases (NKRs) are desirable in the context of biosynthetic pathways for the production of useful fuels or chemicals, including isobutanol. This example identifies variants of *S. exigua* KARI that show increased enzymatic activity.

Materials and Methods for Example 1

In this example, different KARI variant enzymes were screened for their activity with NADH as cofactor. The enzymes were expressed *E. coli*, and resulting transformants were cultivated in shake flask fermentations as described below and samples were taken after 44 h, centrifuged at 4000×g for 10 mins at 4° C. and the cell pellets were stored at −80° C. until analysis. The pellets were lysed by bead beating and the lysates were analyzed by KARI activity assay as described below using NADH and NADPH as cofactors.

KARI Enzyme Assay: The assay and no substrate control reactions were performed in triplicate for each sample. The following stock solutions were prepared: 1 M potassium phosphate, pH 7, 0.1 M $MgCl_2$, 100 mM DTT, 25 mM NADH, 200 mM 2-acetolactate. The 2-acetolactate was made fresh each time by mixing 50 μL Ethyl-2-acetoxy-2-methylacetoacetate (EAMAA) with 990 μL water. Gradually 260 μL of 2 N NaOH was added in 10 μL increments to the EAMAA water mixture. After each addition the sample was vortexed for 15 seconds, and the procedure repeated until the entire 260 μL of 2 N NaOH was added. Afterwards the solution was mixed on an orbital shaker for 20 min (Krampitz, 1957). KARI reaction buffer (100 μL per reaction) was prepared to the following concentrations: 250 mM potassium phosphate, pH 7, 10 mM MgCl₂, 1 mM DTT, 0.2 mM NADH, 10 mM 2-acetolactate. For the no substrate controls, the 2-acetolactate was substituted with water. 10 µL of each lysate were transferred into a 96 well half area assay plate. The reaction was started with 90 µL of reaction buffer to each well using a multichannel pipette. The samples were mixed immediately. The samples were read at 340 nm every 10 s for 5 min.

Results: Eleven SSM libraries were screened with the NADH$_{km50}$ assay to identify mutations in Se1_NKR that improved activity. In total, 210 variants were rested with NADH$_{km50}$ and NADH$_{Kcat}$ (except Gln330 which was screened with NADH$_{Kcat}$), and performance improving amino acid exchanges for six of eleven positions were found.

Figure 10:
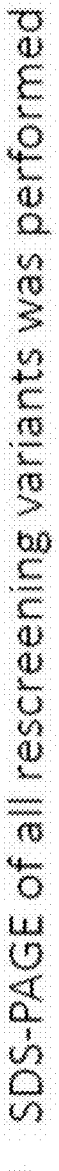
FIG. 10 illustrates the variants identified herein display bands of similar sizes and as observed for other NKR variants.
Figure 11:
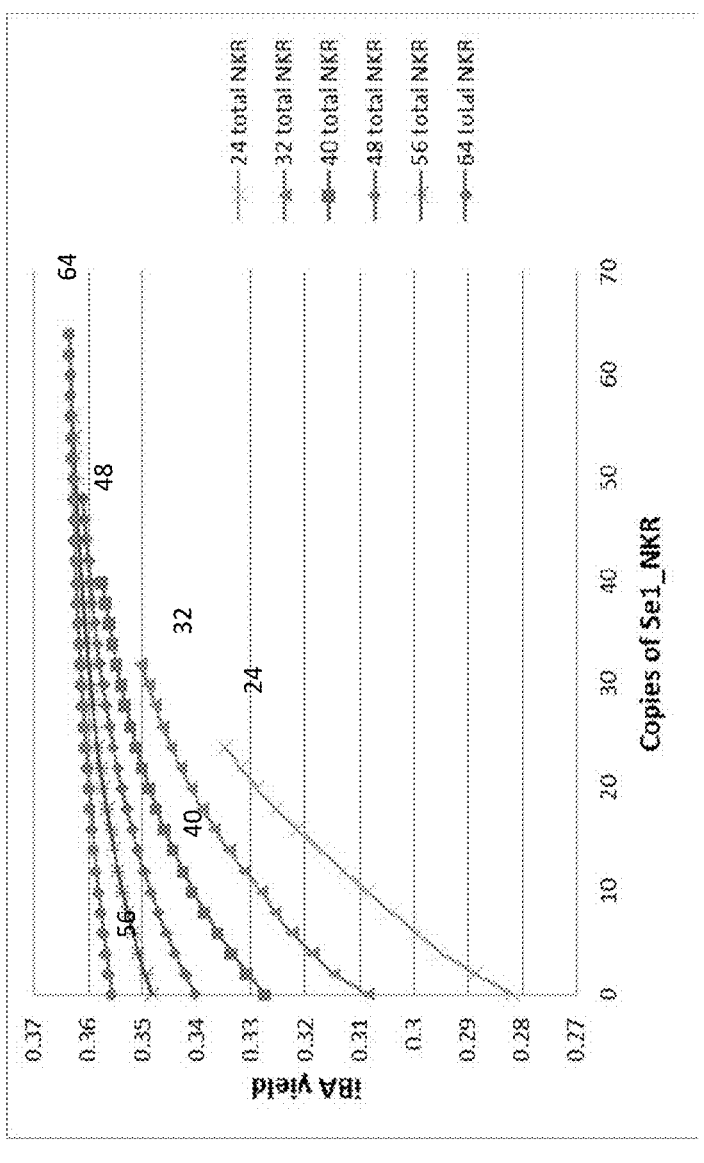
FIG. 11 illustrates Isobutanol yield for a given number of integrated copies of NKR.

Screening was performed at 33° C. For NADH$_{Km50}$, the substrate concentration was 50% of Se1 NKR$_{Km50}$ and in NADH$_{Kcat}$, a substrate concentration of 30×Km and a product concentration at Ki (1.7 mM) was used. After screening evaluation, variants with the highest activity improvements were chosen for sequencing. The overall strategy is shown in FIG. 3. FIGS. 4-9 show the results from amino acid substitutions at various amino acid residues. The exchanges showing the best improvements in activity are: Met77Ile, Val91Ile, Glu94Cys, Gly31Ala, Gly31Cys, Lys290Ala, Lys290Leu, and Gln330Arg. FIG. 10 shows that all these improved-activity variants displayed bands of similar sizes as observed for other variants.

TABLE 2

Se1_NKR variants identified in screening for improved NKR activity

| Position | Variants rescreened | AA exchanges | Best AA exchange | NADKkm50 performance | NADHkcat performance |
|---|---|---|---|---|---|
| Gly31 | 14 | Ala/Cys | Cys | ++ | = |
| Met77 | 27 | Ile/Val/Leu | Ile | (+) | ++ |
| Val91 | 5 | Ile | Ile | = | + |
| Glu94 | 5 | Cys | Cys | (−) | + |
| Tyr126 | 8 | — | — | | |
| Gln150 | 21 | Tyr/WT | — | | |
| Gln165 | 9 | Ser/WT | — | | |
| Lys290 | 18 | Arg/Ala/Leu | Ala | = | + |
| Gln293 | 15 | WT/Arg/Lys | — | | |
| Gln299 | 25 | — | — | | |
| Gln330 | 63 | Arg/Lys | Arg | = | +++ |

Example 2—Genome Scale Metabolic Modeling to Predict the Effect of NKR on Isobutanol Yield This example demonstrates a metabolic model used to investigate the effects of NKR copy number, enzyme type, and improvement of enzyme parameters through protein engineering on isobutanol yield in yeast strains.

The iMM904 metabolic reconstruction of *S. cerevisiae* metabolism served as the basis of the model. The model consists of a matrix of stoichiometric coefficients that represent metabolic and transport reactions encoded by 904 genes. Reactions were added as new columns to the matrix while new rows were added for additional metabolites. The native pathway for making isobutanol in the yeast mitochondria was turned off. A summary of these changes is found in Table 2 below. With these changes made, the maximum isobutanol yield from glucose in the model was approximately 0.38 g/g. If the model was altered to not produce glycerol, the yield increased to 0.41 g/g.

TABLE 3

List of reactions added or deleted and metabolites that were added to the iMM904 genome scale reconstruction of *S. cerevisiae* to enable modeling of isobutanol producing yeast strains

| Reactions Added | Reactions deleted | Metabolites added |
|---|---|---|
| ALD6 | PDC | isobutyrate |
| KIVD | Mitochondrial ADH to isobutanol | 2,3-dihydroxyisovalerate |
| DHAD | | 2-acetolactate |
| NKR | | diacetyl |
| 2-AL decarboxylation to diacetyl | | |
| 2-AL decarboxylation to acetoin | | |
| DAR | | |
| ALS | | |

With more reactions than metabolites, metabolic networks have a near infinite number of solutions for any given condition. In flux balance analysis, the flux distribution is obtained by finding the solution that maximizes an objective function. The objective is typically growth, but for isobutanol producing yeast strains, maximizing for growth does not capture what is observed in lab fermenters. Each flux is bounded by known limits of each reaction, though the bounds are mostly set by thermodynamic reversibility. The bounds of glucose uptake were set in the model according to data for the maximum rate of substrate uptake. As they are assumed to be present in excess, other nutrients in the media are unbounded and allowed to be utilized as needed to metabolize the glucose. The model was then solved for the flux distribution that maximizes biomass and isobutanol production.

To simulate batch cultures, mass balances on key metabolites (glucose, biomass, isobutanol, ethanol, and glycerol) were added to the model to track uptake and production. Production conditions are estimated in the below simulations by setting the initial glucose concentration to 260 g/L and yeast biomass to 3 g/L. Each batch simulation ran for 48 hour fermentation time.

While all other reactions in the isobutanol pathway were set by reversibility only, the upper bound of flux through NKR ($v_{nkr}$) was set by the kinetics of Se1 and Se2_NKR. Flux was calculated by the following equation:

$$v_{nkr} = nNKR * k_{cat} * \frac{AL}{K_m + AL} * \left( \frac{1}{1 + \frac{DHIV}{K_{iDHIV}}} \right)$$

Where nNKR is the number of copies of NKR integrated into the yeast genome, $k_{cat}$ is the first order rate constant, AL is the cytosolic concentration of acetolactate, $K_m$ is the Michaelis constant for acetolactate, DHIV is the concentration of DHIV, and $K_{iDHIV}$ is the inhibition constant for DHIV. The parameters for Se1_NKR and Se2_NKR are set to the following: $K_m$ for Acetolactate=0.43 mM, $K_{iDHIV}$=1.1 mM, $k_{cat}$=2.6 s-1 for Se1_NKR and $K_m$ for Acetolactate=1.1 mM, $K_{iDHIV}$=0.1 mM, $k_{cat}$=4.4 s-1 for Se2_NKR. This also assumes that all copies of NKR are expressed equally regardless of promotor or where it is integrated in the genome.

To determine whether it is more beneficial to have Se1_NKR, Se2_NKR or a combination of both enzymes, simulations were run with a fixed copy number of NKR where the proportion of each enzyme was varied. In each case, Se1_NKR provided a higher isobutanol yield. From the parameters used for the simulation, it is clear that the $K_m$ of Se1_NKR being an order of magnitude less than that of Se2_NKR conveys a large advantage to this enzyme.

TABLE 4

Predicted Isobutanol yields for strains with 24-64 copies of Se1 or Se2 NKR

|  | Se1_NKR | | Se2_NKR | |
| --- | --- | --- | --- | --- |
|  | yield (g/g) | % yield improvement | yield (g/g) | % yield improvement |
| 24 | 0.335 |  | 0.282 |  |
| 32 | 0.350 | 4.662 | 0.308 | 9.476 |
| 40 | 0.357 | 2.050 | 0.327 | 6.153 |
| 48 | 0.361 | 0.988 | 0.340 | 3.920 |
| 56 | 0.363 | 0.486 | 0.348 | 2.355 |
| 64 | 0.363 | 0.215 | 0.356 | 2.155 |

Figure 12:
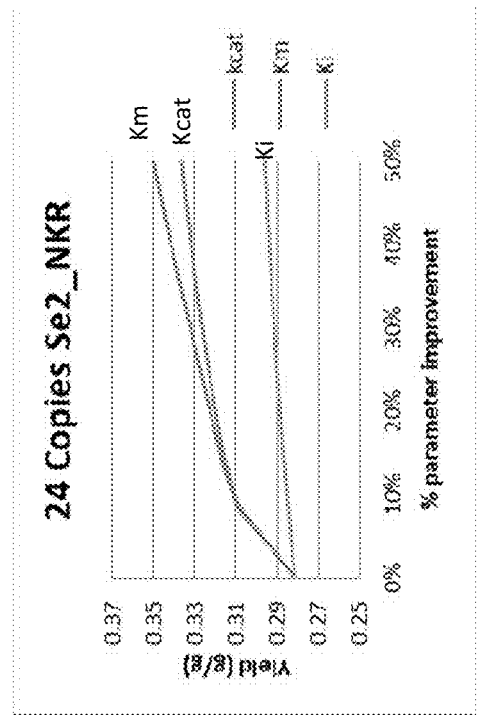
FIG. 12 illustrates the effect of improving parameters of Se1 or Se2_NKR on isobutanol yield in a strain containing 24 integrated copies of the enzyme.
Figure 12:
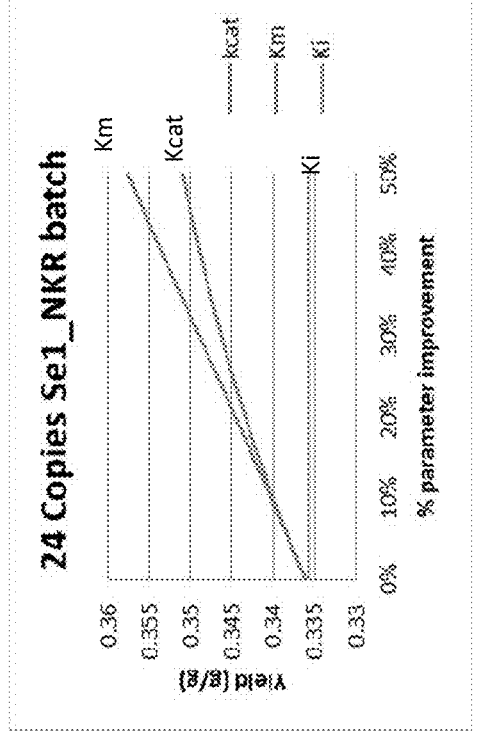

Another round of simulations concerned the improvement of the NKR enzymes through protein engineering. Improvement was simulated by iteratively improving the kinetic parameters for each NKR and calculating the isobutanol yield. Parameters were improved by increasing $k_{cat}$ and $K_{iDHIV}$ and a decreasing $K_m$ by a percentage of the native value. The results of these simulations are plotted in FIG. 12. For both enzymes, the yield is most sensitive to an improvement in $K_m$. Improving the $K_{iDHIV}$ of Se1_NKR up to 50% has a minimal impact on yield, while a 50% improvement for the same parameter in Se2_NKR increased yield from ~0.28 to ~0.30 g/g. A 33% improvement to Se1_NKR $K_m$ is equivalent to adding 8 additional copies of the enzyme. An 8% improvement to Se2_NKR is equivalent to adding 8 copies of that enzyme. The $K_m$ of Se2_NKR would have to be improved by 33% or the $k_{cat}$ by 50% to match the yield of an equal number of Se1_NKR enzymes.

Figure 13:
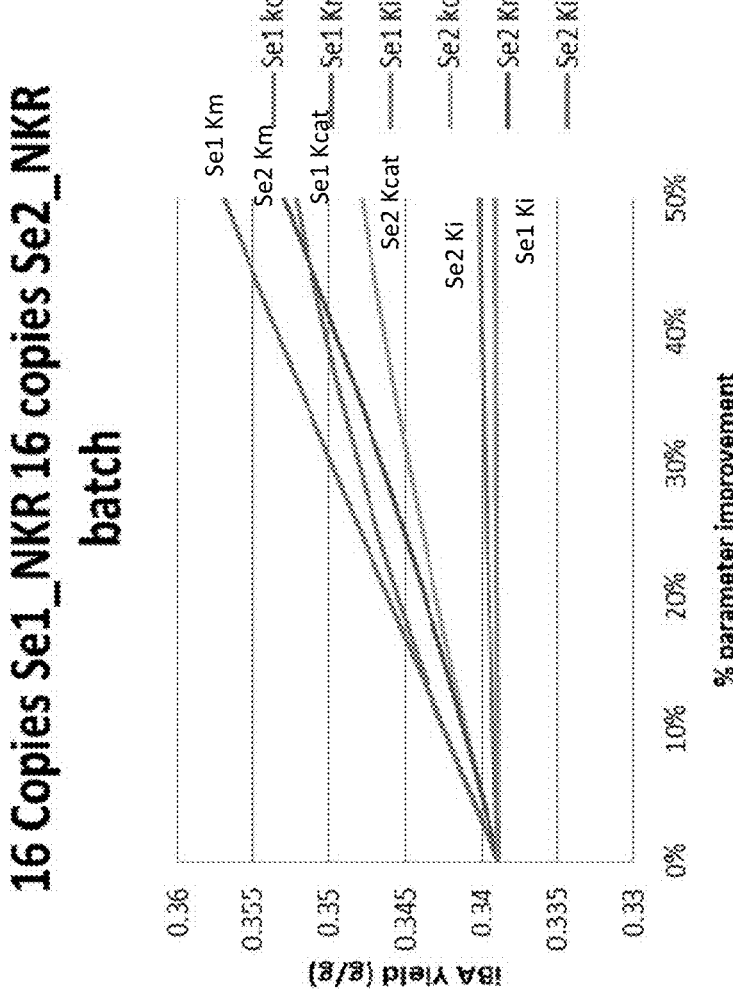
FIG. 13 demonstrates results from modelling the effect of parameter improvement on isobutanol yield in a strain with 16 copies of Se1_NKR and 16 copies of Se2_NKR.

The benefits of improving either NKR enzyme in a strain with an equal number of both was calculated to predict which enzyme was best to engineer. The results are shown in FIG. 13. In this example, improvement to the $K_m$ of Se1_NKR has the greatest effect on isobutanol yield. Up until a 45% improvement, the $k_{cat}$ of Se1_NKR provides the second best improvement on yield. If the $K_m$ of Se2_NKR can be improved by over 45%, it will provide the second best improvement. Although the parameters of the current version of Se1_NKR are better than that of Se2_NKR, engineering small improvements to Se1_NKR parameters should have a larger effect on yield than Se2_NKR engineering.

CONCLUSIONS a. According the measured parameters for Se1 and Se2_NKR, the Se1 enzyme allows for a greater flux.

b. Adding 8-10 additional copies of Se1_NKR to the current best fully-integrated strain (19629-16 copies of Se1_NKR, 32 copies of Se2_NKR) will reach a yield of 0.36 g/g. Alternatively, the model predicts the same result can be obtained by replacing 16 copies of Se2_NKR with Se1_NKR.

c. Isobutanol yield is most sensitive to the $K_m$ of either NKR enzyme d. Although improving the Se2_NKR through protein engineering is predicted to be more efficient at replacing the number of copies needed to achieve the same yield, improving Se1_NKR parameters had a larger impact on isobutanol yield in a hypothetical strain containing both enzymes.

Example 3— Protein Engineering of a NADH-Dependent Ketol Acid Reductoisomerase from *Slackia exigua* (Se1_NKR_Gen6)

Materials and Methods for Example 3

In this example, three different KARI Gen6 variant enzymes (v1, v48, and v65) and parent enzyme Se1_NKR_gen6 were screened for their activity with NADH as cofactor. The enzymes were expressed *E. coli*, and resulting transformants were cultivated in shake flask fermentations as described below and samples were taken after 44 h, centrifuged at 4000×g for 10 mins at 4° C. and the cell pellets were stored at −80° C. until analysis. The pellets were lysed by bead beating and the lysates were analyzed by KARI activity assay as described below using NADH and NADPH as cofactors.

KARI Enzyme Assay: The assay and no substrate control reactions were performed in triplicate for each sample. For the $K_M$ assay, the reaction samples comprised 100 mM potassium phosphate, pH 6.8 or 7, 10 mM $MgCl_2$, 1 mM DTT, 200 μM NADH, 0-10 mM 2-acetolactate, and 0.1 mg/mL of enzyme. For the Ki assay, the reaction samples comprised 100 mM potassium phosphate, pH 6.8 or 7, 10 mM $MgCl_2$, 1 mM DTT, 200 μM NADH, 1 mM 2-acetolactate, 0-40 mM R-DHIV, and 0.1 mg/mL of enzyme. For the no substrate controls, the 2-acetolactate was substituted with water. 10 μL of each lysate were transferred into a 96 well half area assay plate. The reaction was started with 90 μL of reaction buffer to each well using a multichannel pipette. The samples were mixed immediately. The samples were read at 340 nm every 10 seconds for 5 minutes.

Results:

The purified enzymes encoded by Se1_NKR_Gen6 (Se1), Se1_NKR_v1 (v1), Se1_NKR_v48 (v48), and Se1_NKR_v65 (v65) under two conditions: 33° C. at pH 6.8 and 30° C. at pH 7 were characterized. Table 5 summarizes the data.

TABLE 5

|  | Mutations | $K_M$ [mM] | $K_i$ [mM] | Kcat (1/s) | $IC_{50}$ [mM] | $V_{max}$ (mM/ sec) | Catalytic Efficiency (kcat/kM) |
| --- | --- | --- | --- | --- | --- | --- | --- |
| | | 33° C., pH 6.8 | | | | | |
| Se1 | — | 0.419 | 0.768 | 382 | 2.60 | 1.12 | 911.69 |
| V1 | M77I, V91I, K290A, Q330N | 0.407 | 0.834 | 491 | 2.88 | 1.45 | 1206.39 |
| V48 | G31A, M77I, Q330N | 0.533 | 1.054 | 647 | 3.03 | 1.90 | 1213.88 |
| V65 | G31A, V91I, Q330N | 0.510 | 0.801 | 538 | 2.37 | 1.58 | 1054.90 |
| | | 30° C., pH 7 | | | | | |
| Se1 | — | 0.711 | 0.752 | 442 | 1.81 | 1.30 | 621.66 |
| V1 | M77I, V91I, K290A, Q330N | 0.566 | 0.832 | 555 | 2.30 | 1.63 | 980.57 |
| V48 | G31A, M77I, Q330N | 0.683 | 0.996 | 717 | 2.45 | 2.11 | 1049.78 |

TABLE 5-continued

| Mutations | | $K_M$ [mM] | $K_i$ [mM] | Kcat (1/s) | $IC_{50}$ [mM] | $V_{max}$ (mM/ sec) | Catalytic Efficiency (kcat/kM) |
|---|---|---|---|---|---|---|---|
| V65 | G31A, V91I, Q330N | 0.673 | 0.821 | 602 | 2.04 | 1.77 | 894.50 |

The three variants showed different levels of improvement compared to Se1_NKR under the two conditions. Generally, Se1_NKR_v1 demonstrated the best (lowest) $K_M$ for acetolactate, whereas Se1_NKR_v48 had the best (highest) Ki for DHIV and rate ($k_{cat}$ or $V_{MAX}$). In terms of catalytic efficiency ($k_{cat}/K_M$), Se1_NKR_v48 was the best variant in both cases.

Figure 14A:
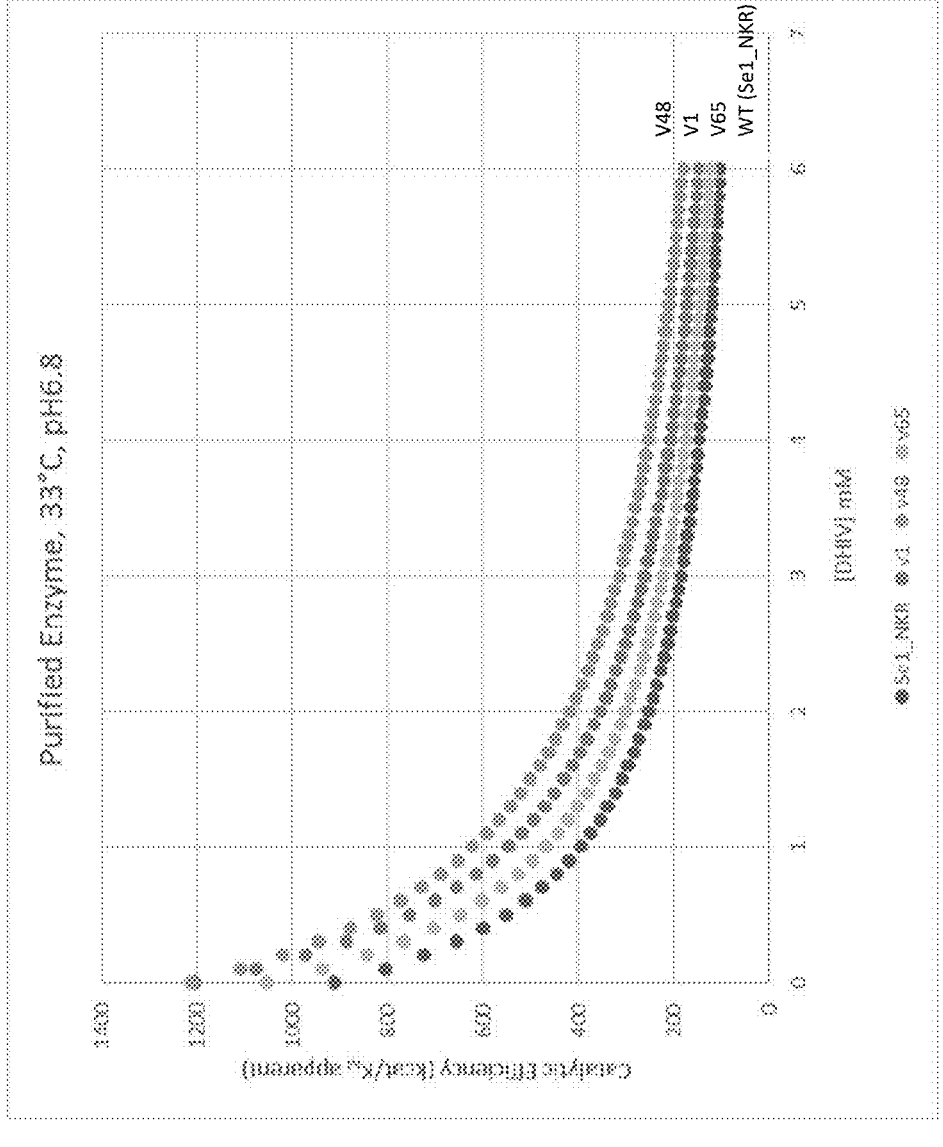
FIG. 14A-B demonstrates the effect of increasing concentrations of product (DHIV) on the catalytic efficiency of the v1, v48, and v65 NKR enzyme variants at 33° C., pH 6.8 (Panel A) and 30° C., pH 7.0 (Panel B).
Figure 14B:
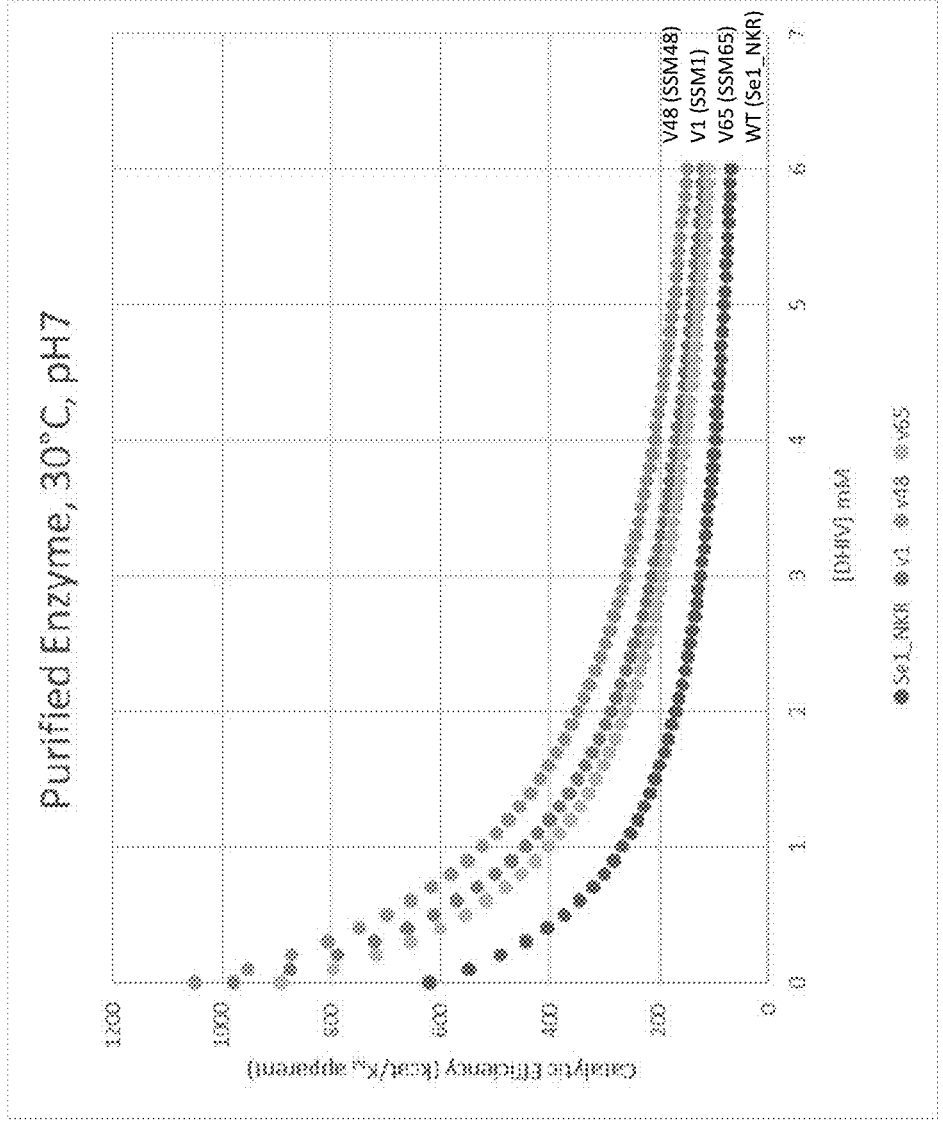

In terms of product inhibition, Se1_NKR_v48 also demonstrated the best (highest) $K_I$ for DHIV. In order to determine the impact of all three parameters ($k_{cat}$, $K_M$, and $K_I$) to more closely determine the impact of the new variants in vivo, the catalytic efficiency for each enzyme using the $K_M$ apparent, which is equal to $K_M*(1+[product]/K_I)$, was calculated. FIG. 14A-B shows a plot of catalytic efficiency versus increasing concentrations of product (DHIV). Under both conditions, v48 demonstrates the highest catalytic efficiencies as the concentration of DHIV increases, with v1 and v65 showing decreasing catalytic efficiencies. However, all three enzymes are superior to the parent enzyme, se1_NKR. Previous data for intracellular concentrations of DHIV suggest 1 mM may be present internally. At this DHIV concentration level, in vivo, at 33° C., pH 6.8, m48 would be 157%, Se1_NKR_v1 would be 139%, and Se1_NKR_v65 would be 118% improved compared to Se1_NKR. For example, in vivo, cells expressing Se1_NKR-v48, it would be expected that 16 fewer copies of the enzyme could potentially achieve 36% less protein while achieving 0.35 g/g yeast efficiency.

Isobutanol Production

Table 6 shows the final relative isobutanol concentrations in a simple shake flast fermentation with the Se1_NKR (WT) or one of the variants described in this eample. All three of the variants had higher isobutanol concentrations, with Se1_NKR_v1 producing significantly more isobutanol than the WT enzyme. This improvement in isobutanol production is expected to increase with multiple copies of the Se1_NKR_v1 variant enzyme incorporated into the host cell genome.

TABLE 6

| | Isobutanol Concentration relative to Se1_NKR control (WT) |
|---|---|
| Control—empty vector | 49% |
| Control—Se1_NKR on vector | 100% |
| Se1_NKR_v1 on vector | 105% |
| Se1_NKR_v48 on vector | 104% |
| Se1_NKR_v65 on vector | 103% |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

EMBODIMENTS

Embodiment 1: A recombinant microorganism comprising at least one nucleic acid molecule encoding a ketol-acid reductoisomerase (KARI), wherein said KARI is at least about 60% identical to SEQ ID NO: 2.

Embodiment 2: The recombinant microorganism of embodiment 1, wherein said KARI is derived from the genus *Slackia*.

Embodiment 3: The recombinant microorganism of embodiments 1-2, wherein said KARI is derived from *Slackia exigua*.

Embodiment 4: The recombinant microorganism of any of the preceding embodiments, wherein said KARI is encoded by SEQ ID NO: 1.

Embodiment 5: The recombinant microorganism of embodiment 1, wherein said KARI is derived from the genus *Cryptobacterium*.

Embodiment 6: The recombinant microorganism of embodiment 5, wherein said KARI is derived from *Cryptobacterium curtum*.

Embodiment 7: The recombinant microorganism of any of embodiments 5-6, wherein said KARI is encoded by SEQ ID NO: 3.

Embodiment 8: The recombinant microorganism of embodiment 1, wherein said KARI is derived from the genus *Eggerthella*.

Embodiment 9: The recombinant microorganism of embodiment 8, wherein said KARI is derived from *Eggerthella lenta*.

Embodiment 10: The recombinant microorganism of any of embodiments 8-9, wherein said KARI is encoded by SEQ ID NO: 5, SEQ ID NO: 7, SEQ ID NO: 9, SEQ ID NO: 89, SEQ ID NO: 91, or SEQ ID NO: 93.

Embodiment 11: The recombinant microorganism of embodiment 1, wherein said KARI is modified to be an NADH-dependent ketol acid reductoisomerase.

Embodiment 12: An isolated nucleic acid molecule encoding a ketol-acid reductoisomerase (KARI), wherein said KARI is at least about 60% identical to SEQ ID NO: 2.

Embodiment 13: The isolated nucleic acid molecule of embodiment 12, wherein said KARI is derived from the genus *Slackia*.

Embodiment 14: The isolated nucleic acid molecule of embodiment 13, wherein said KARI is derived from *Slackia exigua*.

Embodiment 15: The isolated nucleic acid molecule of any of embodiments 12-14, wherein said isolated nucleic acid molecule is comprised of SEQ ID NO: 1.

Embodiment 16: The isolated nucleic acid molecule of embodiment 12, wherein said KARI is derived from the genus *Cryptobacterium*.

Embodiment 17: The isolated nucleic acid molecule of embodiment 16, wherein said KARI is derived from *Cryptobacterium curtum*.

Embodiment 18: The isolated nucleic acid molecule of any of embodiments 16-17, wherein said isolated nucleic acid molecule is comprised of SEQ ID NO: 3.

Embodiment 19: The isolated nucleic acid molecule of embodiment 12, wherein said KARI is derived from the genus *Eggerthella*.

Embodiment 20: The isolated nucleic acid molecule of embodiment 19, wherein said KARI is derived from *Eggerthella lenta*.

Embodiment 21: The isolated nucleic acid molecule of any of embodiments 19-20, wherein said isolated nucleic acid molecule is comprised of SEQ ID NO: 5, SEQ ID NO: 7, SEQ ID NO: 9, SEQ ID NO: 89, SEQ ID NO: 91, or SEQ ID NO: 93.

Embodiment 22: The isolated nucleic acid molecule of embodiment 12, wherein said isolated nucleic acid has been modified to encode a polypeptide having NADH-dependent ketol acid reductoisomerase activity.

Embodiment 23: A recombinant microorganism comprising the isolated nucleic acid of any of embodiments 12-22.

Embodiment 24: A mutant ketol-acid reductoisomerase (KARI) comprising one or more mutations or modifications at positions corresponding to amino acids selected from the group consisting of: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

Embodiment 25: The mutant KARI of embodiment 24, wherein said glycine 31 is replaced with a residue selected from alanine and cysteine.

Embodiment 26: The mutant KARI of embodiment 24, wherein said methionine 77 is replaced with a residue selected from isoleucine, valine, and leucine.

Embodiment 27: The mutant KARI of any one of embodiments 25-26, wherein said valine 91 is replaced with an isoleucine residue.

Embodiment 28: The mutant KARI of any one of embodiments 25-27, wherein said glutamic acid 94 is replaced with a cysteine residue.

Embodiment 29: The mutant KARI of any one of embodiments 25-28, wherein said glutamine 150 is replaced with a tyrosine residue.

Embodiment 30: The mutant KARI of any one of embodiments 25-29, wherein said lysine 290 is replaced with a residue selected from arginine, alanine, and leucine.

Embodiment 31: The mutant KARI of any one of embodiments 25-30, wherein said glutamic acid 293 is replaced with a residue selected from arginine and lysine.

Embodiment 32: The mutant KARI of any one of embodiments 25-31, wherein said glutamic acid 64 is replaced with a residue selected from arginine and lysine.

Embodiment 33: A recombinant microorganism comprising at least one nucleic acid molecule encoding a KARI of any of embodiments 24-32.

Embodiment 34: An isolated nucleic acid molecule encoding a mutant KARI, wherein said mutant KARI comprises one or more mutations or modifications at positions corresponding to amino acids selected from the group consisting of: (a) glycine 31 of the *S. exigua* KARI (Se1_NKR) (SEQ ID NO: 2); (b) methionine 77 of the *S. exigua* KARI (SEQ ID NO: 2); (c) valine 91 of the *S. exigua* KARI (SEQ ID NO: 2); (d) glutamic acid 94 of the *S. exigua* KARI (SEQ ID NO: 2); (e) tyrosine 126 of the *S. exigua* KARI (SEQ ID NO: 2); (f) glutamine 150 of the *S. exigua* KARI (SEQ ID NO: 2); (g) glutamine 165 of the *S. exigua* KARI (SEQ ID NO: 2); (h) lysine 290 of the *S. exigua* KARI (SEQ ID NO: 2); (i) glutamine 293 of the *S. exigua* KARI (SEQ ID NO: 2); (j) glutamine 299 of the *S. exigua* KARI (SEQ ID NO: 2); and (k) glutamine 330 of the *S. exigua* KARI (SEQ ID NO: 2).

Embodiment 35: A recombinant microorganism comprising the isolated nucleic acid of embodiment 34.

Embodiment 36: The recombinant microorganism of any of embodiments 1-11, 23, 33, or 35, wherein said recombinant microorganism further comprises an isobutanol producing metabolic pathway comprising one or more isobutanol metabolic pathway enzymes selected from acetolactate synthase, dihydroxy acid dehydratase, keto-isovalerate decarboxylase, and alcohol dehydrogenase Embodiment 37: The recombinant microorganism of any of embodiments 1-11, 23, 33, or 35, wherein said recombinant microorganism comprises a metabolic pathway for the production of a metabolite selected from the group consisting of isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol.

Embodiment 38: The recombinant microorganism of any of embodiments 1-11, 23, 33, or 35-37, wherein said recombinant microorganism is a yeast microorganism.

Embodiment 39: A method of producing isobutanol, comprising:

a. providing a recombinant microorganism of any of embodiments 37 or 38; and b. cultivating the recombinant microorganism in a culture medium containing a feedstock providing a carbon source, until the isobutanol is produced.

INCORPORATION BY REFERENCE

All patents and publications referenced herein are hereby incorporated by reference in their entireties, including the publications disclosed below.

The publications discussed herein are provided solely for their disclosure prior to the filing date of the present application. Nothing herein is to be construed as an admission that the present disclosure is not entitled to antedate such publication by virtue of prior disclosure.

This application incorporates by reference the following publications in their entireties for all purposes: US 2014/0295512 filed Jun. 15, 2012.

What is claimed is:

1. A recombinant microorganism comprising at least one nucleic acid molecule encoding a ketol-acid reductoisomerase (KARI), wherein said KARI is at least about 98% identical to SEQ ID NO: 90, SEQ ID NO: 92, or SEQ ID NO: 94.

2. The recombinant microorganism of claim 1, wherein said KARI is derived from the genus *Slackia*.

3. The recombinant microorganism of claim 2, wherein said KARI is derived from *Slackia exigua*.

4. The recombinant microorganism of claim 1, wherein said KARI comprises the amino acid sequence of SEQ ID NO: 90, SEQ ID NO: 92, or SEQ ID NO: 94.

5. The recombinant microorganism of claim 1, wherein said KARI is encoded by SEQ ID NO:89, SEQ ID NO: 91, or SEQ ID NO: 93.

6. The recombinant microorganism of claim 1, wherein said KARI is NADH-dependent.

7. The recombinant microorganism of claim 1, wherein said recombinant microorganism further comprises an isobutanol producing metabolic pathway comprising one or more isobutanol metabolic pathway enzymes selected from acetolactate synthase, dihydroxy acid dehydratase, keto-isovalerate decarboxylase, and alcohol dehydrogenase.

8. The recombinant microorganism of claim 1, wherein said recombinant microorganism comprises a metabolic pathway for the production of a metabolite selected from the group consisting of isoleucine, leucine, valine, pantothenate, coenzyme A, 1-butanol, 2-methyl-1-butanol, 3-methyl-1-butanol, 3-methyl-1-pentanol, 4-methyl-1-pentanol, 4-methyl-1-hexanol, and 5-methyl-1-heptanol.

9. The recombinant microorganism of claim 1, wherein said recombinant microorganism is a yeast microorganism.

10. A method of producing isobutanol, comprising:
a. providing a recombinant microorganism of claim 1; and
b. cultivating the recombinant microorganism in a culture medium containing a feedstock providing a carbon source, until the isobutanol is produced.

* * * * *

SEQUENCE LISTING

<160> NUMBER OF SEQ ID NOS: 94

<210> SEQ ID NO 1

```
<211> LENGTH: 1029
<212> TYPE: DNA
<213> ORGANISM: Slackia exigua

<400> SEQUENCE: 1
gtgtcggtca agactaagga gaaagaaatg gctgtcacca tcttgtacga acaggacgtc      60
gatcccaaag tcatacaggg cctcaaggtc ggcatcatcg gctacggctc ccagggccat     120
gcccatgcgc tgaacctcat ggattccggc gtcgacgtgc gcgtcggcct cgcgcgaagga     180 tcctcttcct ggaagaccgc cgaagaggcc ggcctgaagg tcaccgacat ggacaccgcg     240
gccgaagaag ccgacgtcat catggtcctc gtccccgacg agatccagcc gaaggtctac     300
caggagcaca tcgccgcgca cctgaaggca ggcaacacgc tcgccttcgc ccatggcttc     360
aacatccact acggctacat cgtgccgccc gaggacgtca cgtcatcat gtgcgctccc      420 aagggcccgg ggcacatcgt ccgccgtcag ttcaccgaag gttccggcgt gcccgacctg     480
gcctgcgtcc agcaggatgc caccggcaac gcctgggata tcgtcctgtc ctactgctgg     540
ggcgtcggcg gggcccgttc cggcatcatc aaggcgacct cgccgaggga gaccgaggaa     600
gacctcttcg cgagcaggc cgtgctctgc ggaggcctgg tggagctggt caaggccggc      660
ttcgagaccc tgaccgaggc agggtatccg cccgagctgg catacttcga gtgctatcac     720
gagatgaaga tgatcgtcga cctcatgtac gagagcggca tccacttcat gaactactcg     780
atctccaaca ccgccgaata cggcgagtac tacgccggcc cgaaggtcat caacgagcag     840
tcccgcgagg ccatgaagga gatcctgaag cgcattcagg acggctcctt cgcccaggaa     900
ttcgtcgacg actgcaacaa cggccataag cgcctgctcg agcagcgcga agcgatcaat     960
acgcacccca tcgagaccac cggcgcccag atccgcagca tgttctcctg gatcaagaag    1020
gaagactag                                                            1029

<210> SEQ ID NO 2
<211> LENGTH: 342
<212> TYPE: PRT
<213> ORGANISM: Slackia exigua

<400> SEQUENCE: 2

Met Ser Val Lys Thr Lys Glu Lys Glu Met Ala Val Thr Ile Leu Tyr
1               5                   10                  15

Glu Gln Asp Val Asp Pro Lys Val Ile Gln Gly Leu Lys Val Gly Ile
            20                  25                  30

Ile Gly Tyr Gly Ser Gln Gly His Ala His Ala Leu Asn Leu Met Asp
        35                  40                  45

Ser Gly Val Asp Val Arg Val Gly Leu Arg Glu Gly Ser Ser Ser Trp
    50                  55                  60

Lys Thr Ala Glu Glu Ala Gly Leu Lys Val Thr Asp Met Asp Thr Ala
65                  70                  75                  80

Ala Glu Glu Ala Asp Val Ile Met Val Leu Val Pro Asp Glu Ile Gln
                85                  90                  95

Pro Lys Val Tyr Gln Glu His Ile Ala Ala His Leu Lys Ala Gly Asn
            100                 105                 110

Thr Leu Ala Phe Ala His Gly Phe Asn Ile His Tyr Gly Tyr Ile Val
            115                 120                 125

Pro Pro Glu Asp Val Asn Val Ile Met Cys Ala Pro Lys Gly Pro Gly
        130                 135                 140

His Ile Val Arg Arg Gln Phe Thr Glu Gly Ser Gly Val Pro Asp Leu
145                 150                 155                 160
```

```
Ala Cys Val Gln Gln Asp Ala Thr Gly Asn Ala Trp Asp Ile Val Leu
              165                 170                 175

Ser Tyr Cys Trp Gly Val Gly Gly Ala Arg Ser Gly Ile Ile Lys Ala
              180                 185                 190

Thr Phe Ala Glu Glu Thr Glu Glu Asp Leu Phe Gly Glu Gln Ala Val
              195                 200                 205

Leu Cys Gly Gly Leu Val Glu Leu Val Lys Ala Gly Phe Glu Thr Leu
         210                 215                 220

Thr Glu Ala Gly Tyr Pro Pro Glu Leu Ala Tyr Phe Glu Cys Tyr His
225                 230                 235                 240

Glu Met Lys Met Ile Val Asp Leu Met Tyr Glu Ser Gly Ile His Phe
              245                 250                 255

Met Asn Tyr Ser Ile Ser Asn Thr Ala Glu Tyr Gly Glu Tyr Tyr Ala
              260                 265                 270

Gly Pro Lys Val Ile Asn Glu Gln Ser Arg Glu Ala Met Lys Glu Ile
         275                 280                 285

Leu Lys Arg Ile Gln Asp Gly Ser Phe Ala Gln Glu Phe Val Asp Asp
         290                 295                 300

Cys Asn Asn Gly His Lys Arg Leu Leu Glu Gln Arg Glu Ala Ile Asn
305                 310                 315                 320

Thr His Pro Ile Glu Thr Thr Gly Ala Gln Ile Arg Ser Met Phe Ser
              325                 330                 335

Trp Ile Lys Lys Glu Asp
              340
```

<210> SEQ ID NO 3
<211> LENGTH: 996
<212> TYPE: DNA
<213> ORGANISM: Cryptobacterium curtum
<400> SEQUENCE: 3

```
atggctgtca ccatcttgca cgaagaggat gcaaatccag caatcattca aggaaagaaa        60
attgccatta ttgggtatgg ttcacaaggg catgctcatg cgcttaatct gcatgattca       120
ggttgcgatg tacgtgttgg cctgcgccgt gattcatctt cttggaagat cgcagaagag       180
gctggtttga aagttatgac cactgctgaa gcggctcgcg aagccaatgt gattatgatt       240 ttgcacctg atgaaagtca gcgtgcggtg tacgctcaag atattgtccc gcatctgcaa        300
ccaggcgata cgcttgcctt tgcacatgga ttcaacatcc attttggata catcgtgccg       360
cccaaggatg ttaacgtcat catggtggcg ccaaaaggcc ctggtcatat tgtgcgtcgc       420
caatttactg aaggatccgg cgttcctgat cttatctgcg tgcagcaaga ctttaccgag       480
gatgcctggg atattgcctt atcgtatgcg tgggggctcg cggcacgcg cgcggggtt        540 attaagagta cctttaaaga cgaaactgaa gaggatctct ttggcgaaca ggcggtgctc       600
tgcggcgggg ttactcacct gatcgaagca ggatacgaag tgctgactga ggctggctat       660
ccgggtgagt tggcgtattt tgaggtgtac catgaaatga aaatgattgt ggacctcatg       720
tacgaaaacg gtatgcatgg tatgcgtagc tccatttcca atacagctga atatggtgac       780
tattacgctg gtccgcggat tattaccgaa gacaccaagg cagcgatgcg taccattctt       840
gcccgcattc aagatggatc gtttgcgaaa gagtttatcg acgattgcga tcgtggacat       900
gaagtgctgc tgagcaagcg tgctgaatat gcgaaccacg aaatcgaaca ggttggcgaa       960
gaaattcgca acatgtttag ctggatcaaa cgatag                                  996
```

```
<210> SEQ ID NO 4
<211> LENGTH: 331
<212> TYPE: PRT
<213> ORGANISM: Cryptobacterium curtum

<400> SEQUENCE: 4

Met Ala Val Thr Ile Leu His Glu Glu Asp Ala Asn Pro Ala Ile Ile
1               5                   10                  15

Gln Gly Lys Lys Ile Ala Ile Ile Gly Tyr Gly Ser Gln Gly His Ala
            20                  25                  30

His Ala Leu Asn Leu His Asp Ser Gly Cys Asp Val Arg Val Gly Leu
        35                  40                  45

Arg Arg Asp Ser Ser Ser Trp Lys Ile Ala Glu Glu Ala Gly Leu Lys
    50                  55                  60

Val Met Thr Thr Ala Glu Ala Ala Arg Glu Ala Asn Val Ile Met Ile
65                  70                  75                  80

Leu Thr Pro Asp Glu Ser Gln Arg Ala Val Tyr Ala Gln Asp Ile Val
                85                  90                  95

Pro His Leu Gln Pro Gly Asp Thr Leu Ala Phe Ala His Gly Phe Asn
            100                 105                 110

Ile His Phe Gly Tyr Ile Val Pro Pro Lys Asp Val Asn Val Ile Met
        115                 120                 125

Val Ala Pro Lys Gly Pro Gly His Ile Val Arg Arg Gln Phe Thr Glu
    130                 135                 140

Gly Ser Gly Val Pro Asp Leu Ile Cys Val Gln Gln Asp Phe Thr Glu
145                 150                 155                 160

Asp Ala Trp Asp Ile Ala Leu Ser Tyr Ala Trp Gly Leu Gly Gly Thr
                165                 170                 175

Arg Ala Gly Val Ile Lys Ser Thr Phe Lys Asp Glu Thr Glu Glu Asp
            180                 185                 190

Leu Phe Gly Glu Gln Ala Val Leu Cys Gly Gly Val Thr His Leu Ile
        195                 200                 205

Glu Ala Gly Tyr Glu Val Leu Thr Glu Ala Gly Tyr Pro Gly Glu Leu
    210                 215                 220

Ala Tyr Phe Glu Val Tyr His Glu Met Lys Met Ile Val Asp Leu Met
225                 230                 235                 240

Tyr Glu Asn Gly Met His Gly Met Arg Ser Ser Ile Ser Asn Thr Ala
                245                 250                 255

Glu Tyr Gly Asp Tyr Tyr Ala Gly Pro Arg Ile Ile Thr Glu Asp Thr
            260                 265                 270

Lys Ala Ala Met Arg Thr Ile Leu Ala Arg Ile Gln Asp Gly Ser Phe
        275                 280                 285

Ala Lys Glu Phe Ile Asp Asp Cys Asp Arg Gly His Glu Val Leu Leu
    290                 295                 300

Ser Lys Arg Ala Glu Tyr Ala Asn His Glu Ile Glu Gln Val Gly Glu
305                 310                 315                 320

Glu Ile Arg Asn Met Phe Ser Trp Ile Lys Arg
                325                 330

<210> SEQ ID NO 5
<211> LENGTH: 996
<212> TYPE: DNA
<213> ORGANISM: Unknown
<220> FEATURE:
<223> OTHER INFORMATION: Eggerthella sp.
```

```
<400> SEQUENCE: 5
atggctgtta cgatctatca cgagaaagac gcgaacccccc agctcatcca ggacaagaag     60
gtggccatca tcggctacgg cagccagggc cacgcccatg cgctcaacct gctggactcg    120
ggcgtggacg tgcgcgtggg cctgcgcgag gactcgcgct cgcgggccaa ggccgaggag    180
gcgggcctca aggtgatgag cgtcgccgac gctgccgagg aagccgactt catcatgatc    240
ctcacgcccg acgagaccca ggccgccacg tacgaagcgg acatcgcccc gcatctcaag    300
gccggcgaca cgctggcgtt cgcgcacggc ttcaacatcc acttcggcta catcgagccg    360
cccgcggacg tcgatgtggt catgatcgcg ccgaagggcc cgggccacat ggtgcgccgc    420
gtgttcaccg aaggcgcggg cgtgccgtgc ctcatctgcg tgaaccagga cgcgtcgggt    480
gcggccaagg atgtggcgct gtcgtacgcg tggggcatcg gcggcgcacg cgccggcgtc    540
atcgagacca cgttcaagaa cgagaccgaa accgacctgt cggcgagca ggccgtgctg    600 tgcggcggcg tgacggcgct catcaacgcc ggcttcgaga cgctggtgga ggcgggctat    660
ccgcccgaga tggcctactt cgagtgcttc cacgagatga agctcatcgt ggacctcatg    720
tacgagggcg gcatgtcgaa catgcgctac tccatctcga acacggccga gtacggcgac    780
tactacgccg gcccgcaggt gatcaccgac gagacgaagg ccgcgatgaa gaccgtgctg    840
gcgcgcatcc aggacggcag cttcgcccac gagttcatgg aggactcgaa gaacggccag    900
aagtggctca agagcagcg catggagcac ggcaacgccc agatcgagga gtgggcgcc    960 aacatccgct cgatgttcag cttcgtgagg aggtag                                996

<210> SEQ ID NO 6
<211> LENGTH: 331
<212> TYPE: PRT
<213> ORGANISM: Unknown
<220> FEATURE:
<223> OTHER INFORMATION: Eggerthella sp.

<400> SEQUENCE: 6

Met Ala Val Thr Ile Tyr His Glu Lys Asp Ala Asn Pro Gln Leu Ile
1               5                   10                  15

Gln Asp Lys Lys Val Ala Ile Ile Gly Tyr Gly Ser Gln Gly His Ala
                20                  25                  30

His Ala Leu Asn Leu Leu Asp Ser Gly Val Asp Val Arg Val Gly Leu
            35                  40                  45

Arg Glu Asp Ser Arg Ser Arg Ala Lys Ala Glu Glu Ala Gly Leu Lys
        50                  55                  60

Val Met Ser Val Ala Asp Ala Ala Glu Glu Ala Asp Phe Ile Met Ile
65                  70                  75                  80

Leu Thr Pro Asp Glu Thr Gln Ala Ala Thr Tyr Glu Ala Asp Ile Ala
                85                  90                  95

Pro His Leu Lys Ala Gly Asp Thr Leu Ala Phe Ala His Gly Phe Asn
            100                 105                 110

Ile His Phe Gly Tyr Ile Glu Pro Pro Ala Asp Val Asp Val Val Met
        115                 120                 125

Ile Ala Pro Lys Gly Pro Gly His Met Val Arg Arg Val Phe Thr Glu
    130                 135                 140

Gly Ala Gly Val Pro Cys Leu Ile Cys Val Asn Gln Asp Ala Ser Gly
145                 150                 155                 160

Ala Ala Lys Asp Val Ala Leu Ser Tyr Ala Trp Gly Ile Gly Gly Ala
                165                 170                 175
```

-continued

---

Arg Ala Gly Val Ile Glu Thr Thr Phe Lys Asn Glu Thr Glu Thr Asp
                180                 185                 190

Leu Phe Gly Glu Gln Ala Val Leu Cys Gly Gly Val Thr Ala Leu Ile
            195                 200                 205

Asn Ala Gly Phe Glu Thr Leu Val Glu Ala Gly Tyr Pro Pro Glu Met
        210                 215                 220

Ala Tyr Phe Glu Cys Phe His Glu Met Lys Leu Ile Val Asp Leu Met
225                 230                 235                 240

Tyr Glu Gly Gly Met Ser Asn Met Arg Tyr Ser Ile Ser Asn Thr Ala
                245                 250                 255

Glu Tyr Gly Asp Tyr Tyr Ala Gly Pro Gln Val Ile Thr Asp Glu Thr
                260                 265                 270

Lys Ala Ala Met Lys Thr Val Leu Ala Arg Ile Gln Asp Gly Ser Phe
            275                 280                 285

Ala His Glu Phe Met Glu Asp Ser Lys Asn Gly Gln Lys Trp Leu Lys
        290                 295                 300

Glu Gln Arg Met Glu His Gly Asn Ala Gln Ile Glu Glu Val Gly Ala
305                 310                 315                 320

Asn Ile Arg Ser Met Phe Ser Phe Val Arg Arg
                325                 330

<210> SEQ ID NO 7
<211> LENGTH: 996
<212> TYPE: DNA
<213> ORGANISM: Eggerthella lenta

<400> SEQUENCE: 7
atggctgtta cgatctatca tgagaacgac gcgaaccccc agctcatcca ggacaagaaa        60
gtggccatca tcgggtacgg cagccagggc cacgcccatg cgctcaacct gaaagactcg       120
ggggtcgacg tgcgcgtggg cctgcgcgag gactcgaagt cgcgggtcaa ggccgaggag       180
gcgggcctca aggtgatgag cgtcgccgac gccgccgagg aagccgactt catcatgatc       240
ctcacgcccg acgagacgca ggccgcaacc tacgaggccg agatcgcccc gcatctcaag       300
cccggcgaca ccctcgcgtt cgcgcacggc ttcaacatcc acttcggcta catcacgccg       360
cccgaggacg tggacgtcgt catgatcgcg ccgaagggcc cgggccacat ggtgcgccgc       420
gtattcaccg agggcgcggg cgtgccgtgt ctcatctgcg tccagcagga cgcgtcgggc       480
cgggctaagg acgtggcgct gtcctacgcg tggggcatcg gcggcgcgcg cgccggcgtc       540
atcgagacca cgttcaagaa cgagacggaa accgacctgt tcggcgagca ggccgtgctg       600
tgcggcggcg tgacggccct catcaacgcc gggttcgaga cgctcgtcga ggcgggctac       660
ccgcccgaga tggcctactt cgagtgcttc cacgagatga gctcatcgt ggacctcatg       720 tacgaaggcg gcatgtcgaa catgcgctac tccatctcga acacggccga gtacggcgac       780
tactacgccg gcccccaggt gatcaccgac gacgcgaagg ccgcgatgaa gaccatcctc       840
gagcgcatcc aggacggcag cttcgcccac gagttcatgg aggactccaa gaacggccag       900
gcgtggctga aggagcagcg catggagcac ggcaacgccc agatcgagga agtgggcgcc       960
agcatccgct cgatgttcag cttcgtgagg aggtag                                 996

<210> SEQ ID NO 8
<211> LENGTH: 331
<212> TYPE: PRT
<213> ORGANISM: Eggerthella lenta

<400> SEQUENCE: 8

```
Met Ala Val Thr Ile Tyr His Glu Asn Asp Ala Asn Pro Gln Leu Ile
1               5                   10                  15

Gln Asp Lys Lys Val Ala Ile Ile Gly Tyr Gly Ser Gln Gly His Ala
            20                  25                  30

His Ala Leu Asn Leu Lys Asp Ser Gly Val Asp Val Arg Val Gly Leu
        35                  40                  45

Arg Glu Asp Ser Lys Ser Arg Val Lys Ala Glu Glu Ala Gly Leu Lys
    50                  55                  60

Val Met Ser Val Ala Asp Ala Ala Glu Glu Ala Asp Phe Ile Met Ile
65                  70                  75                  80

Leu Thr Pro Asp Glu Thr Gln Ala Ala Thr Tyr Glu Ala Glu Ile Ala
                85                  90                  95

Pro His Leu Lys Pro Gly Asp Thr Leu Ala Phe Ala His Gly Phe Asn
            100                 105                 110

Ile His Phe Gly Tyr Ile Thr Pro Pro Glu Asp Val Asp Val Val Met
        115                 120                 125

Ile Ala Pro Lys Gly Pro Gly His Met Val Arg Arg Val Phe Thr Glu
    130                 135                 140

Gly Ala Gly Val Pro Cys Leu Ile Cys Val Gln Gln Asp Ala Ser Gly
145                 150                 155                 160

Arg Ala Lys Asp Val Ala Leu Ser Tyr Ala Trp Gly Ile Gly Gly Ala
                165                 170                 175

Arg Ala Gly Val Ile Glu Thr Thr Phe Lys Asn Glu Thr Glu Thr Asp
            180                 185                 190

Leu Phe Gly Glu Gln Ala Val Leu Cys Gly Gly Val Thr Ala Leu Ile
            195                 200                 205

Asn Ala Gly Phe Glu Thr Leu Val Glu Ala Gly Tyr Pro Pro Glu Met
    210                 215                 220

Ala Tyr Phe Glu Cys Phe His Glu Met Lys Leu Ile Val Asp Leu Met
225                 230                 235                 240

Tyr Glu Gly Gly Met Ser Asn Met Arg Tyr Ser Ile Ser Asn Thr Ala
                245                 250                 255

Glu Tyr Gly Asp Tyr Tyr Ala Gly Pro Gln Val Ile Thr Asp Asp Ala
            260                 265                 270

Lys Ala Ala Met Lys Thr Ile Leu Glu Arg Ile Gln Asp Gly Ser Phe
        275                 280                 285

Ala His Glu Phe Met Glu Asp Ser Lys Asn Gly Gln Ala Trp Leu Lys
    290                 295                 300

Glu Gln Arg Met Glu His Gly Asn Ala Gln Ile Glu Glu Val Gly Ala
305                 310                 315                 320

Ser Ile Arg Ser Met Phe Ser Phe Val Arg Arg
            325                 330
```

<210> SEQ ID NO 9
<211> LENGTH: 996
<212> TYPE: DNA
<213> ORGANISM: Unknown
<220> FEATURE:
<223> OTHER INFORMATION: Eggerthella sp.

<400> SEQUENCE: 9

```
atggctgtca cgatctatca cgagaaagac gcgaacccccc agctcatcca ggacaagaag     60
gtggccatca tcggctacgg cagccagggc cacgcccatg cgctcaacct gctggactcg    120
ggcgtggacg tgcgcgtggg cctgcgcgag gactcgcgct cgcgggccaa ggccgaggag    180
```

-continued

```
gcgggcctca aggtgatgag cgtcgccgac gctgccgagg aagccgactt catcatgatc      240
ctcacgcccg acgagaccca ggccgccacg tacgaagcgg acatcgcccc gcatctcaag      300
gccggcgaca cgctggcgtt cgcgcacggc ttcaacatcc acttcggcta catcgagtcg      360 cccgcgagg tcgacgtggt catgatcgcg ccgaagggcc cgggccacat ggtgcgccgc       420
gtgttcaccg aaggcgcggg cgtgccgtgc ctcatctgcg tgaaccagga cgcgtcgggc      480
caggccaagg atgtggcgct gtcgtacgcg tggggcatcg gcggcgcgcg cgccggcgtc      540
atcgaaacca cgttcaagaa cgagaccgaa accgacctgt tcggcgagca ggccgtgctg      600
tgcggcggcg tgacggcgct catcaacgcc ggcttcgaga cgctggtgga ggcgggctat      660
ccgcccgaga tggcctactt cgagtgcttc cacgagatga agctcatcgt ggacctcatg      720
tacgagggcg gcatgtcgaa catgcgctac tccatctcga acacggccga gtacggcgac      780
tactacgccg gcccgcaggt gatcaccgac gagacgaaag ccgcgatgaa gaccgtcctc      840
gcgcgcatcc aggacggcag cttcgcccac gagttcatgg aggactcgaa gaacggccag      900
aagtggctca agagcagcg catggagcac ggcaacgccc agatcgagga gtgggcgcc       960 aacatccgct cgatgttcag cttcgtgagg aggtag                                996
```

<210> SEQ ID NO 10
<211> LENGTH: 331
<212> TYPE: PRT
<213> ORGANISM: Unknown
<220> FEATURE:
<223> OTHER INFORMATION: Eggerthella sp.

<400> SEQUENCE: 10

```
Met Ala Val Thr Ile Tyr His Glu Lys Asp Ala Asn Pro Gln Leu Ile
1               5                   10                  15

Gln Asp Lys Lys Val Ala Ile Ile Gly Tyr Gly Ser Gln Gly His Ala
                20                  25                  30

His Ala Leu Asn Leu Leu Asp Ser Gly Val Asp Val Arg Val Gly Leu
            35                  40                  45

Arg Glu Asp Ser Arg Ser Arg Ala Lys Ala Glu Glu Ala Gly Leu Lys
        50                  55                  60

Val Met Ser Val Ala Asp Ala Ala Glu Glu Ala Asp Phe Ile Met Ile
65                  70                  75                  80

Leu Thr Pro Asp Glu Thr Gln Ala Ala Thr Tyr Glu Ala Asp Ile Ala
                85                  90                  95

Pro His Leu Lys Ala Gly Asp Thr Leu Ala Phe Ala His Gly Phe Asn
            100                 105                 110

Ile His Phe Gly Tyr Ile Glu Ser Pro Ala Glu Val Asp Val Val Met
        115                 120                 125

Ile Ala Pro Lys Gly Pro Gly His Met Val Arg Arg Val Phe Thr Glu
        130                 135                 140

Gly Ala Gly Val Pro Cys Leu Ile Cys Val Asn Gln Asp Ala Ser Gly
145                 150                 155                 160

Gln Ala Lys Asp Val Ala Leu Ser Tyr Ala Trp Gly Ile Gly Gly Ala
                165                 170                 175

Arg Ala Gly Val Ile Glu Thr Thr Phe Lys Asn Glu Thr Glu Thr Asp
                180                 185                 190

Leu Phe Gly Glu Gln Ala Val Leu Cys Gly Gly Val Thr Ala Leu Ile
        195                 200                 205

Asn Ala Gly Phe Glu Thr Leu Val Glu Ala Gly Tyr Pro Pro Glu Met
```

-continued

```
       210             215             220

Ala Tyr Phe Glu Cys Phe His Glu Met Lys Leu Ile Val Asp Leu Met
225                 230             235                 240

Tyr Glu Gly Gly Met Ser Asn Met Arg Tyr Ser Ile Ser Asn Thr Ala
                245             250             255

Glu Tyr Gly Asp Tyr Tyr Ala Gly Pro Gln Val Ile Thr Asp Glu Thr
            260             265             270

Lys Ala Ala Met Lys Thr Val Leu Ala Arg Ile Gln Asp Gly Ser Phe
        275             280             285

Ala His Glu Phe Met Glu Asp Ser Lys Asn Gly Gln Lys Trp Leu Lys
    290             295             300

Glu Gln Arg Met Glu His Gly Asn Ala Gln Ile Glu Glu Val Gly Ala
305             310             315                 320

Asn Ile Arg Ser Met Phe Ser Phe Val Arg Arg
            325             330
```

```
<210> SEQ ID NO 11
<211> LENGTH: 1002
<212> TYPE: DNA
<213> ORGANISM: Slackia exigua

<400> SEQUENCE: 11
atggctgtca ccatcttgta cgaacaggac gtcgatccca aagtcataca gggcctcaag      60
gtcggcatca tcggctacgg ctcccagggc catgcccatg cgctgaacct catggattcc     120
ggcgtcgacg tgcgcgtcgg cctgcgcgaa ggatcctctt cctggaagac cgccgaagag     180
gccggcctga aggtcaccga catggacacc gcggccgaag aagccgacgt catcatggtc     240
ctcgtccccg acgagatcca gccgaaggtc taccaggagc acatcgccgc gcacctgaag     300
gcaggcaaca cgctcgcctt cgcccatggc ttcaacatcc actacggcta catcgtgccg     360
cccgaggacg tcaacgtcat catgtgcgct cccaagggcc cggggcacat cgtccgccgt     420
cagttcaccg aaggttccgg cgtgcccgac ctggcctgcg tccagcagga tgccaccggc     480
aacgcctggg atatcgtcct gtcctactgc tggggcgtcg cgggggcccg ttccggcatc     540
atcaaggcga ccttcgccga ggagaccgag gaagacctct tcggcgagca ggccgtgctc     600
tgcggaggcc tggtggagct ggtcaaggcc ggcttcgaga ccctgaccga ggcagggtat     660
ccgcccgagc tggcatactt cgagtgctat cacgagatga gatgatcgt cgacctcatg     720 tacgagagcg gcatccactt catgaactac tcgatctcca acaccgccga atacggcgag     780
tactacgccg gcccgaaggt catcaacgag cagtcccgcg aggccatgaa ggagatcctg     840
aagcgcattc aggacggctc cttcgcccag gaattcgtcg acgactgcaa caacggccat     900
aagcgcctgc tcgagcagcg cgaagcgatc aatacgcacc ccatcgagac caccggcgcc     960
cagatccgca gcatgttctc ctggatcaag aaggaagact ag                        1002
```

```
<210> SEQ ID NO 12
<211> LENGTH: 333
<212> TYPE: PRT
<213> ORGANISM: Slackia exigua

<400> SEQUENCE: 12

Met Ala Val Thr Ile Leu Tyr Glu Gln Asp Val Asp Pro Lys Val Ile
1               5                   10                  15

Gln Gly Leu Lys Val Gly Ile Ile Gly Tyr Gly Ser Gln Gly His Ala
            20                  25                  30
```

-continued

```
His Ala Leu Asn Leu Met Asp Ser Gly Val Asp Val Arg Val Gly Leu
        35              40              45

Arg Glu Gly Ser Ser Ser Trp Lys Thr Ala Glu Glu Ala Gly Leu Lys
    50              55              60

Val Thr Asp Met Asp Thr Ala Ala Glu Glu Ala Asp Val Ile Met Val
65              70              75              80

Leu Val Pro Asp Glu Ile Gln Pro Lys Val Tyr Gln Glu His Ile Ala
            85              90              95

Ala His Leu Lys Ala Gly Asn Thr Leu Ala Phe Ala His Gly Phe Asn
        100             105             110

Ile His Tyr Gly Tyr Ile Val Pro Pro Glu Asp Val Asn Val Ile Met
        115             120             125

Cys Ala Pro Lys Gly Pro Gly His Ile Val Arg Arg Gln Phe Thr Glu
    130             135             140

Gly Ser Gly Val Pro Asp Leu Ala Cys Val Gln Gln Asp Ala Thr Gly
145             150             155             160

Asn Ala Trp Asp Ile Val Leu Ser Tyr Cys Trp Gly Val Gly Gly Ala
            165             170             175

Arg Ser Gly Ile Ile Lys Ala Thr Phe Ala Glu Glu Thr Glu Glu Asp
            180             185             190

Leu Phe Gly Glu Gln Ala Val Leu Cys Gly Gly Leu Val Glu Leu Val
            195             200             205

Lys Ala Gly Phe Glu Thr Leu Thr Glu Ala Gly Tyr Pro Pro Glu Leu
    210             215             220

Ala Tyr Phe Glu Cys Tyr His Glu Met Lys Met Ile Val Asp Leu Met
225             230             235             240

Tyr Glu Ser Gly Ile His Phe Met Asn Tyr Ser Ile Ser Asn Thr Ala
            245             250             255

Glu Tyr Gly Glu Tyr Tyr Ala Gly Pro Lys Val Ile Asn Glu Gln Ser
            260             265             270

Arg Glu Ala Met Lys Glu Ile Leu Lys Arg Ile Gln Asp Gly Ser Phe
    275             280             285

Ala Gln Glu Phe Val Asp Asp Cys Asn Asn Gly His Lys Arg Leu Leu
    290             295             300

Glu Gln Arg Glu Ala Ile Asn Thr His Pro Ile Glu Thr Thr Gly Ala
305             310             315             320

Gln Ile Arg Ser Met Phe Ser Trp Ile Lys Lys Glu Asp
            325             330
```

<210> SEQ ID NO 13
<211> LENGTH: 7
<212> TYPE: PRT
<213> ORGANISM: Artificial Sequence
<220> FEATURE:
<223> OTHER INFORMATION: acetolactate synthase consensus sequence
<220> FEATURE:
<221> NAME/KEY: VARIANT
<222> LOCATION: (5)..(5)
<223> OTHER INFORMATION: Xaa may be Ala, Cys or Val
<220> FEATURE:
<221> NAME/KEY: VARIANT
<222> LOCATION: (6)..(6)
<223> OTHER INFORMATION: Xaa may be Thr or Ser

<400> SEQUENCE: 13

```
Ser Gly Pro Gly Xaa Xaa Asn
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: acetolactate synthase consensus sequence
<220> FEATURE:
<221> NAME/KEY: VARIANT
<222> LOCATION: (2)..(2)
<223> OTHER INFORMATION: Xaa may be any naturally occurring amino acid
<220> FEATURE:
<221> NAME/KEY: VARIANT
<222> LOCATION: (3)..(3)
<223> OTHER INFORMATION: Xaa may be Pro or Ala
<220> FEATURE:
<221> NAME/KEY: VARIANT
<222> LOCATION: (5)..(5)
<223> OTHER INFORMATION: Xaa may be any naturally occurring amino acid
<220> FEATURE:
<221> NAME/KEY: VARIANT
<222> LOCATION: (6)..(6)
<223> OTHER INFORMATION: Xaa may be Val, Ala or Thr

<400> SEQUENCE: 14

Gly Xaa Xaa Gly Xaa Xaa
1               5

<210> SEQ ID NO 15
<211> LENGTH: 15
<212> TYPE: PRT
<213> ORGANISM: Artificial Sequence
<220> FEATURE:
<223> OTHER INFORMATION: acetolactate synthase consensus sequence
<220> FEATURE:
<221> NAME/KEY: VARIANT
<222> LOCATION: (2)..(2)
<223> OTHER INFORMATION: Xaa may be any naturally occurring amino acid
<220> FEATURE:
<221> NAME/KEY: VARIANT
<222> LOCATION: (3)..(3)
<223> OTHER INFORMATION: Xaa may be Gln or Gly
<220> FEATURE:
<221> NAME/KEY: VARIANT
<222> LOCATION: (4)..(4)
<223> OTHER INFORMATION: Xaa may be Thr or Ala
<220> FEATURE:
<221> NAME/KEY: VARIANT
<222> LOCATION: (5)..(5)
<223> OTHER INFORMATION: Xaa may be Leu or Met
<220> FEATURE:
<221> NAME/KEY: VARIANT
<222> LOCATION: (7)..(7)
<223> OTHER INFORMATION: Xaa may be Tyr, Phe or Trp
<220> FEATURE:
<221> NAME/KEY: VARIANT
<222> LOCATION: (8)..(8)
<223> OTHER INFORMATION: Xaa may be Ala or Gly
<220> FEATURE:
<221> NAME/KEY: VARIANT
<222> LOCATION: (9)..(9)
<223> OTHER INFORMATION: Xaa may be any naturally occurring amino acid
<220> FEATURE:
<221> NAME/KEY: VARIANT
<222> LOCATION: (10)..(10)
<223> OTHER INFORMATION: Xaa may be Pro or Gly
<220> FEATURE:
<221> NAME/KEY: VARIANT
<222> LOCATION: (11)..(11)
<223> OTHER INFORMATION: Xaa may be Trp or Ala
<220> FEATURE:
<221> NAME/KEY: VARIANT
<222> LOCATION: (13)..(13)
<223> OTHER INFORMATION: Xaa may be any naturally occurring amino acid
<220> FEATURE:
<221> NAME/KEY: VARIANT
<222> LOCATION: (14)..(14)
<223> OTHER INFORMATION: Xaa may be Gly or Thr
```

-continued

```
<220> FEATURE:
<221> NAME/KEY: VARIANT
<222> LOCATION: (15)..(15)
<223> OTHER INFORMATION: Xaa may be Ala or Val

<400> SEQUENCE: 15

Gly Xaa Xaa Xaa Xaa Gly Xaa Xaa Xaa Xaa Xaa Ala Xaa Xaa Xaa
1               5                   10                  15

<210> SEQ ID NO 16
<211> LENGTH: 5
<212> TYPE: PRT
<213> ORGANISM: Artificial Sequence
<220> FEATURE:
<223> OTHER INFORMATION: acetolactate synthase consensus sequence
<220> FEATURE:
<221> NAME/KEY: VARIANT
<222> LOCATION: (3)..(3)
<223> OTHER INFORMATION: Xaa may be Gly or Ala
<220> FEATURE:
<221> NAME/KEY: VARIANT
<222> LOCATION: (4)..(4)
<223> OTHER INFORMATION: Xaa may be Gly, Ser or Cys

<400> SEQUENCE: 16

Gly Asp Xaa Xaa Phe
1               5

<210> SEQ ID NO 17
<211> LENGTH: 9
<212> TYPE: PRT
<213> ORGANISM: Artificial Sequence
<220> FEATURE:
<223> OTHER INFORMATION: dihydroxy acid dehydratase consensus sequence
<220> FEATURE:
<221> NAME/KEY: VARIANT
<222> LOCATION: (3)..(3)
<223> OTHER INFORMATION: Xaa may be any naturally occurring amino acid
<220> FEATURE:
<221> NAME/KEY: VARIANT
<222> LOCATION: (6)..(7)
<223> OTHER INFORMATION: Xaa may be any naturally occurring amino acid

<400> SEQUENCE: 17

Ser Leu Xaa Ser Arg Xaa Xaa Ile Ala
1               5

<210> SEQ ID NO 18
<211> LENGTH: 7
<212> TYPE: PRT
<213> ORGANISM: Artificial Sequence
<220> FEATURE:
<223> OTHER INFORMATION: dihydroxy acid dehydratase consensus sequence
<220> FEATURE:
<221> NAME/KEY: VARIANT
<222> LOCATION: (4)..(5)
<223> OTHER INFORMATION: Xaa may be any naturally occurring amino acid

<400> SEQUENCE: 18

Cys Asp Lys Xaa Xaa Pro Gly
1               5

<210> SEQ ID NO 19
<211> LENGTH: 10
<212> TYPE: PRT
<213> ORGANISM: Artificial Sequence
<220> FEATURE:
<223> OTHER INFORMATION: dihydroxy acid dehydratase consensus sequence
<220> FEATURE:
<221> NAME/KEY: VARIANT
<222> LOCATION: (2)..(2)
```

```
<223> OTHER INFORMATION: Xaa may be any naturally occurring amino acid
<220> FEATURE:
<221> NAME/KEY: VARIANT
<222> LOCATION: (4)..(4)
<223> OTHER INFORMATION: Xaa may be any naturally occurring amino acid
<220> FEATURE:
<221> NAME/KEY: VARIANT
<222> LOCATION: (6)..(7)
<223> OTHER INFORMATION: Xaa may be any naturally occurring amino acid

<400> SEQUENCE: 19

Gly Xaa Cys Xaa Gly Xaa Xaa Thr Ala Asn
1               5                   10

<210> SEQ ID NO 20
<211> LENGTH: 5
<212> TYPE: PRT
<213> ORGANISM: Artificial Sequence
<220> FEATURE:
<223> OTHER INFORMATION: dihydroxy acid dehydratase consensus sequence

<400> SEQUENCE: 20

Gly Gly Ser Thr Asn
1               5

<210> SEQ ID NO 21
<211> LENGTH: 11
<212> TYPE: PRT
<213> ORGANISM: Artificial Sequence
<220> FEATURE:
<223> OTHER INFORMATION: dihydroxy acid dehydratase consensus sequence
<220> FEATURE:
<221> NAME/KEY: VARIANT
<222> LOCATION: (3)..(3)
<223> OTHER INFORMATION: Xaa may be any naturally occurring amino acid
<220> FEATURE:
<221> NAME/KEY: VARIANT
<222> LOCATION: (5)..(5)
<223> OTHER INFORMATION: Xaa may be any naturally occurring amino acid
<220> FEATURE:
<221> NAME/KEY: VARIANT
<222> LOCATION: (10)..(10)
<223> OTHER INFORMATION: Xaa may be any naturally occurring amino acid

<400> SEQUENCE: 21

Gly Pro Xaa Gly Xaa Pro Gly Met Arg Xaa Glu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: dihydroxy acid dehydratase consensus sequence
<220> FEATURE:
<221> NAME/KEY: VARIANT
<222> LOCATION: (3)..(3)
<223> OTHER INFORMATION: Xaa may be any naturally occurring amino acid
<220> FEATURE:
<221> NAME/KEY: VARIANT
<222> LOCATION: (8)..(8)
<223> OTHER INFORMATION: Xaa may be any naturally occurring amino acid

<400> SEQUENCE: 22

Ala Leu Xaa Thr Asp Gly Arg Xaa Ser Gly
1               5                   10

<210> SEQ ID NO 23
<211> LENGTH: 7
<212> TYPE: PRT
<213> ORGANISM: Artificial Sequence
```

-continued

```
<220> FEATURE:
<223> OTHER INFORMATION: dihydroxy acid dehydratase consensus sequence
<220> FEATURE:
<221> NAME/KEY: VARIANT
<222> LOCATION: (3)..(4)
<223> OTHER INFORMATION: Xaa may be any naturally occurring amino acid

<400> SEQUENCE: 23

Gly His Xaa Xaa Pro Glu Ala
1               5

<210> SEQ ID NO 24
<211> LENGTH: 7
<212> TYPE: PRT
<213> ORGANISM: Artificial Sequence
<220> FEATURE:
<223> OTHER INFORMATION: 2-keto-acid decarboxylase consensus sequence
<220> FEATURE:
<221> NAME/KEY: VARIANT
<222> LOCATION: (3)..(3)
<223> OTHER INFORMATION: Xaa may be Val or Ile
<220> FEATURE:
<221> NAME/KEY: VARIANT
<222> LOCATION: (4)..(4)
<223> OTHER INFORMATION: Xaa may be Pro or Ser
<220> FEATURE:
<221> NAME/KEY: VARIANT
<222> LOCATION: (6)..(6)
<223> OTHER INFORMATION: Xaa may be Asp or Glu
<220> FEATURE:
<221> NAME/KEY: VARIANT
<222> LOCATION: (7)..(7)
<223> OTHER INFORMATION: Xaa may be Tyr or Phe

<400> SEQUENCE: 24

Phe Gly Xaa Xaa Gly Xaa Xaa
1               5

<210> SEQ ID NO 25
<211> LENGTH: 9
<212> TYPE: PRT
<213> ORGANISM: Artificial Sequence
<220> FEATURE:
<223> OTHER INFORMATION: 2-keto-acid decarboxylase consensus sequence
<220> FEATURE:
<221> NAME/KEY: VARIANT
<222> LOCATION: (1)..(1)
<223> OTHER INFORMATION: Xaa may be Thr or Val
<220> FEATURE:
<221> NAME/KEY: VARIANT
<222> LOCATION: (3)..(3)
<223> OTHER INFORMATION: Xaa may be Phe or Tyr
<220> FEATURE:
<221> NAME/KEY: VARIANT
<222> LOCATION: (5)..(5)
<223> OTHER INFORMATION: Xaa may be Val or Ala
<220> FEATURE:
<221> NAME/KEY: VARIANT
<222> LOCATION: (7)..(7)
<223> OTHER INFORMATION: Xaa may be Glu or Ala
<220> FEATURE:
<221> NAME/KEY: VARIANT
<222> LOCATION: (8)..(8)
<223> OTHER INFORMATION: Xaa may be Leu or Phe
<220> FEATURE:
<221> NAME/KEY: VARIANT
<222> LOCATION: (9)..(9)
<223> OTHER INFORMATION: Xaa may be Ser or Asn

<400> SEQUENCE: 25

Xaa Thr Xaa Gly Xaa Gly Xaa Xaa Xaa
1               5
```

-continued

```
<210> SEQ ID NO 26
<211> LENGTH: 9
<212> TYPE: PRT
<213> ORGANISM: Artificial Sequence
<220> FEATURE:
<223> OTHER INFORMATION: 2-keto-acid decarboxylase consensus sequence
<220> FEATURE:
<221> NAME/KEY: VARIANT
<222> LOCATION: (2)..(2)
<223> OTHER INFORMATION: Xaa may be Gly or Ala
<220> FEATURE:
<221> NAME/KEY: VARIANT
<222> LOCATION: (3)..(3)
<223> OTHER INFORMATION: Xaa may be Leu, Ile or Val
<220> FEATURE:
<221> NAME/KEY: VARIANT
<222> LOCATION: (6)..(6)
<223> OTHER INFORMATION: Xaa may be Ser or Ala
<220> FEATURE:
<221> NAME/KEY: VARIANT
<222> LOCATION: (7)..(7)
<223> OTHER INFORMATION: Xaa may be Tyr or Phe

<400> SEQUENCE: 26

Asn Xaa Xaa Ala Gly Xaa Xaa Ala Glu
1               5

<210> SEQ ID NO 27
<211> LENGTH: 6
<212> TYPE: PRT
<213> ORGANISM: Artificial Sequence
<220> FEATURE:
<223> OTHER INFORMATION: 2-keto-acid decarboxylase consensus sequence
<220> FEATURE:
<221> NAME/KEY: VARIANT
<222> LOCATION: (1)..(1)
<223> OTHER INFORMATION: Xaa may be Val or Ile
<220> FEATURE:
<221> NAME/KEY: VARIANT
<222> LOCATION: (2)..(2)
<223> OTHER INFORMATION: Xaa may be Leu, Ile or Val
<220> FEATURE:
<221> NAME/KEY: VARIANT
<222> LOCATION: (3)..(3)
<223> OTHER INFORMATION: Xaa may be any naturally occurring amino acid
<220> FEATURE:
<221> NAME/KEY: VARIANT
<222> LOCATION: (5)..(5)
<223> OTHER INFORMATION: Xaa may be Val, Thr or Ser

<400> SEQUENCE: 27

Xaa Xaa Xaa Ile Xaa Gly
1               5

<210> SEQ ID NO 28
<211> LENGTH: 8
<212> TYPE: PRT
<213> ORGANISM: Artificial Sequence
<220> FEATURE:
<223> OTHER INFORMATION: 2-keto-acid decarboxylase consensus sequence
<220> FEATURE:
<221> NAME/KEY: VARIANT
<222> LOCATION: (4)..(4)
<223> OTHER INFORMATION: Xaa may be Ser or Ala
<220> FEATURE:
<221> NAME/KEY: VARIANT
<222> LOCATION: (5)..(5)
<223> OTHER INFORMATION: Xaa may be Leu or Phe or Ala
<220> FEATURE:
<221> NAME/KEY: VARIANT
<222> LOCATION: (7)..(7)
<223> OTHER INFORMATION: Xaa may be Leu or Met

<400> SEQUENCE: 28
```

```
Gly Asp Gly Xaa Xaa Gln Xaa Thr
1               5
```

<210> SEQ ID NO 29
<211> LENGTH: 6
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (2)..(2)
<223> OTHER INFORMATION: Xaa may be His or Gly
<220> FEATURE:
<221> NAME/KEY: VARIANT
<222> LOCATION: (3)..(3)
<223> OTHER INFORMATION: Xaa may be Thr or Ser
<220> FEATURE:
<221> NAME/KEY: VARIANT
<222> LOCATION: (5)..(5)
<223> OTHER INFORMATION: Xaa may be Leu or Ile

<400> SEQUENCE: 29

```
Cys Xaa Xaa Asp Xaa His
1               5
```

<210> SEQ ID NO 30
<211> LENGTH: 8
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (4)..(5)
<223> OTHER INFORMATION: Xaa may be any naturally occurring amino acid
<220> FEATURE:
<221> NAME/KEY: VARIANT
<222> LOCATION: (7)..(7)
<223> OTHER INFORMATION: Xaa may be any naturally occurring amino acid

<400> SEQUENCE: 30

```
Gly His Glu Xaa Xaa Gly Xaa Val
1               5
```

<210> SEQ ID NO 31
<211> LENGTH: 7
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (1)..(1)
<223> OTHER INFORMATION: Xaa may be Leu or Val
<220> FEATURE:
<221> NAME/KEY: VARIANT
<222> LOCATION: (2)..(2)
<223> OTHER INFORMATION: Xaa may be Gln, Lys or Glu
<220> FEATURE:
<221> NAME/KEY: VARIANT
<222> LOCATION: (3)..(3)
<223> OTHER INFORMATION: Xaa may be Val, Ile or Lys
<220> FEATURE:
<221> NAME/KEY: VARIANT
<222> LOCATION: (5)..(5)
<223> OTHER INFORMATION: Xaa may be Asp or Gln
<220> FEATURE:
<221> NAME/KEY: VARIANT
<222> LOCATION: (6)..(6)
<223> OTHER INFORMATION: Xaa may be Arg or His
<220> FEATURE:
<221> NAME/KEY: VARIANT
<222> LOCATION: (7)..(7)

<223> OTHER INFORMATION: Xaa may be Val or Ala

<400> SEQUENCE: 31

Xaa Xaa Xaa Gly Xaa Xaa Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (2)..(3)
<223> OTHER INFORMATION: Xaa may be any naturally occurring amino acid
<220> FEATURE:
<221> NAME/KEY: VARIANT
<222> LOCATION: (5)..(6)
<223> OTHER INFORMATION: Xaa may be any naturally occurring amino acid

<400> SEQUENCE: 32

Cys Xaa Xaa Cys Xaa Xaa Cys
1               5

<210> SEQ ID NO 33
<211> LENGTH: 6
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (1)..(1)
<223> OTHER INFORMATION: Xaa may be Cys or Ala
<220> FEATURE:
<221> NAME/KEY: VARIANT
<222> LOCATION: (2)..(2)
<223> OTHER INFORMATION: Xaa may be Ala, Gly or Asp
<220> FEATURE:
<221> NAME/KEY: VARIANT
<222> LOCATION: (3)..(3)
<223> OTHER INFORMATION: Xaa may be Gly or Ala
<220> FEATURE:
<221> NAME/KEY: VARIANT
<222> LOCATION: (4)..(4)
<223> OTHER INFORMATION: Xaa may be any naturally occurring amino acid
<220> FEATURE:
<221> NAME/KEY: VARIANT
<222> LOCATION: (6)..(6)
<223> OTHER INFORMATION: Xaa may be Thr or Val

<400> SEQUENCE: 33

Xaa Xaa Xaa Xaa Thr Xaa
1               5

<210> SEQ ID NO 34
<211> LENGTH: 6
<212> TYPE: PRT
<213> ORGANISM: Artificial Sequence
<220> FEATURE:
<223> OTHER INFORMATION: alcohol dehydrogenase consensus sequence
<220> FEATURE:
<221> NAME/KEY: VARIANT
<222> LOCATION: (2)..(2)
<223> OTHER INFORMATION: Xaa may be Leu, Ala or Cys
<220> FEATURE:
<221> NAME/KEY: VARIANT
<222> LOCATION: (4)..(4)
<223> OTHER INFORMATION: Xaa may be Gly or Pro
<220> FEATURE:
<221> NAME/KEY: VARIANT
<222> LOCATION: (5)..(5)

<223> OTHER INFORMATION: Xaa may be Leu, Ile or Val

<400> SEQUENCE: 34

Gly Xaa Gly Xaa Xaa Gly
1               5

<210> SEQ ID NO 35
<211> LENGTH: 20
<212> TYPE: DNA
<213> ORGANISM: Artificial Sequence
<220> FEATURE:
<223> OTHER INFORMATION: Primer T7_for

<400> SEQUENCE: 35
taatacgact cactataggg                                                        20

<210> SEQ ID NO 36
<211> LENGTH: 19
<212> TYPE: DNA
<213> ORGANISM: Artificial Sequence
<220> FEATURE:
<223> OTHER INFORMATION: Primer T7_rev

<400> SEQUENCE: 36
gctagttatt gctcagcgg                                                         19

<210> SEQ ID NO 37
<211> LENGTH: 39
<212> TYPE: DNA
<213> ORGANISM: Artificial Sequence
<220> FEATURE:
<223> OTHER INFORMATION: Primer Se_I33NNK_for
<220> FEATURE:
<221> NAME/KEY: misc_feature
<222> LOCATION: (19)..(20)
<223> OTHER INFORMATION: n is a, c, g, or t

<400> SEQUENCE: 37
ggtcttaaag ttggtatcnn kggttacggt tcccaaggt                                   39

<210> SEQ ID NO 38
<211> LENGTH: 39
<212> TYPE: DNA
<213> ORGANISM: Artificial Sequence
<220> FEATURE:
<223> OTHER INFORMATION: Primer Se_I33NNK_rev
<220> FEATURE:
<221> NAME/KEY: misc_feature
<222> LOCATION: (20)..(21)
<223> OTHER INFORMATION: n is a, c, g, or t

<400> SEQUENCE: 38
accttgggaa ccgtaaccmn ngataccaac tttaagacc                                   39

<210> SEQ ID NO 39
<211> LENGTH: 33
<212> TYPE: DNA
<213> ORGANISM: Artificial Sequence
<220> FEATURE:
<223> OTHER INFORMATION: Primer Se_G34NNK_for
<220> FEATURE:
<221> NAME/KEY: misc_feature
<222> LOCATION: (16)..(17)
<223> OTHER INFORMATION: n is a, c, g, or t

<400> SEQUENCE: 39
aaagttggta tcatcnnkta cggttcccaa ggt                                         33

-continued

```
<210> SEQ ID NO 40
<211> LENGTH: 33
<212> TYPE: DNA
<213> ORGANISM: Artificial Sequence
<220> FEATURE:
<223> OTHER INFORMATION: Primer Se_G34NNK_rev
<220> FEATURE:
<221> NAME/KEY: misc_feature
<222> LOCATION: (17)..(18)
<223> OTHER INFORMATION: n is a, c, g, or t

<400> SEQUENCE: 40
accttgggaa ccgtamnnga tgataccaac ttt                          33

<210> SEQ ID NO 41
<211> LENGTH: 33
<212> TYPE: DNA
<213> ORGANISM: Artificial Sequence
<220> FEATURE:
<223> OTHER INFORMATION: Primer Se_Y35NNK_for
<220> FEATURE:
<221> NAME/KEY: misc_feature
<222> LOCATION: (16)..(17)
<223> OTHER INFORMATION: n is a, c, g, or t

<400> SEQUENCE: 41
gttggtatca tcggtnnkgg ttcccaaggt cac                          33

<210> SEQ ID NO 42
<211> LENGTH: 33
<212> TYPE: DNA
<213> ORGANISM: Artificial Sequence
<220> FEATURE:
<223> OTHER INFORMATION: Primer Se_Y35NNK_rev
<220> FEATURE:
<221> NAME/KEY: misc_feature
<222> LOCATION: (17)..(18)
<223> OTHER INFORMATION: n is a, c, g, or t

<400> SEQUENCE: 42
gtgaccttgg gaaccmnnac cgatgatacc aac                          33

<210> SEQ ID NO 43
<211> LENGTH: 33
<212> TYPE: DNA
<213> ORGANISM: Artificial Sequence
<220> FEATURE:
<223> OTHER INFORMATION: Primer Se_G36NNK_for
<220> FEATURE:
<221> NAME/KEY: misc_feature
<222> LOCATION: (16)..(17)
<223> OTHER INFORMATION: n is a, c, g, or t

<400> SEQUENCE: 43
ggtatcatcg gttacnnktc ccaaggtcac gct                          33

<210> SEQ ID NO 44
<211> LENGTH: 33
<212> TYPE: DNA
<213> ORGANISM: Artificial Sequence
<220> FEATURE:
<223> OTHER INFORMATION: Primer Se_G36NNK_rev
<220> FEATURE:
<221> NAME/KEY: misc_feature
<222> LOCATION: (17)..(18)
<223> OTHER INFORMATION: n is a, c, g, or t

<400> SEQUENCE: 44
agcgtgacct tgggamnngt aaccgatgat acc                          33
```

<210> SEQ ID NO 45
<211> LENGTH: 33
<212> TYPE: DNA
<213> ORGANISM: Artificial Sequence
<220> FEATURE:
<223> OTHER INFORMATION: Primer Se_L57NNK_for
<220> FEATURE:
<221> NAME/KEY: misc_feature
<222> LOCATION: (16)..(17)
<223> OTHER INFORMATION: n is a, c, g, or t

<400> SEQUENCE: 45
gatgttagag ttggcnnkag agaaggctca tct                              33

<210> SEQ ID NO 46
<211> LENGTH: 33
<212> TYPE: DNA
<213> ORGANISM: Artificial Sequence
<220> FEATURE:
<223> OTHER INFORMATION: Primer Se_L57NNK_rev
<220> FEATURE:
<221> NAME/KEY: misc_feature
<222> LOCATION: (17)..(18)
<223> OTHER INFORMATION: n is a, c, g, or t

<400> SEQUENCE: 46
agatgagcct tctctmnngc caactctaac atc                              33

<210> SEQ ID NO 47
<211> LENGTH: 33
<212> TYPE: DNA
<213> ORGANISM: Artificial Sequence
<220> FEATURE:
<223> OTHER INFORMATION: Primer Se_R58NNK_for
<220> FEATURE:
<221> NAME/KEY: misc_feature
<222> LOCATION: (16)..(17)
<223> OTHER INFORMATION: n is a, c, g, or t

<400> SEQUENCE: 47
gttagagttg gcttannkga aggctcatct agt                              33

<210> SEQ ID NO 48
<211> LENGTH: 33
<212> TYPE: DNA
<213> ORGANISM: Artificial Sequence
<220> FEATURE:
<223> OTHER INFORMATION: Primer Se_R58NNK_rev
<220> FEATURE:
<221> NAME/KEY: misc_feature
<222> LOCATION: (17)..(18)
<223> OTHER INFORMATION: n is a, c, g, or t

<400> SEQUENCE: 48
actagatgag ccttcmnnta agccaactct aac                              33

<210> SEQ ID NO 49
<211> LENGTH: 33
<212> TYPE: DNA
<213> ORGANISM: Artificial Sequence
<220> FEATURE:
<223> OTHER INFORMATION: Primer Se_G60NNK_for
<220> FEATURE:
<221> NAME/KEY: misc_feature
<222> LOCATION: (16)..(17)
<223> OTHER INFORMATION: n is a, c, g, or t

<400> SEQUENCE: 49

-continued

```
gttggcttaa gagaannktc atctagttgg aaa                                    33

<210> SEQ ID NO 50
<211> LENGTH: 33
<212> TYPE: DNA
<213> ORGANISM: Artificial Sequence
<220> FEATURE:
<223> OTHER INFORMATION: Primer Se_G60NNK_rev
<220> FEATURE:
<221> NAME/KEY: misc_feature
<222> LOCATION: (17)..(18)
<223> OTHER INFORMATION: n is a, c, g, or t

<400> SEQUENCE: 50
tttccaacta gatgamnntt ctcttaagcc aac                                    33

<210> SEQ ID NO 51
<211> LENGTH: 33
<212> TYPE: DNA
<213> ORGANISM: Artificial Sequence
<220> FEATURE:
<223> OTHER INFORMATION: Primer Se_S61NNK_for
<220> FEATURE:
<221> NAME/KEY: misc_feature
<222> LOCATION: (16)..(17)
<223> OTHER INFORMATION: n is a, c, g, or t

<400> SEQUENCE: 51
ggcttaagag aaggcnnktc tagttggaaa acg                                    33

<210> SEQ ID NO 52
<211> LENGTH: 33
<212> TYPE: DNA
<213> ORGANISM: Artificial Sequence
<220> FEATURE:
<223> OTHER INFORMATION: Primer Se_S61NNK_rev
<220> FEATURE:
<221> NAME/KEY: misc_feature
<222> LOCATION: (17)..(18)
<223> OTHER INFORMATION: n is a, c, g, or t

<400> SEQUENCE: 52
cgttttccaa ctagamnngc cttctcttaa gcc                                    33

<210> SEQ ID NO 53
<211> LENGTH: 33
<212> TYPE: DNA
<213> ORGANISM: Artificial Sequence
<220> FEATURE:
<223> OTHER INFORMATION: Primer Se_S62NNK_for
<220> FEATURE:
<221> NAME/KEY: misc_feature
<222> LOCATION: (16)..(17)
<223> OTHER INFORMATION: n is a, c, g, or t

<400> SEQUENCE: 53
ttaagagaag gctcannkag ttggaaaacg gct                                    33

<210> SEQ ID NO 54
<211> LENGTH: 33
<212> TYPE: DNA
<213> ORGANISM: Artificial Sequence
<220> FEATURE:
<223> OTHER INFORMATION: Primer Se_S62NNK_rev
<220> FEATURE:
<221> NAME/KEY: misc_feature
<222> LOCATION: (17)..(18)
<223> OTHER INFORMATION: n is a, c, g, or t

<400> SEQUENCE: 54
```

-continued agccgtttc caactmnntg agccttctct taa                                      33

<210> SEQ ID NO 55
<211> LENGTH: 33
<212> TYPE: DNA
<213> ORGANISM: Artificial Sequence
<220> FEATURE:
<223> OTHER INFORMATION: Primer Se_S63NNK_for
<220> FEATURE:
<221> NAME/KEY: misc_feature
<222> LOCATION: (16)..(17)
<223> OTHER INFORMATION: n is a, c, g, or t

<400> SEQUENCE: 55
agagaaggct catctnnktg gaaaacggct gag                                     33

<210> SEQ ID NO 56
<211> LENGTH: 33
<212> TYPE: DNA
<213> ORGANISM: Artificial Sequence
<220> FEATURE:
<223> OTHER INFORMATION: Primer Se_S63NNK_rev
<220> FEATURE:
<221> NAME/KEY: misc_feature
<222> LOCATION: (17)..(18)
<223> OTHER INFORMATION: n is a, c, g, or t

<400> SEQUENCE: 56
ctcagccgtt ttccamnnag atgagccttc tct                                     33

<210> SEQ ID NO 57
<211> LENGTH: 33
<212> TYPE: DNA
<213> ORGANISM: Artificial Sequence
<220> FEATURE:
<223> OTHER INFORMATION: Primer Se_L90NNK_for
<220> FEATURE:
<221> NAME/KEY: misc_feature
<222> LOCATION: (16)..(17)
<223> OTHER INFORMATION: n is a, c, g, or t

<400> SEQUENCE: 57
gatgtcatca tggttnnkgt gcctgatgaa att                                     33

<210> SEQ ID NO 58
<211> LENGTH: 33
<212> TYPE: DNA
<213> ORGANISM: Artificial Sequence
<220> FEATURE:
<223> OTHER INFORMATION: Primer Se_L90NNK_rev
<220> FEATURE:
<221> NAME/KEY: misc_feature
<222> LOCATION: (17)..(18)
<223> OTHER INFORMATION: n is a, c, g, or t

<400> SEQUENCE: 58
aatttcatca ggcacmnnaa ccatgatgac atc                                     33

<210> SEQ ID NO 59
<211> LENGTH: 33
<212> TYPE: DNA
<213> ORGANISM: Artificial Sequence
<220> FEATURE:
<223> OTHER INFORMATION: Primer Se_I95NNK_for
<220> FEATURE:
<221> NAME/KEY: misc_feature
<222> LOCATION: (16)..(17)
<223> OTHER INFORMATION: n is a, c, g, or t

```
<400> SEQUENCE: 59
ttggtgcctg atgaannkca acctaaggta tat                                33

<210> SEQ ID NO 60
<211> LENGTH: 33
<212> TYPE: DNA
<213> ORGANISM: Artificial Sequence
<220> FEATURE:
<223> OTHER INFORMATION: Primer Se_I95NNK_rev
<220> FEATURE:
<221> NAME/KEY: misc_feature
<222> LOCATION: (17)..(18)
<223> OTHER INFORMATION: n is a, c, g, or t

<400> SEQUENCE: 60
atatacctta ggttgmnntt catcaggcac caa                                33

<210> SEQ ID NO 61
<211> LENGTH: 33
<212> TYPE: DNA
<213> ORGANISM: Artificial Sequence
<220> FEATURE:
<223> OTHER INFORMATION: Primer Se_V99NNK_for
<220> FEATURE:
<221> NAME/KEY: misc_feature
<222> LOCATION: (16)..(17)
<223> OTHER INFORMATION: n is a, c, g, or t

<400> SEQUENCE: 61
gaaattcaac ctaagnnkta tcaggaacat atc                                33

<210> SEQ ID NO 62
<211> LENGTH: 33
<212> TYPE: DNA
<213> ORGANISM: Artificial Sequence
<220> FEATURE:
<223> OTHER INFORMATION: Primer Se_V99NNK_rev
<220> FEATURE:
<221> NAME/KEY: misc_feature
<222> LOCATION: (17)..(18)
<223> OTHER INFORMATION: n is a, c, g, or t

<400> SEQUENCE: 62
gatatgttcc tgatamnnct taggttgaat ttc                                33

<210> SEQ ID NO 63
<211> LENGTH: 27
<212> TYPE: DNA
<213> ORGANISM: Artificial Sequence
<220> FEATURE:
<223> OTHER INFORMATION: Primer Se_recomb1_Y35YAC_for

<400> SEQUENCE: 63
ggtatcatcg gtyacggttc ccaaggt                                       27

<210> SEQ ID NO 64
<211> LENGTH: 27
<212> TYPE: DNA
<213> ORGANISM: Artificial Sequence
<220> FEATURE:
<223> OTHER INFORMATION: Primer Se_recomb1_Y35YAC_rev

<400> SEQUENCE: 64
accttgggaa ccgtraccga tgatacc                                       27

<210> SEQ ID NO 65
<211> LENGTH: 36
```

-continued

```
<212> TYPE: DNA
<213> ORGANISM: Artificial Sequence
<220> FEATURE:
<223> OTHER INFORMATION: Primer Se_recomb2a_for

<400> SEQUENCE: 65
ggcttaagag aagkatsctc tagttggaaa acggct                                    36

<210> SEQ ID NO 66
<211> LENGTH: 36
<212> TYPE: DNA
<213> ORGANISM: Artificial Sequence
<220> FEATURE:
<223> OTHER INFORMATION: Primer Se_recomb2b_for

<400> SEQUENCE: 66
ggcttaagag aagkatsctc tgattggaaa acggct                                    36

<210> SEQ ID NO 67
<211> LENGTH: 36
<212> TYPE: DNA
<213> ORGANISM: Artificial Sequence
<220> FEATURE:
<223> OTHER INFORMATION: Primer Se_recomb2c_for

<400> SEQUENCE: 67
ggcttaagag aagkatsctc tcagtggaaa acggct                                    36

<210> SEQ ID NO 68
<211> LENGTH: 36
<212> TYPE: DNA
<213> ORGANISM: Artificial Sequence
<220> FEATURE:
<223> OTHER INFORMATION: Primer Se_recomb2a_rev

<400> SEQUENCE: 68
agccgttttc caactagags atmcttctct taagcc                                    36

<210> SEQ ID NO 69
<211> LENGTH: 36
<212> TYPE: DNA
<213> ORGANISM: Artificial Sequence
<220> FEATURE:
<223> OTHER INFORMATION: Primer Se_recomb2b_rev

<400> SEQUENCE: 69
agccgttttc caatcagags atmcttctct taagcc                                    36

<210> SEQ ID NO 70
<211> LENGTH: 36
<212> TYPE: DNA
<213> ORGANISM: Artificial Sequence
<220> FEATURE:
<223> OTHER INFORMATION: Primer Se_recomb2c_rev

<400> SEQUENCE: 70
agccgttttc cactgagags atmcttctct taagcc                                    36

<210> SEQ ID NO 71
<211> LENGTH: 33
<212> TYPE: DNA
<213> ORGANISM: Artificial Sequence
<220> FEATURE:
<223> OTHER INFORMATION: Primer Se_recomb3a_for

<400> SEQUENCE: 71
```

-continued cctgatgaaa hccaacctaa gktatatcag gaa                                 33

<210> SEQ ID NO 72
<211> LENGTH: 33
<212> TYPE: DNA
<213> ORGANISM: Artificial Sequence
<220> FEATURE:
<223> OTHER INFORMATION: Primer Se_recomb3b_for

<400> SEQUENCE: 72
cctgatgaag yacaacctaa gktatatcag gaa                                 33

<210> SEQ ID NO 73
<211> LENGTH: 33
<212> TYPE: DNA
<213> ORGANISM: Artificial Sequence
<220> FEATURE:
<223> OTHER INFORMATION: Primer Se_recomb3a_rev

<400> SEQUENCE: 73
ttcctgatat amcttaggtt ggdtttcatc agg                                 33

<210> SEQ ID NO 74
<211> LENGTH: 33
<212> TYPE: DNA
<213> ORGANISM: Artificial Sequence
<220> FEATURE:
<223> OTHER INFORMATION: Primer Se_recomb3b_rev

<400> SEQUENCE: 74
ttcctgatat amcttaggtt gtrcttcatc agg                                 33

<210> SEQ ID NO 75
<211> LENGTH: 27
<212> TYPE: DNA
<213> ORGANISM: Artificial Sequence
<220> FEATURE:
<223> OTHER INFORMATION: Primer Se_recomb4a_L57TYA_for

<400> SEQUENCE: 75
gtcgatgtta gagttggcty aagagaa                                        27

<210> SEQ ID NO 76
<211> LENGTH: 27
<212> TYPE: DNA
<213> ORGANISM: Artificial Sequence
<220> FEATURE:
<223> OTHER INFORMATION: Primer Se_recomb4a_L57TYA_rev

<400> SEQUENCE: 76
ttctcttrag ccaactctaa catcgac                                        27

<210> SEQ ID NO 77
<211> LENGTH: 27
<212> TYPE: DNA
<213> ORGANISM: Artificial Sequence
<220> FEATURE:
<223> OTHER INFORMATION: Primer Se_recomb4b_L57CRA_for

<400> SEQUENCE: 77
gtcgatgtta gagttggccr aagagaa                                        27

<210> SEQ ID NO 78
<211> LENGTH: 27
<212> TYPE: DNA
<213> ORGANISM: Artificial Sequence -continued
<220> FEATURE:
<223> OTHER INFORMATION: Primer Se_recomb4b_L57CRA_rev

<400> SEQUENCE: 78
ttctcttygg ccaactctaa catcgac                                           27

<210> SEQ ID NO 79
<211> LENGTH: 33
<212> TYPE: DNA
<213> ORGANISM: Artificial Sequence
<220> FEATURE:
<223> OTHER INFORMATION: Primer Se_L57NNK_R58P_S61TSC_for
<220> FEATURE:
<221> NAME/KEY: misc_feature
<222> LOCATION: (10)..(11)
<223> OTHER INFORMATION: n is a, c, g, or t

<400> SEQUENCE: 79
agagttggcn nkccagaagg ctsctctagt tgg                                    33

<210> SEQ ID NO 80
<211> LENGTH: 33
<212> TYPE: DNA
<213> ORGANISM: Artificial Sequence
<220> FEATURE:
<223> OTHER INFORMATION: Primer Se_L57NNK_R58P_S61TSC_rev
<220> FEATURE:
<221> NAME/KEY: misc_feature
<222> LOCATION: (23)..(24)
<223> OTHER INFORMATION: n is a, c, g, or t

<400> SEQUENCE: 80
ccaactagag sagccttctg gmnngccaac tct                                    33

<210> SEQ ID NO 81
<211> LENGTH: 39
<212> TYPE: DNA
<213> ORGANISM: Artificial Sequence
<220> FEATURE:
<223> OTHER INFORMATION: Primer Serec4_fancy3_rec_A_for

<400> SEQUENCE: 81
gttagagttg gcgtaccaga agkatgctct agttggaaa                              39

<210> SEQ ID NO 82
<211> LENGTH: 39
<212> TYPE: DNA
<213> ORGANISM: Artificial Sequence
<220> FEATURE:
<223> OTHER INFORMATION: Primer Serec4_fancy3_rec_A_rev

<400> SEQUENCE: 82
tttccaacta gagcatmctt ctggtacgcc aactctaac                              39

<210> SEQ ID NO 83
<211> LENGTH: 36
<212> TYPE: DNA
<213> ORGANISM: Artificial Sequence
<220> FEATURE:
<223> OTHER INFORMATION: Primer Serec4_fancy3_rec_B_for

<400> SEQUENCE: 83
cctgatgaar yacaacctaa gktatatcag gaacat                                 36

<210> SEQ ID NO 84
<211> LENGTH: 36
<212> TYPE: DNA

<213> ORGANISM: Artificial Sequence
<220> FEATURE:
<223> OTHER INFORMATION: Primer Serec4_fancy3_rec_B_rev

<400> SEQUENCE: 84
atgttcctga tatamcttag gttgtryttc atcagg                                36

<210> SEQ ID NO 85
<211> LENGTH: 39
<212> TYPE: DNA
<213> ORGANISM: Artificial Sequence
<220> FEATURE:
<223> OTHER INFORMATION: Primer Se1_S63D_S61D_for

<400> SEQUENCE: 85
ggcttaagag aaggcgactc tgactggaaa acggctgag                             39

<210> SEQ ID NO 86
<211> LENGTH: 39
<212> TYPE: DNA
<213> ORGANISM: Artificial Sequence
<220> FEATURE:
<223> OTHER INFORMATION: Primer Se1_S63D_S61D_rev

<400> SEQUENCE: 86
ctcagccgtt ttccagtcag agtcgccttc tcttaagcc                             39

<210> SEQ ID NO 87
<211> LENGTH: 39
<212> TYPE: DNA
<213> ORGANISM: Artificial Sequence
<220> FEATURE:
<223> OTHER INFORMATION: Primer SeAA10R58S62NNK_for
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 87
gttggcttan nkgaaggctg cnnkgattgg aaaacggct                             39

<210> SEQ ID NO 88
<211> LENGTH: 39
<212> TYPE: DNA
<213> ORGANISM: Artificial Sequence
<220> FEATURE:
<223> OTHER INFORMATION: Primer SeAA10R58S62NNK_rev
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 88
agccgttttc caatcmnngc agccttcmnn taagccaac                             39

<210> SEQ ID NO 89
<211> LENGTH: 1053
<212> TYPE: DNA
<213> ORGANISM: Slackia exigua
<220> FEATURE:
<221> NAME/KEY: misc_feature -continued
<222> LOCATION: (1)..(1053)
<223> OTHER INFORMATION: Se1_NKR_v1

<400> SEQUENCE: 89

```
atgtccgtca agacaaaaga aaaggaaatg gcagttacaa ttttatacga acaagacgtt      60
gatccaaagg ttatccaagg tttgaaggtt ggtatcatag gttacggttc tcaaggtcac     120
gctcatgcat tgaacttaat ggattcaggt gttgatgtca gagttggttt gagagaaggt     180
gactctgatt ggaagacagc cgaagaagct ggtttaaagg ttacagatat tgacactgcc     240
gcagaagaag cagatgttat tatggtctta attcctgatg aagttcaacc aaaggtttac     300
caagaacata ttgcagctca tttgaaggct ggtaatacct tggcttttgc acacggtttc     360
aatatccatt acggttatat cgttcctcca gaagacgtta atgtcatcat gtgtgctcct     420
aaaggtccag gtcacatcgt tagaagacaa ttcaccgaag ttcaggtgt ccctgatttg      480 gcatgtgttc aacaagatgc aactggtaat gcatgggata ttgtttatc ctattgttgg      540 ggtgttggtg gtgcaagatc aggtatcata aaagctacat cgcagaaga aacagaagaa      600 gacttgtttg gtgaacaagc agttttgtgt ggtggtttag ttgaattggt caaagctggt     660
tttgaaacct tgactgaagc tggttatcca cctgaattgg cctactttga atgttatcac     720
gaaatgaaga tgatcgttga cttgatgtat gaatctggta ttcattttat gaactactca     780
atctctaaca ctgcagaata cggtgaatac atgccggtc ctaaagtcat caatgaacaa      840
agtagagaag caatgaaaga aatcttggct agaatccaag acggttcatt tgctcaagaa     900
tttgtcgatg actgcaataa tggtcataag agattgttag aacaaagaga agctattaac     960
actcatccaa tcgaaactac aggtgctaga atcagatcaa tgtttttcttg gataaagaag    1020 gaagatttgg aacaccacca tcatcaccac tga                                 1053
```

<210> SEQ ID NO 90
<211> LENGTH: 350
<212> TYPE: PRT
<213> ORGANISM: Slackia exigua
<220> FEATURE:
<221> NAME/KEY: SITE
<222> LOCATION: (1)..(350)
<223> OTHER INFORMATION: Se1_NKR_v1 protein

<400> SEQUENCE: 90

```
Met Ser Val Lys Thr Lys Glu Lys Glu Met Ala Val Thr Ile Leu Tyr
1               5                   10                  15

Glu Gln Asp Val Asp Pro Lys Val Ile Gln Gly Leu Lys Val Gly Ile
            20                  25                  30

Ile Gly Tyr Gly Ser Gln Gly His Ala His Ala Leu Asn Leu Met Asp
        35                  40                  45

Ser Gly Val Asp Val Arg Val Gly Leu Arg Glu Gly Asp Ser Asp Trp
    50                  55                  60

Lys Thr Ala Glu Glu Ala Gly Leu Lys Val Thr Asp Ile Asp Thr Ala
65                  70                  75                  80

Ala Glu Glu Ala Asp Val Ile Met Val Leu Ile Pro Asp Glu Val Gln
                85                  90                  95

Pro Lys Val Tyr Gln Glu His Ile Ala Ala His Leu Lys Ala Gly Asn
            100                 105                 110

Thr Leu Ala Phe Ala His Gly Phe Asn Ile His Tyr Gly Tyr Ile Val
        115                 120                 125

Pro Pro Glu Asp Val Asn Val Ile Met Cys Ala Pro Lys Gly Pro Gly
    130                 135                 140
```

-continued

```
His Ile Val Arg Arg Gln Phe Thr Glu Gly Ser Gly Val Pro Asp Leu
145                 150                 155                 160

Ala Cys Val Gln Gln Asp Ala Thr Gly Asn Ala Trp Asp Ile Val Leu
                165                 170                 175

Ser Tyr Cys Trp Gly Val Gly Gly Ala Arg Ser Gly Ile Ile Lys Ala
            180                 185                 190

Thr Phe Ala Glu Glu Thr Glu Glu Asp Leu Phe Gly Glu Gln Ala Val
            195                 200                 205

Leu Cys Gly Gly Leu Val Glu Leu Val Lys Ala Gly Phe Glu Thr Leu
    210                 215                 220

Thr Glu Ala Gly Tyr Pro Pro Glu Leu Ala Tyr Phe Glu Cys Tyr His
225                 230                 235                 240

Glu Met Lys Met Ile Val Asp Leu Met Tyr Glu Ser Gly Ile His Phe
                245                 250                 255

Met Asn Tyr Ser Ile Ser Asn Thr Ala Glu Tyr Gly Glu Tyr Tyr Ala
            260                 265                 270

Gly Pro Lys Val Ile Asn Glu Gln Ser Arg Glu Ala Met Lys Glu Ile
            275                 280                 285

Leu Ala Arg Ile Gln Asp Gly Ser Phe Ala Gln Glu Phe Val Asp Asp
    290                 295                 300

Cys Asn Asn Gly His Lys Arg Leu Leu Glu Gln Arg Glu Ala Ile Asn
305                 310                 315                 320

Thr His Pro Ile Glu Thr Thr Gly Ala Arg Ile Arg Ser Met Phe Ser
                325                 330                 335

Trp Ile Lys Lys Glu Asp Leu Glu His His His His His His
            340                 345                 350

<210> SEQ ID NO 91
<211> LENGTH: 1053
<212> TYPE: DNA
<213> ORGANISM: Slackia exigua
<220> FEATURE:
<221> NAME/KEY: misc_feature
<222> LOCATION: (1)..(1053)
<223> OTHER INFORMATION: Se1_NKR_v48

<400> SEQUENCE: 91
atgtccgtca agacaaaaga aaaggaaatg gcagttacaa ttttatacga acaagacgtt      60
gatccaaagg ttatccaagg tttgaaggtt gctatcatag gttacggttc tcaaggtcac     120
gctcatgcat tgaacttaat ggattcaggt gttgatgtca gagttggttt gagagaaggt     180
gactctgatt ggaagacagc cgaagaagct ggtttaaagg ttacagatat tgacactgcc     240
gcagaagaag cagatgttat tatggtctta gttcctgatg aagttcaacc aaaggtttac     300
caagaacata ttgcagctca tttgaaggct ggtaatacct ggcttttgc acacggtttc     360 aatatccatt acggttatat cgttcctcca gaagacgtta atgtcatcat gtgtgctcct     420
aaaggtccag gtcacatcgt tagaagacaa ttcaccgaag ttcaggtgt ccctgatttg     480 gcatgtgttc aacaagatgc aactggtaat gcatgggata ttgtttatc ctattgttgg     540 ggtgttggtg gtgcaagatc aggtatcata aaagctacat cgcagaaga aacagaagaa     600 gacttgtttg gtgaacaagc agttttgtgt ggtggtttag ttgaattggt caaagctggt     660
tttgaaacct tgactgaagc tggttatcca cctgaattgg cctactttga atgttatcac     720
gaaatgaaga tgatcgttga cttgatgtat gaatctggta ttcattttat gaactactca     780
atctctaaca ctgcagaata cggtgaatac tatgccggtc ctaaagtcat caatgaacaa     840
```

-continued

```
agtagagaag caatgaaaga aatcttgaaa agaatccaag acggttcatt tgctcaagaa      900
tttgtcgatg actgcaataa tggtcataag agattgttag aacaaagaga agctattaac      960
actcatccaa tcgaaactac aggtgctaga atcagatcaa tgttttcttg gataaagaag     1020
gaagatttgg aacaccacca tcatcaccac tga                                  1053
```

```
<210> SEQ ID NO 92
<211> LENGTH: 350
<212> TYPE: PRT
<213> ORGANISM: Slackia exigua
<220> FEATURE:
<221> NAME/KEY: SITE
<222> LOCATION: (1)..(350)
<223> OTHER INFORMATION: Sel_NKR_v48 protein

<400> SEQUENCE: 92

Met Ser Val Lys Thr Lys Glu Lys Glu Met Ala Val Thr Ile Leu Tyr
1               5                   10                  15

Glu Gln Asp Val Asp Pro Lys Val Ile Gln Gly Leu Lys Val Ala Ile
                20                  25                  30

Ile Gly Tyr Gly Ser Gln Gly His Ala His Ala Leu Asn Leu Met Asp
            35                  40                  45

Ser Gly Val Asp Val Arg Val Gly Leu Arg Glu Gly Asp Ser Asp Trp
        50                  55                  60

Lys Thr Ala Glu Glu Ala Gly Leu Lys Val Thr Asp Ile Asp Thr Ala
65                  70                  75                  80

Ala Glu Glu Ala Asp Val Ile Met Val Leu Val Pro Asp Glu Val Gln
                85                  90                  95

Pro Lys Val Tyr Gln Glu His Ile Ala Ala His Leu Lys Ala Gly Asn
                100                 105                 110

Thr Leu Ala Phe Ala His Gly Phe Asn Ile His Tyr Gly Tyr Ile Val
            115                 120                 125

Pro Pro Glu Asp Val Asn Val Ile Met Cys Ala Pro Lys Gly Pro Gly
        130                 135                 140

His Ile Val Arg Arg Gln Phe Thr Glu Gly Ser Gly Val Pro Asp Leu
145                 150                 155                 160

Ala Cys Val Gln Gln Asp Ala Thr Gly Asn Ala Trp Asp Ile Val Leu
            165                 170                 175

Ser Tyr Cys Trp Gly Val Gly Gly Ala Arg Ser Gly Ile Ile Lys Ala
            180                 185                 190

Thr Phe Ala Glu Glu Thr Glu Glu Asp Leu Phe Gly Glu Gln Ala Val
            195                 200                 205

Leu Cys Gly Gly Leu Val Glu Leu Val Lys Ala Gly Phe Glu Thr Leu
        210                 215                 220

Thr Glu Ala Gly Tyr Pro Pro Glu Leu Ala Tyr Phe Glu Cys Tyr His
225                 230                 235                 240

Glu Met Lys Met Ile Val Asp Leu Met Tyr Glu Ser Gly Ile His Phe
                245                 250                 255

Met Asn Tyr Ser Ile Ser Asn Thr Ala Glu Tyr Gly Glu Tyr Tyr Ala
            260                 265                 270

Gly Pro Lys Val Ile Asn Glu Gln Ser Arg Glu Ala Met Lys Glu Ile
            275                 280                 285

Leu Lys Arg Ile Gln Asp Gly Ser Phe Ala Gln Glu Phe Val Asp Asp
        290                 295                 300

Cys Asn Asn Gly His Lys Arg Leu Leu Glu Gln Arg Glu Ala Ile Asn
```

-continued

```
305             310             315             320
Thr His Pro Ile Glu Thr Thr Gly Ala Arg Ile Arg Ser Met Phe Ser
                325             330             335

Trp Ile Lys Lys Glu Asp Leu Glu His His His His His His
        340             345             350

<210> SEQ ID NO 93
<211> LENGTH: 1053
<212> TYPE: DNA
<213> ORGANISM: Slackia exigua
<220> FEATURE:
<221> NAME/KEY: misc_feature
<222> LOCATION: (1)..(1053)
<223> OTHER INFORMATION: Se1_NKR_v65

<400> SEQUENCE: 93
atgtccgtca agacaaaaga aaaggaaatg gcagttacaa ttttatacga acaagacgtt       60
gatccaaagg ttatccaagg tttgaaggtt gctatcatag gttacggttc tcaaggtcac      120
gctcatgcat tgaacttaat ggattcaggt gttgatgtca gagttggttt gagagaaggt      180
gactctgatt ggaagacagc cgaagaagct ggtttaaagg ttacagatat ggacactgcc      240
gcagaagaag cagatgttat tatggtctta attcctgatg aagttcaacc aaaggtttac      300
caagaacata ttgcagctca tttgaaggct ggtaatacct ggctttttgc acacggtttc      360
aatatccatt acggttatat cgttcctcca gaagacgtta atgtcatcat gtgtgctcct      420
aaaggtccag gtcacatcgt tagaagacaa ttcaccgaag gttcaggtgt ccctgatttg      480
gcatgtgttc aacaagatgc aactggtaat gcatgggata ttgtttttatc ctattgttgg      540 ggtgttggtg gtgcaagatc aggtatcata aaagctacat tcgcagaaga aacagaagaa      600
gacttgtttg gtgaacaagc agttttgtgt ggtggtttag ttgaattggt caaagctggt      660
tttgaaacct tgactgaagc tggttatcca cctgaattgg cctactttga atgttatcac      720
gaaatgaaga tgatcgttga cttgatgtat gaatctggta ttcattttat gaactactca      780
atctctaaca ctgcagaata cggtgaatac tatgccggtc ctaaagtcat caatgaacaa      840
agtagagaag caatgaaaga aatcttgaaa agaatccaag acggttcatt tgctcaagaa      900
tttgtcgatg actgcaataa tggtcataag agattgttag aacaaagaga agctattaac      960
actcatccaa tcgaaactac aggtgctaga atcagatcaa tgtttttcttg gataaagaag     1020 gaagatttgg aacaccacca tcatcaccac tga                                   1053

<210> SEQ ID NO 94
<211> LENGTH: 350
<212> TYPE: PRT
<213> ORGANISM: Slackia exigua
<220> FEATURE:
<221> NAME/KEY: SITE
<222> LOCATION: (1)..(350)
<223> OTHER INFORMATION: Se1_NKR_v65 protein

<400> SEQUENCE: 94

Met Ser Val Lys Thr Lys Glu Lys Glu Met Ala Val Thr Ile Leu Tyr
1               5               10              15

Glu Gln Asp Val Asp Pro Lys Val Ile Gln Gly Leu Lys Val Ala Ile
                20              25              30

Ile Gly Tyr Gly Ser Gln Gly His Ala His Ala Leu Asn Leu Met Asp
        35              40              45

Ser Gly Val Asp Val Arg Val Gly Leu Arg Glu Gly Asp Ser Asp Trp
    50              55              60
```

-continued

```
Lys Thr Ala Glu Glu Ala Gly Leu Lys Val Thr Asp Met Asp Thr Ala
65              70              75              80

Ala Glu Glu Ala Asp Val Ile Met Val Leu Ile Pro Asp Glu Val Gln
            85              90              95

Pro Lys Val Tyr Gln Glu His Ile Ala Ala His Leu Lys Ala Gly Asn
            100             105             110

Thr Leu Ala Phe Ala His Gly Phe Asn Ile His Tyr Gly Tyr Ile Val
            115             120             125

Pro Pro Glu Asp Val Asn Val Ile Met Cys Ala Pro Lys Gly Pro Gly
    130             135             140

His Ile Val Arg Arg Gln Phe Thr Glu Gly Ser Gly Val Pro Asp Leu
145             150             155             160

Ala Cys Val Gln Gln Asp Ala Thr Gly Asn Ala Trp Asp Ile Val Leu
            165             170             175

Ser Tyr Cys Trp Gly Val Gly Gly Ala Arg Ser Gly Ile Ile Lys Ala
            180             185             190

Thr Phe Ala Glu Glu Thr Glu Glu Asp Leu Phe Gly Glu Gln Ala Val
            195             200             205

Leu Cys Gly Gly Leu Val Glu Leu Val Lys Ala Gly Phe Glu Thr Leu
    210             215             220

Thr Glu Ala Gly Tyr Pro Pro Glu Leu Ala Tyr Phe Glu Cys Tyr His
225             230             235             240

Glu Met Lys Met Ile Val Asp Leu Met Tyr Glu Ser Gly Ile His Phe
            245             250             255

Met Asn Tyr Ser Ile Ser Asn Thr Ala Glu Tyr Gly Glu Tyr Tyr Ala
            260             265             270

Gly Pro Lys Val Ile Asn Glu Gln Ser Arg Glu Ala Met Lys Glu Ile
            275             280             285

Leu Lys Arg Ile Gln Asp Gly Ser Phe Ala Gln Glu Phe Val Asp Asp
    290             295             300

Cys Asn Asn Gly His Lys Arg Leu Leu Glu Gln Arg Glu Ala Ile Asn
305             310             315             320

Thr His Pro Ile Glu Thr Thr Gly Ala Arg Ile Arg Ser Met Phe Ser
            325             330             335

Trp Ile Lys Lys Glu Asp Leu Glu His His His His His His
            340             345             350
```